United States Patent
Juhl et al.

(10) Patent No.: US 11,111,263 B2
(45) Date of Patent: Sep. 7, 2021

(54) PROCESS FOR THE MANUFACTURE OF (2S,3S,4S,5R,6S)-3,4,5-TRIHYDROXY-6-(((4AR, 10AR)-7-HYDROXY-1-PROPYL-1,2,3,4,4A,5,10, 10A-OCTAHYDROBENZO[G]QUINOLIN-6-YL)OXY)TETRAHYDRO-2H-PYRAN-2-CARBOXYLIC ACID

(71) Applicant: H. Lundbeck A/S, Valby (DK)

(72) Inventors: Martin Juhl, Valby (DK); Frans Dennis Therkelsen, Valby (DK); Tobias Gylling Frihed, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/876,878

(22) Filed: May 18, 2020

(65) Prior Publication Data

US 2020/0369706 A1 Nov. 26, 2020

(30) Foreign Application Priority Data

May 20, 2019 (DK) .............................. PA201900599
May 24, 2019 (DK) .............................. PA201900636

(51) Int. Cl.
*C07H 15/26* (2006.01)
*C07H 1/00* (2006.01)

(52) U.S. Cl.
CPC .............. *C07H 15/26* (2013.01); *C07H 1/00* (2013.01)

(58) Field of Classification Search
None
See application file for complete search history.

(56) References Cited

U.S. PATENT DOCUMENTS

| | | | |
|---|---|---|---|
| 4,543,256 | A | 9/1985 | Neumeyer |
| 4,565,818 | A | 1/1986 | Nordmann et al. |
| 4,692,453 | A | 9/1987 | Seiler |
| 5,747,513 | A | 5/1998 | Montanari et al. |
| 5,885,988 | A | 3/1999 | Neumann et al. |
| 5,955,468 | A | 9/1999 | Markstein |
| 8,129,530 | B2 | 3/2012 | Jorgensen et al. |
| 10,729,710 | B2 | 8/2020 | Jensen et al. |
| 2009/0062324 | A1 | 3/2009 | Jorgensen et al. |
| 2012/0077836 | A1 | 3/2012 | Wilkstrom et al. |
| 2017/0335357 | A1 | 11/2017 | Divi et al. |
| 2020/0338102 | A1 | 1/2020 | Balmer et al. |
| 2020/0369615 | A1 | 11/2020 | Jacobsen et al. |
| 2020/0369705 | A1 | 11/2020 | Juhl et al. |
| 2020/0392176 | A1 | 12/2020 | Jensen et al. |

FOREIGN PATENT DOCUMENTS

| | | |
|---|---|---|
| CN | 102746351 A | 10/2012 |
| CN | 105218606 A | 1/2016 |
| GB | 2 192 394 A | 1/1998 |
| JP | S60-172975 A | 9/1985 |
| WO | 90/12574 A1 | 11/1990 |
| WO | 97/03054 A1 | 1/1997 |
| WO | 98/38155 A1 | 9/1998 |
| WO | 00/47571 A1 | 8/2000 |
| WO | 01/36428 A1 | 5/2001 |
| WO | 01/76602 A1 | 10/2001 |
| WO | WO 2001/078713 A1 | 10/2001 |
| WO | 02/13827 A1 | 2/2002 |
| WO | WO 2002/100377 A1 | 12/2002 |
| WO | 03/006458 A1 | 1/2003 |
| WO | 03/013532 A1 | 2/2003 |
| WO | 03/074511 A1 | 9/2003 |
| WO | 03/080074 A1 | 10/2003 |
| WO | 2005/062894 A2 | 7/2005 |
| WO | 2006/012640 A2 | 2/2006 |
| WO | 2006/056604 A1 | 6/2006 |
| WO | WO 2009/026934 A1 | 3/2009 |
| WO | WO 2009/026935 A1 | 3/2009 |
| WO | WO 2010/097092 A1 | 9/2010 |
| WO | 2013/020979 A1 | 2/2013 |
| WO | 2013/034119 A1 | 3/2013 |
| WO | 2015/067927 A1 | 5/2015 |

(Continued)

OTHER PUBLICATIONS

International Search Report and Written Opinion dated Jul. 2, 2020 in connection with Application No. PCT/EP2020/063909.
Alexander et al., Functional architecture of basal ganglia circuits: neural substrates of parallel processing. Trends Neurosci. Jul. 1990;13(7):266-71. doi: 10.1016/0166-2236(90)90107-1.
Bibbiani et al., Continuous dopaminergic stimulation reduces risk of motor complications in parkinsonian primates. Exp Neurol. Mar. 2005;192(1):73-8. doi: 10.1016/j.expneurol.2004.11.013.

(Continued)

*Primary Examiner* — Layla D Berry
(74) *Attorney, Agent, or Firm* — Wolf, Greenfield & Sacks, P.C.

(57) ABSTRACT

The present invention relates to a process for manufacturing (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid with the formula (Id) below and salts thereof

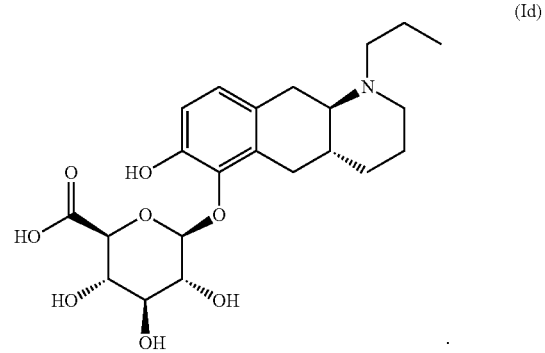

(Id)

The compound of formula (Id) is a prodrug of a catecholamine for use in treatment of neurodegenerative diseases and disorders such as Parkinson's Disease.
The invention also relates to new intermediates of said process.

18 Claims, 7 Drawing Sheets

(56) References Cited

FOREIGN PATENT DOCUMENTS

WO 2017/184871 A1 10/2017
WO WO 2019/101917 A1 5/2019

OTHER PUBLICATIONS

Campbell et al., Behavioral effects of (-)10,11-methylenedioxy-N-n-propylnoraporphine, an orally effective long-acting agent active at central dopamine receptors, and analogous aporphines. Neuropharmacology. Oct. 1982;21(10):953-61. doi: 10.1016/0028-3908(82)90106-x.
Cannon et al., N?Alkyl derivatives of trans?6, 7?dihydroxy?1, 2, 3, 4, 4a, 5, 10, 10b?octahydrobenzo [g] quinoline A congener of apomorphine lacking the non?oxygenated aromatic ring. J Heterocycl Chem. Nov. 1980;17(7):1633-6.
Cavero et al., Safety Pharmacology assessment of drugs with biased 5-HT(2B) receptor agonism mediating cardiac valvulopathy. J Pharmacol Toxicol Methods. Mar.-Apr. 2014;69(2):150-61. doi: 10.1016/j.vascn.2013.12.004. Epub Dec. 19, 2013.
Delong et al., Primate models of movement disorders of basal ganglia origin. Trends Neurosci. Jul. 1990;13(7):281-5. doi: 10.1016/0166-2236(90)90110-v.
Gerfen et al., D1 and D2 dopamine receptor-regulated gene expression of striatonigral and striatopallidal neurons. Science. Dec. 7, 1990;250(4986):1429-32. doi: 10.1126/science.2147780.
Giardina et al., Adrogolide HCl (ABT-431; DAS-431), a prodrug of the dopamine D1 receptor agonist, A-86929: preclinical pharmacology and clinical data. CNS Drug Rev. 2001 Fall;7(3):305-16. doi: 10.1111/j.1527-3458.2001.tb00201.x.
Goswami et al., Intestinal absorption and metabolism of retinoyl beta-glucuronide in humans, and of 15-[14C]-retinoyl beta-glucuronide in rats of different vitamin A status. J Nutr Biochem. Dec. 2003;14(12):703-9. doi: 10.1016/j.jnutbio.2003.08.008.
Grosset et al., Inhaled dry powder apomorphine (VR040) for 'off' periods in Parkinson's disease: an in-clinic double-blind dose ranging study. Acta Neurol Scand. Sep. 2013;128(3):166-71. doi: 10.1111/ane.12107. Epub Mar. 26, 2013.
Hauser et al., Sublingual apomorphine (APL-130277) for the acute conversion of Off to On in Parkinson's disease. Mov Disord. Sep. 2016;31(9):1366-72. doi: 10.1002/mds.26697. Epub Jul. 19, 2016.
Liu et al., A novel synthesis and pharmacological evaluation of a potential dopamine D1/D2 agonist: 1-propyl-1,2,3,4,4a,5,10,10a-octahydrobenzo[g]quinoline-6,7-diol. Bioorg Med Chem. Mar. 15, 2008;16(6):3438-44. doi: 10.1016/j.bmc.2007.06.036. Epub Jun. 23, 2007.
Liu et al., Extremely potent orally active benzo[g]quinoline analogue of the dopaminergic prodrug: 1-propyl-trans-2,3,4,4a,5,7,8,9,10,10a-decahydro-1H-benzo-[g]quinolin-6-one [corrected]. J Med Chem. Feb. 23, 2006;49(4):1494-8. doi: 10.1021/jm051111h.
Loozen et al., An approach to the synthesis of [2] benzopyrano [3, 4?c] pyrroles; alternative dopaminergic molecules. Recueil des Travaux Chimiques des Pays?Bas. 1982;101(9):298-310.
Nolen et al., Budesonide-beta-D-glucuronide: a potential prodrug for treatment of ulcerative colitis. J Pharm Sci. Jun. 1995;84(6):677-81. doi: 10.1002/jps.2600840603.
Poewe et al., Parkinson disease. Nat Rev Dis Primers. Mar. 23, 2017;3:17013. doi: 10.1038/nrdp.2017.13.
Rothman et al., Evidence for possible involvement of 5-HT(2B) receptors in the cardiac valvulopathy associated with fenfluramine and other serotonergic medications. Circulation. Dec. 5, 2000;102(23):2836-41. doi: 10.1161/01.cir.102.23.2836.
Sozio et al., Designing prodrugs for the treatment of Parkinson's disease. Expert Opin Drug Discov. May 2012;7(5):385-406. doi: 10.1517/17460441.2012.677025. Epub Apr. 12, 2012.
Sprenger et al., Management of motor and non-motor symptoms in Parkinson's disease. CNS Drugs. Apr. 2013;27(4):259-72. doi: 10.1007/s40263-013-0053-2.
Stain-Texier et al., Intestinal absorption and stability of morphine 6-glucuronide in different physiological compartments of the rat. Drug Metab Dispos. May 1998;26(5):383-7.
International Search Report and Written Opinion for Application No. PCT/EP2018/082361 dated Feb. 22, 2019.
International Search Report and Written Opinion for Application No. PCT/EP2020/063910 dated Jul. 14, 2020.
International Search Report and Written Opinion for Application No. PCT/EP2020/063913 dated Jul. 15, 2020.
International Search Report and Written Opinion for Application No. PCT/EP2020/063908 dated Sep. 11, 2020.
Ahari et al., A direct stereoselective approach to trans-2,3-disubstituted piperidines: application in the synthesis of 2-Epi-CP-99,994 and (+)-epilupinine. Org Lett. Jun. 19, 2008;10(12):2473-6. doi: 10.1021/ol800722a. Epub May 14, 2008.
Billeter et al., 8-Hydroxyflavonoid Glucuronides from Malva Sylvestris. Phytochemistry. 1991; 30(3):987-90.
Brown et al., Structurally constrained hybrid derivatives containing octahydrobenzo[g or f]quinoline moieties for dopamine D2 and D3 receptors: binding characterization at D2/D3 receptors and elucidation of a pharmacophore model. J Med Chem. Dec. 25, 2008;51(24):7806-19. doi: 10.1021/jm8008629.
Fan et al., Differential effects of pro-BDNF on sensory neurons after sciatic nerve transection in neonatal rats. Eur J Neurosci. May 2008;27(9):2380-90. doi: 10.1111/j.1460-9568.2008.06215.x. Epub Apr. 22, 2008.
Fan et al., Modifications of the isonipecotic acid fragment of SNS-032: analogs with improved permeability and lower efflux ratio. Bioorg Med Chem Lett. Dec. 1, 2008;18(23):6236-9. doi: 10.1016/j.bmcl.2008.09.099. Epub Oct. 2, 2008. (citation on PubMed).
Fumeaux et al., First synthesis, characterization, and evidence for the presence of hydroxycinnamic acid sulfate and glucuronide conjugates in human biological fluids as a result of coffee consumption. Org Biomol Chem. Nov. 21, 2010;8(22):5199-211. doi: 10.1039/c0ob00137f. Epub Sep. 14, 2010.
Knobloch et al., Keto Esters Derived from 2-(Trimethylsilyl) ethanol: An Orthogonal Protective Group for β-Keto Esters. Synthesis 2008.14 (2008): 2229-2246.
Kotsuki et al., Highly practical, enantiospecific synthesis of the cyclohexyl fragment of the immunosuppressant FK-506. J Org Chem. Aug. 1992;57(18):5036-40.
Morissette et al., High-throughput crystallization: polymorphs, salts, co-crystals and solvates of pharmaceutical solids. Adv Drug Deliv Rev. Feb. 23, 2004;56(3):275-300. doi: 10.1016/j.addr.2003.10.020.
Zhang et al., Flavonoid metabolism: the synthesis of phenolic glucuronides and sulfates as candidate metabolites for bioactivity studies of dietary flavonoids. Tetrahedron. Jun. 2012; 68(22):4194-4201.
U.S. Appl. No. 16/198,917, filed Nov. 23, 2018, Granted, U.S. Pat. No. 10,729,710.
U.S. Appl. No. 16/872,802, filed May 12, 2020, Allowed, 2020-0338102[2].
U.S. Appl. No. 16/876,843, filed May 18, 2020, Allowed, 2020-0369705[2].
U.S. Appl. No. 876,908, filed May 18, 2020, Published, 2020-0392176[2].
U.S. Appl. No. 16/876,966, filed May 18, 2020, Published, 2020-0369615[2].
PCT/EP2018/082361, dated Feb. 22, 2019, International Search Report and Written Opinion.
PCT/EP2020/063910, dated Jul. 14, 2020, International Search Report and Written Opinion.
PCT/EP2020/063913, dated Jul. 15, 2020, International Search Report and Written Opinion.
PCT/EP2020/063908, dated Sep. 11, 2020, International Search Report and Written Opinion.

PROCESS FOR THE MANUFACTURE OF (2S,3S,4S,5R,6S)-3,4,5-TRIHYDROXY-6-(((4AR, 10AR)-7-HYDROXY-1-PROPYL-1,2,3,4,4A,5,10, 10A-OCTAHYDROBENZO[G]QUINOLIN-6-YL) OXY)TETRAHYDRO-2H-PYRAN-2-CARBOXYLIC ACID

CROSS-REFERENCE TO RELATED APPLICATIONS

This application claims priority to Danish Application No. PA201900599, filed May 20, 2019, and Danish Application No. PA201900636, filed May 24, 2019, the entire contents of the aforementioned applications are hereby incorporated herein by reference.

FIELD OF THE INVENTION

The present invention relates to a process for manufacturing (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid which is a compound for use in the treatment of neurodegenerative diseases and disorders such as Parkinson's Disease. The invention also relates to new intermediates of said process.

BACKGROUND OF THE INVENTION

Parkinson's disease (PD) is a common neurodegenerative disorder that becomes increasingly prevalent with age and affects an estimated seven to ten million people worldwide. Parkinson's disease is a multi-faceted disease characterized by both motor and non-motor symptoms. Motor symptoms include resting tremor (shaking), bradykinesia/akinesia (slowness and poverty of movements), muscular rigidity, postural instability and gait dysfunction; whereas non-motor symptoms include neuropsychiatric disorders (e.g. depression, psychotic symptoms, anxiety, apathy, mild-cognitive impairment and dementia) as well as autonomic dysfunctions and sleep disturbances (Poewe et al., Nature Review, (2017) vol 3 article 17013: 1-21).

A key hallmark of Parkinson's disease pathophysiology is the loss of pigmented dopaminergic neurons in the substantia nigra pars compacta that provides dopaminergic innervation to the striatum and other brain areas. Such progressive neurodegeneration leads to the decrease in dopamine striatal levels which ultimately results in a series of changes in the basal ganglia circuitry, ultimately ending up in the occurrence of the four cardinal motor features of Parkinson's disease. The main target of dopamine in the striatum consists of medium spiny GABAergic neurons (MSNs) selectively expressing D1 or D2 receptors pending topographical projections. GABAergic-MSN projecting to the external pallidum, also called striato-pallidal 'indirect pathway' express D2 receptors (MSN-2); whereas GABAergic-MSN projecting to the substantia nigra pars reticulata and internal pallidum, also called striato-nigral 'direct pathway' express D1 receptors (MSN-1). Depletion of dopamine because of neuronal loss results in an imbalanced activity of the two pathways, resulting in a marked reduction of thalamic and cortical output activities and ultimately motor dysfunctions (Gerfen et al, Science (1990) 250: 1429-32; Delong, (1990) Trends in Neuroscience 13: 281-5; Alexander et Crutcher, (1990) Trends in Neuroscience 13: 266-71; and for review Poewe et al., Nature Review (2017) vol. 3 article 17013: 1-21).

The most effective therapeutic strategies available to patients suffering from Parkinson's disease, and aiming at controlling motor symptoms are primarily indirect and direct dopamine agonists. The classic and gold standard treatment regimen includes chronic oral intake of L-3,4-dihydroxyphenylalanine (L-DOPA) which is decarboxylated in the brain to form dopamine. Other approaches consist in the administration of dopamine receptor agonists such as apomorphine which acts both on the D1 and D2 receptors subtypes, or pramipexole, ropinirole and others which are predominantly directed towards D2 receptors subtypes. Optimal motor relief is obtained with use of both L-DOPA and apomorphine due to their activation of both D1 and D2 receptor subtypes and holistic re-equilibrium of the indirect-direct pathways (i.e. while D2 agonists only reverse the indirect pathway dysfunction).

L-DOPA and apomorphine with the structures depicted below are currently the most efficacious PD drugs in clinical use.

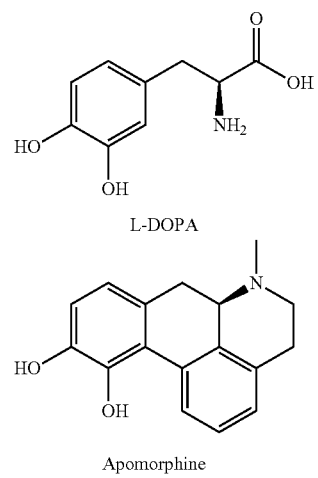

L-DOPA

Apomorphine

L-DOPA is a prodrug of dopamine and remains the most efficacious drug in the treatment of motor Parkinson's disease. However, after several years of treatment (i.e. honeymoon period), complications arise due the inherent progression of the disease (i.e. sustained loss of dopaminergic neurons) as well as poor pharmacokinetic (PK) profile of L-DOPA. Those complications include 1) dyskinesia which are abnormal involuntary movements occurring during the optimal 'on-time effect' of the drug; and 2) off fluctuations, period during which the L-DOPA positive effect wears off and symptoms re-emerge or worsen (Sprenger and Poewe, CNS Drugs (2013), 27: 259-272). Direct dopamine receptor agonists are able to activate the dopamine autoreceptors as well as the postsynaptic dopamine receptors located on the medium spiny neurons MSN-1 and MSN-2. Apomorphine belongs to a class of dopamine agonists with a 1,2-dihydroxybenzene (catechol) moiety. When combined with a phenethylamine motif, catecholamines often possess low or no oral bioavailability as is the case for apomorphine. Apomorphine is used clinically in PD therapy albeit with a non-oral delivery (typically intermittent subcutaneous administration or daytime continuous parenteral infusion via a pump). For apomorphine, animal studies have shown that transdermal delivery or implants may provide possible forms of administration. However, when the delivery of apomorphine from implants was studied in monkeys (Bibbiani et al., Chase Experimental Neurology (2005), 192: 73-78) it was found that in most cases the animals had to be treated with the immunosuppressant dexamethasone to prevent local irritation and other complications following the implantation surgery. Alternative delivery strategies for apomorphine therapy in PD such as inhalation and sublingual formulations have been extensively explored (see e.g. Grosset et al., Acta Neurol Scand. (2013), 128:166-171 and Hauser et al., Movement Disorders (2016), Vol. 32 (9): 1367-1372). However, these efforts are yet not in clinical use for the treatment of PD.

An alternative to the non-oral formulations of the catecholamines involves the use of a prodrug masking the free catechol hydroxyl groups to enable oral administration. However, a known problem associated with the development of prodrugs for clinical use is the difficulties associated with predicting conversion to the parent compound in humans.

Various ester prodrugs of catecholamines have been reported in the literature such as enterically coated N-propyl-noraporphine (NPA) and the mono pivaloyl ester of apomorphine for duodenal delivery (see eg. WO 02/100377), and the D1-like agonist adrogolide, a diacetyl prodrug of A-86929 (Giardina and Williams; CNS Drug Reviews (2001), Vol. 7 (3): 305-316). adrogolide undergoes extensive hepatic first-pass metabolism in man after oral dosing and, as a result, has a low oral bioavailability (app. 4%). In PD patients, intravenous (IV) adrogolide has anti-parkinson efficacy comparable to that of L-DOPA (Giardina and Williams; CNS Drug Reviews (2001), Vol. 7 (3): 305-316).

In addition to the ester prodrugs of catecholamines, an alternative prodrug approach involves the masking of the two catechol hydroxyl groups as the corresponding methylene-dioxy derivative or di-acetalyl derivative, as the acetal derived from other aldehydes than formaldehyde, or as the ketal derived from various ketones. This prodrug principle has been described for example in Campbell et al., Neuropharmacology (1982); 21(10): 953-961 and in U.S. Pat. No. 4,543,256, WO 2009/026934 and WO 2009/026935.

Yet another suggested approach for a catecholamine prodrug is the formation of an enone derivative as suggested in for example WO 2001/078713 and in Liu et al. Bioorganic Med. Chem. (2008), 16: 3438-3444. For further examples of catecholamine prodrugs see for example Sozio et al., Exp. Opin. Drug Disc. (2012); 7(5): 385-406.

The compound (4aR,10aR)-1-Propyl-1,2,3,4,4a,5,10,10a-octahydro-benzo[g]quinoline-6,7-diol depicted as compound (I) below is disclosed in WO 2009/026934. The trans-isomer was disclosed previously in Liu et al., J. Med. Chem. (2006), 49: 1494-1498 and then in Liu et al., Bioorganic Med. Chem. (2008), 16: 3438-3444 including pharmacological data indicating that the compound has a low oral bioavailability in rats. The racemate was disclosed for the first time in Cannon et al., J. Heterocyclic Chem. (1980); 17: 1633-1636.

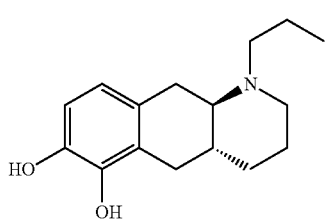

(I)

Compound (I) is a dopamine receptor agonist with mixed D1 and D2 activity. Some prodrug derivatives of compound (I) are known in the art.

Liu et al., J. Med. Chem. (2006), 49: 1494-1498 and Liu et al., Bioorganic Med. Chem. (2008), 16: 3438-3444 disclose the enone derivative of formula (Ia) depicted below which was shown to be converted to the active compound (I) in rats.

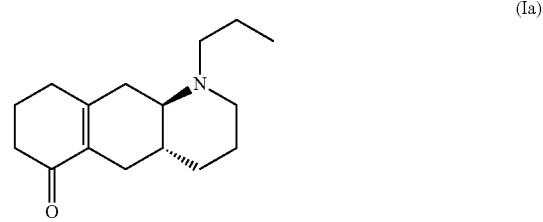 [SMILES: CCCN1CCC[C@@H]2CC3=C(CCCC3=O)C[C@H]21]

(Ia)

WO 2009/026934 and WO 2009/026935 disclose two types of prodrug derivatives of compound (I) including a compound with the formula (Ib) below:

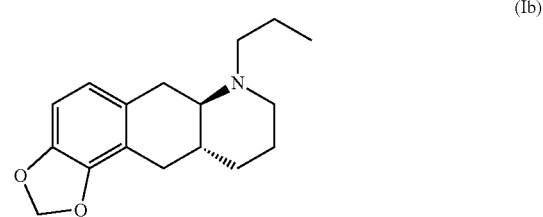 [SMILES: CCCN1CCC[C@@H]2Cc3c(ccc4c3OCO4)C[C@H]21]

(Ib)

The conversion of compound (Ib) to compound (I) in rat and human hepatocytes has been demonstrated in WO 2010/097092. Furthermore, the in vivo pharmacology of the compounds (Ia) and (Ib) as well as the active "parent compound" (I) has been tested in various animal models relevant for Parkinson's Disease (WO 2010/097092). Both compound (I) and compounds (Ia) and (Ib) were found to be effective, indicating that compounds (Ia) and (Ib) are converted in vivo to compound (I). All three compounds were reported to have a duration of action that was longer than observed for L-dopa and apomorphine.

The other prodrug of compound (I) disclosed in WO 2009/026934 and WO 2009/026935 is a conventional ester prodrug of the formula (Ic):

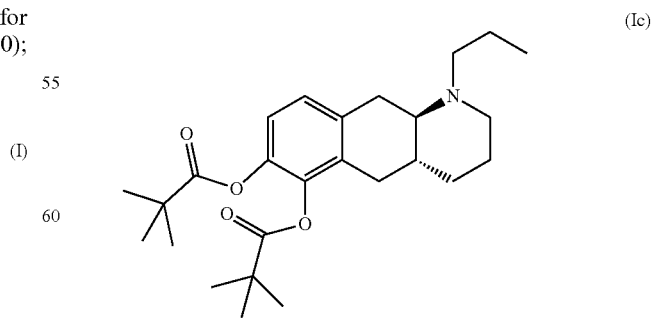

(Ic)

Despite the long-standing interest in the field, there is evidently still an unmet need as regards developing efficient, well-tolerated and orally active drugs for the treatment of PD. A prodrug derivative of a mixed D1/D2 agonist giving a stable PK profile which can provide continuous dopaminergic stimulation may fulfil such unmet needs.

Consequently, there is also a need for a process for manufacturing of such drugs, particularly processes that are suitable for large scale production and resulting in a high yield of the compound of formula (Id).

SUMMARY OF THE INVENTION

Surprisingly, it has been observed that oral dosing of (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid (compound (Id)) provides a systemic exposure of compound (I) in plasma, suggesting the usefulness of said compound as an orally active prodrug of compound (I). Examples 9 and 10 herein demonstrate the advantageous in vitro and in vivo effects of the compound (I) after dosing of compound (Id).

The present invention relates to a novel process for the manufacture of (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid with the formula (Id) below

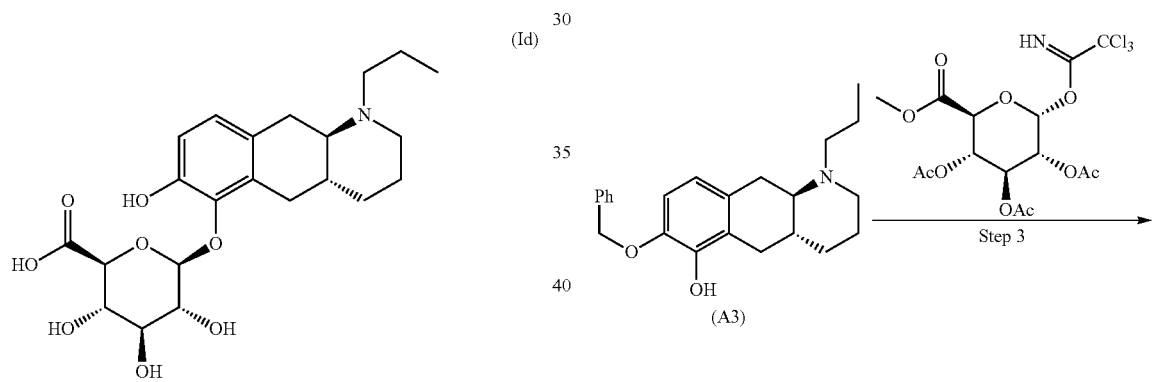

(Id)

from the compound (4aR,10aR)-1-Propyl-1,2,3,4,4a,5,10,10a-octahydro-benzo[g]quinoline-6,7-diol with the formula (I) below

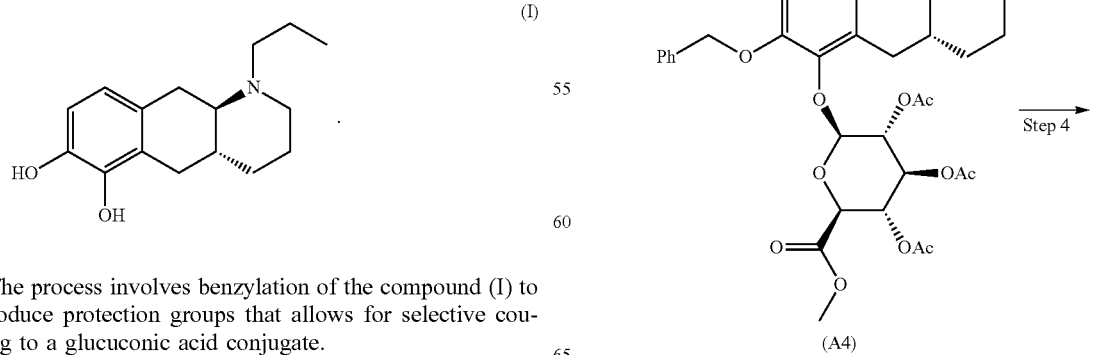

(I)

The process involves benzylation of the compound (I) to introduce protection groups that allows for selective coupling to a glucuconic acid conjugate.

The overall process starting from compound (I) is illustrated in brief in Scheme 1 below.

Scheme 1: Overview of overall process

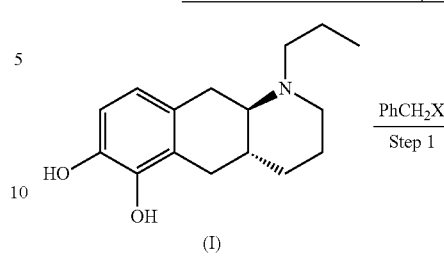

(I)

PhCH₂X
⟶
Step 1

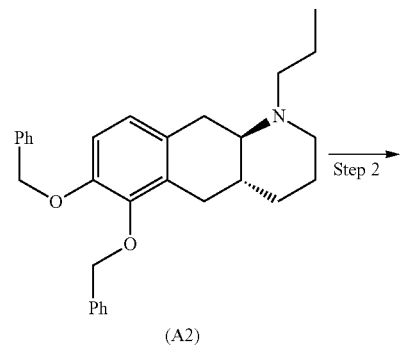

(A2)

Step 2
⟶

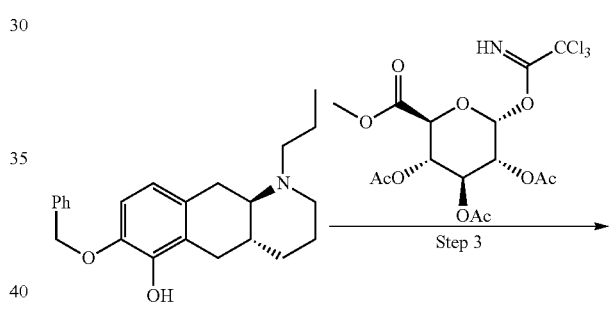

(A3)

Step 3
⟶

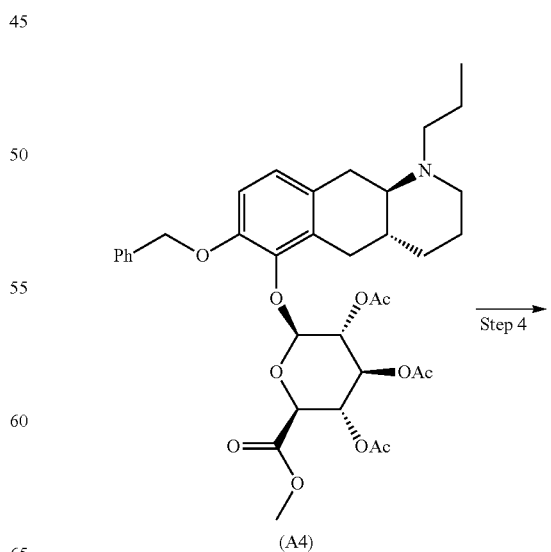

(A4)

Step 4
⟶

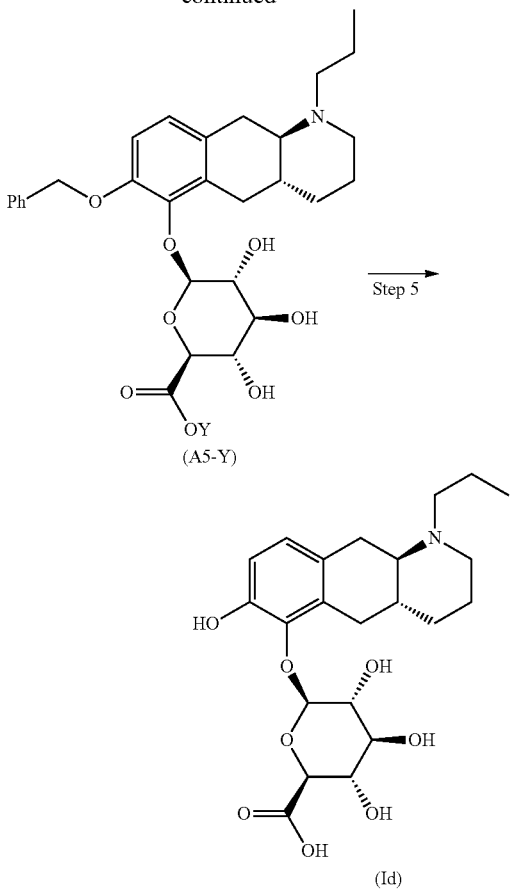

X is selected from the group consisting of Cl, Br and I.

Y is an alkali metal preferably selected from the group consisting of Li, Na and K.

In a specific embodiment of the invention, X is Cl.

In a specific embodiment of the invention, Y is K (potassium).

Individual aspects relate to each of the process steps 1), 2), 3), 4) and 5).

Other individual aspects of the invention relate to new intermediates of the process. Thus, further aspects of the present invention provide the compounds (A2), (A3), (A4) and (A5) and salts thereof respectively, which are useful intermediates in the processes for the manufacturing of the compound (Id).

The overall process, as well as each individual process step and intermediates as provided by the invention are useful for large scale production of compound (Id) and can be applied without, or while minimizing, use of column chromatography. Avoidance of column chromatography is advantageous, since it facilitates large scale production of the compound (Id).

Definitions

References to Compounds

References to compound (I), compound (Id), (A2), (A3), (A4) and (A5) include the compounds in solution and solid forms of the compounds including the free substance (zwitter ion) of said compounds, salts of said compounds, such as acid addition salts or base addition salts, and polymorphic and amorphic forms of compounds of the invention and of salts thereof. Furthermore, said compounds and salts thereof may potentially exist in unsolvated as well as in solvated forms with pharmaceutically acceptable solvents such as water, ethanol and the like. In an embodiment, the salt of compound (Id) is a pharmaceutically acceptable salt.

Sometimes, a specific salt form is indicated for a compound such as for example (A3-HI) which indicates the HI salt of (A3), or (A5-Y) which indicates an alkali salt of (A5) such as the potassium salt.

Pharmaceutically Acceptable Salts:

Pharmaceutically acceptable salts in the present context is intended to indicate non-toxic, i.e. physiologically acceptable salts.

The term "pharmaceutically acceptable salts" include pharmaceutically acceptable acid addition salts which are salts formed with inorganic and/or organic acids on the nitrogen atom in the parent molecule. Said acids may be selected from for example hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, malonic acid, fumaric acid, glutamic acid, pyroglutamic acid, salicylic acid, gentisic acid, saccharin, and sulfonic acids such as methanesulfonic acid, ethanesulfonic acid, toluenesulfonic acid, naphthalene-2-sulphonic acid, 2-hydroxy ethanesulphonic acid and benzenesulfonic acid.

The term pharmaceutically acceptable salts also include pharmaceutically acceptable base addition salts which are salts formed with inorganic and/or organic bases on the acidic groups of the compound of formula (Id). Said bases may be selected from for example zinc hydroxide, and alkali metal bases, such as sodium hydroxide, lithium hydroxide, potassium hydroxide, and alkaline earth bases, such as calcium hydroxide and magnesium hydroxide, and organic bases, such as choline, diethylamine, trimethylamine and triethylamine.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

Compounds (I), (A2), (A3), (A4), and (A5) may be used as intermediates for the manufacture of compound (Id)). Hence, the salt forms of the intermediates are not limited to pharmaceutically acceptable salts thereof. Nevertheless, pharmaceutically acceptable salts of the compounds (I), (A2), (A3), (A4), and (A5) can also advantageously be used in the manufacture of compound (Id) and compound (Ib). Hence, in an embodiment of the invention the salt of compound (I), (A2), (A3), (A4), (A5), and compound (Id) is a pharmaceutically acceptable salt.

Prodrug

In the present context, the terms "prodrug" or "prodrug derivative" indicates a compound that, after administration to a living subject, such as a mammal, preferably a human is converted within the body into a pharmacologically active moiety. The conversion preferably takes place within a mammal, such as in a mouse, rat, dog, minipig, rabbit, monkey and/or human. In the present context a "prodrug of the compound (4aR,10aR)-1-Propyl-1,2,3,4,4a,5,10,10a-octahydro-benzo[g]quinoline-6,7-diol" or "a prodrug of the compound of formula (I)" or "a prodrug of compound (I)" is understood to be a compound that, after administration, is converted within the body into the compound (4aR,10aR)-1-Propyl-1,2,3,4,4a,5,10,10a-octahydro-benzo[g]quinoline-6,7-diol. Said administration may be by any conventional route of administration of pharmaceutical compositions known in the art, preferably by oral administration.

In the present context, the terms "parent compound" and "parent molecule" indicate the pharmacologically active moiety obtained upon conversion of a corresponding prodrug. For example, the "parent compound" of the compound of formula (Id) is understood to be the compound of formula (I).

Pharmacokinetic Definitions and Abbreviations

As used herein, a "PK profile" is an abbreviation of "pharmacokinetic profile". Pharmacokinetic profiles and pharmacokinetic parameters described herein are based on the plasma concentration-time data obtained for the compound of formula (I) after oral dosing of the compound of formula (Id), using non-compartmental modelling. Abbreviated PK parameters are: $C_{max}$ (maximum concentration); $t_{max}$ (time to $C_{max}$); $t_{1/2}$ (half-life); AUC 0-24 (area under the curve from time of dosing and 24 hours after dosing), and "24 h exposure" is the concentration measured 24 hours after dosing.

Therapeutically Effective Amount:

In the present context, the term "therapeutically effective amount" of a compound means an amount sufficient to alleviate, arrest, partly arrest, remove or delay the clinical manifestations of a given disease and its complications in a therapeutic intervention comprising the administration of said compound. An amount adequate to accomplish this is defined as "therapeutically effective amount". Effective amounts for each purpose will depend e.g. on the severity of the disease or injury as well as the weight and general state of the subject.

In the context of the present invention, a "therapeutically effective amount" of the compound of formula (Id) indicates an amount of said compound of the invention that is able to provide an amount of compound (I) that is sufficient to alleviate, arrest, partly arrest, remove or delay the clinical manifestations of a given disease and its complications when said compound of the invention is administered, preferably by the oral route, to a mammal, preferably a human.

Treatment and Treating:

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

Conditions for Treatment:

The compound prepared by the process of the present invention is intended for treatment of neurodegenerative diseases and disorders such as Parkinson's disease and/or other conditions for which treatment with a dopamine agonist is therapeutically beneficial.

Therapeutic indications include a variety of central nervous system disorders characterized by motor and/or non-motor disturbances and for which part of the underlying pathophysiology is a dysfunction of the striatal-mediated circuitry. Such functional disturbances can be seen in neurodegenerative diseases such as but not limited to Parkinson's disease (PD), Restless leg syndrome, Huntington's disease, and Alzheimer's disease but also neuropsychiatric diseases such as, but not limited to schizophrenia, attention deficit hyperactivity disorder and drug addiction.

In addition to neurodegenerative diseases and disorders, other conditions in which an increase in dopaminergic turnover may be beneficial are in the improvement of mental functions including various aspects of cognition. It may also have a positive effect in depressed patients, and it may also be used in the treatment of obesity as an anorectic agent and in the treatment of drug addiction. It may improve minimal brain dysfunction (MBD), narcolepsy, attention deficit hyperactivity disorder and potentially the negative, the positive as well as the cognitive symptoms of schizophrenia.

Restless leg syndrome (RLS) and periodic limb movement disorder (PLMD) are alternative indications, which are clinically treated with dopamine agonists. In addition, impotence, erectile dysfunction, SSRI induced sexual dysfunction, ovarian hyperstimulation syndrome (OHSS) and certain pituitary tumors (prolactinoma) are also likely to be improved by treatment with dopamine agonists. Dopamine is involved in regulation of the cardiovascular and renal systems, and accordingly, renal failure and hypertension can be considered alternative indications for the compound of formula (Id).

The invention encompasses use of the compound of formula (Id) obtained by a process of the invention for treatment of the diseases and disorders listed above.

Administration Routes

Pharmaceutical compositions comprising a compound of formula (Id), either as the sole active compound or in combination with another active compound, may be specifically formulated for administration by any suitable route such as the oral, rectal, nasal, buccal, sublingual, pulmonal, transdermal and parenteral (e.g. subcutaneous, intramuscular, and intravenous) route. In the context of the present invention the oral route is the preferred route of administration.

It will be appreciated that the route will depend on the general condition and age of the subject to be treated, the nature of the condition to be treated and the active ingredient.

Pharmaceutical Formulations and Excipients

In the following, the term, "excipient" or "pharmaceutically acceptable excipient" refers to pharmaceutical excipients including, but not limited to, carriers, fillers, diluents, antiadherents, binders, coatings, colours, disintegrants, flavours, glidants, lubricants, preservatives, sorbents, sweeteners, solvents, vehicles and adjuvants.

The present invention also provides a pharmaceutical composition comprising the compound of formula (Id), such as one of the compounds disclosed in the Experimental Section herein. The present invention also provides a process for making a pharmaceutical composition comprising a compound of formula (Id). The pharmaceutical compositions according to the invention may be formulated with pharmaceutically acceptable excipients in accordance with conventional techniques such as those disclosed in Remington, "The Science and Practice of Pharmacy", $22^{th}$ edition (2013), Edited by Allen, Loyd V., Jr.

The pharmaceutical composition comprising a compound of the present invention is preferably a pharmaceutical composition for oral administration. Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses:

In one embodiment, compound (Id) prepared by a process of the invention is administered in an amount from about 0.0001 mg/kg body weight to about 5 mg/kg body weight per day. In particular, daily dosages may be in the range of 0.001 mg/kg body weight to about 1 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.01-100 mg/day of a compound of the present invention, such as 0.05-50 mg/day, such as 0.1-10 mg/day or 0.1-5 mg/day. Conveniently, the compounds of the invention are administered in a unit dosage form containing said compounds in an amount of about 0.01 to 50 mg, such as 0.05 mg, 0.1 mg, 0.2 mg, 0.5 mg, 1 mg, 5 mg, 10 mg, 15 mg, 20 mg or up to 50 mg of a compound of the present invention.

BRIEF DESCRIPTION OF FIGURES

FIG. 2: X-axis: time (min); Y-axis: Distance travelled (cm)±SEM/5-minute-bins.

FIG. 3: Y-axis: Total distance travelled (cm)±SEM. Significance levels for post-hoc comparisons (relative to the vehicle group) are indicated: *<0.05, <0.01, *<0.001, ****<0.0001.

X-axis time (min); Y-axis left: Distance travelled (cm) ±SEM/5-minute-bins; Y-axis right (FIG. 4): plasma concentration of compound (I) (pg/mL); Y axis right (FIG. 5): plasma concentration of apomorphine (ng/mL).

☐: Distance travelled (cm) ● plasma concentration.

Figure 6A:
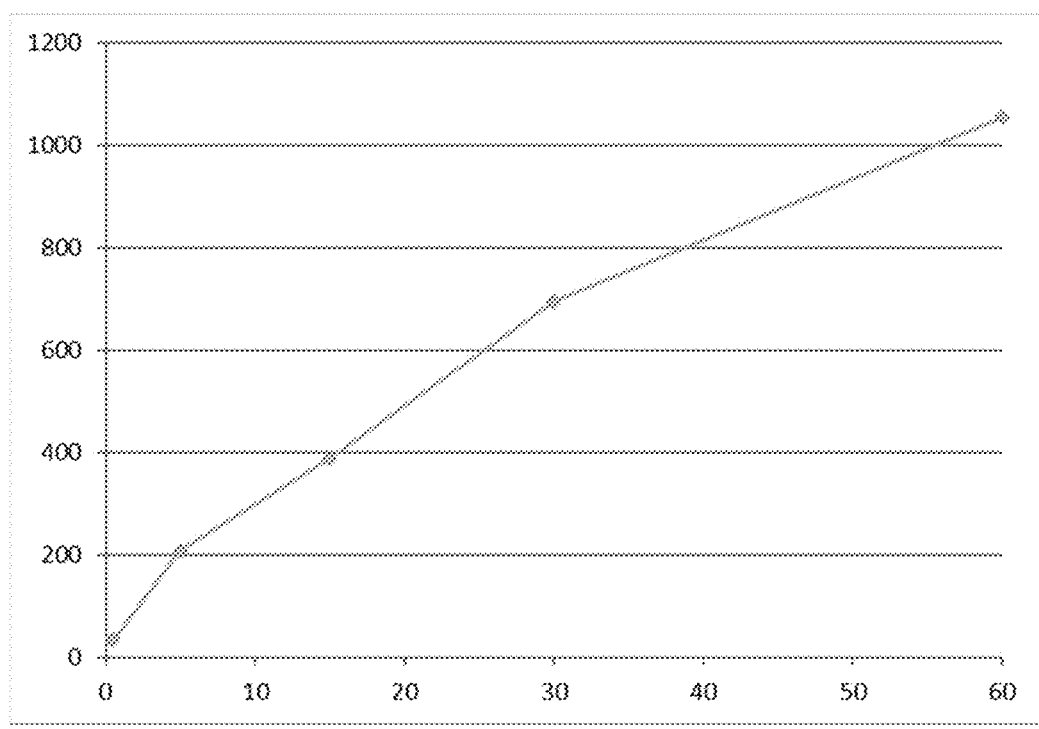
Figure 6B:
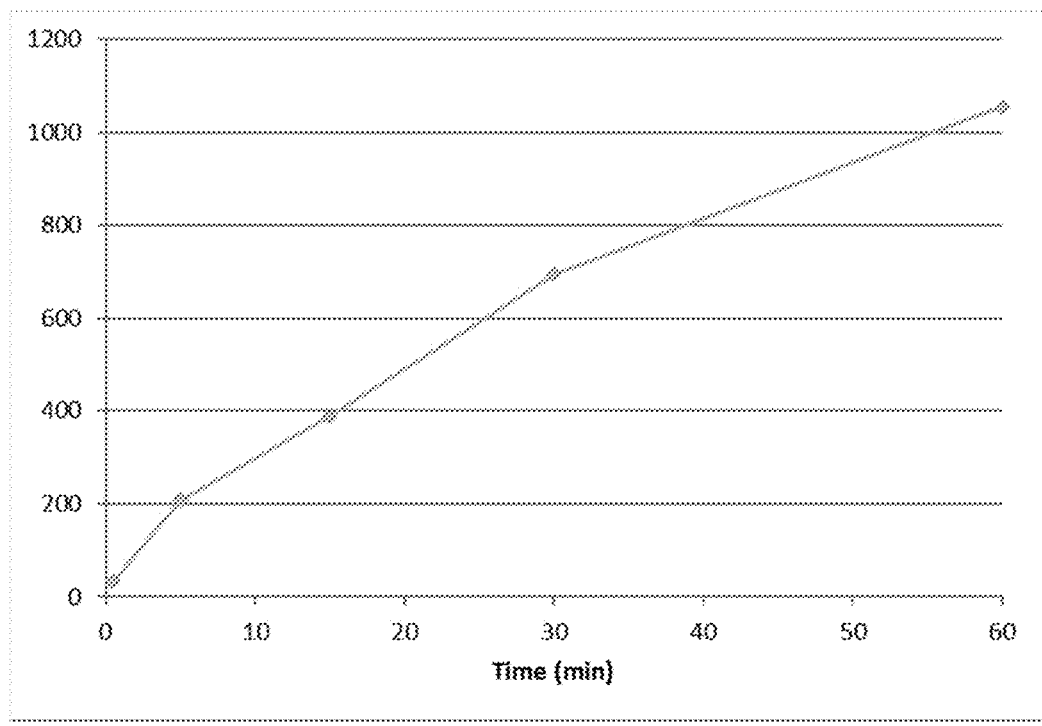

FIG. 6: conversion of compound (Id) to compound (I) in rat (6a) and human (6b) hepatocytes.

X-axis time (min); Y-axis: concentration of compound (I) (pg/mL).

Figure 7A:
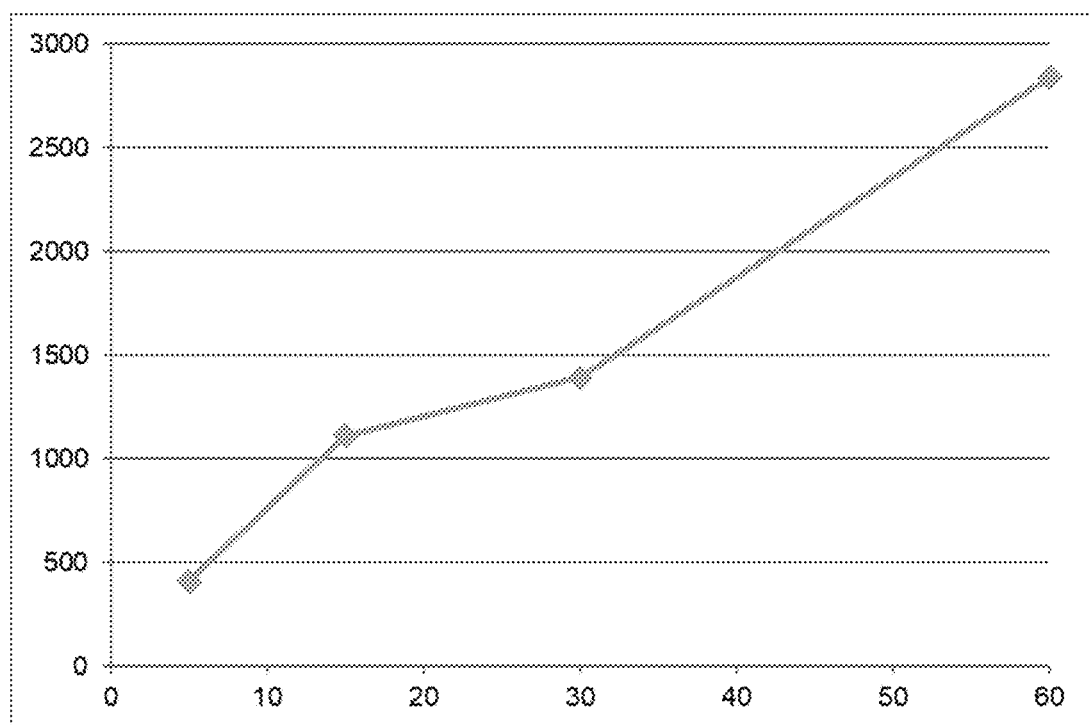
Figure 7B:
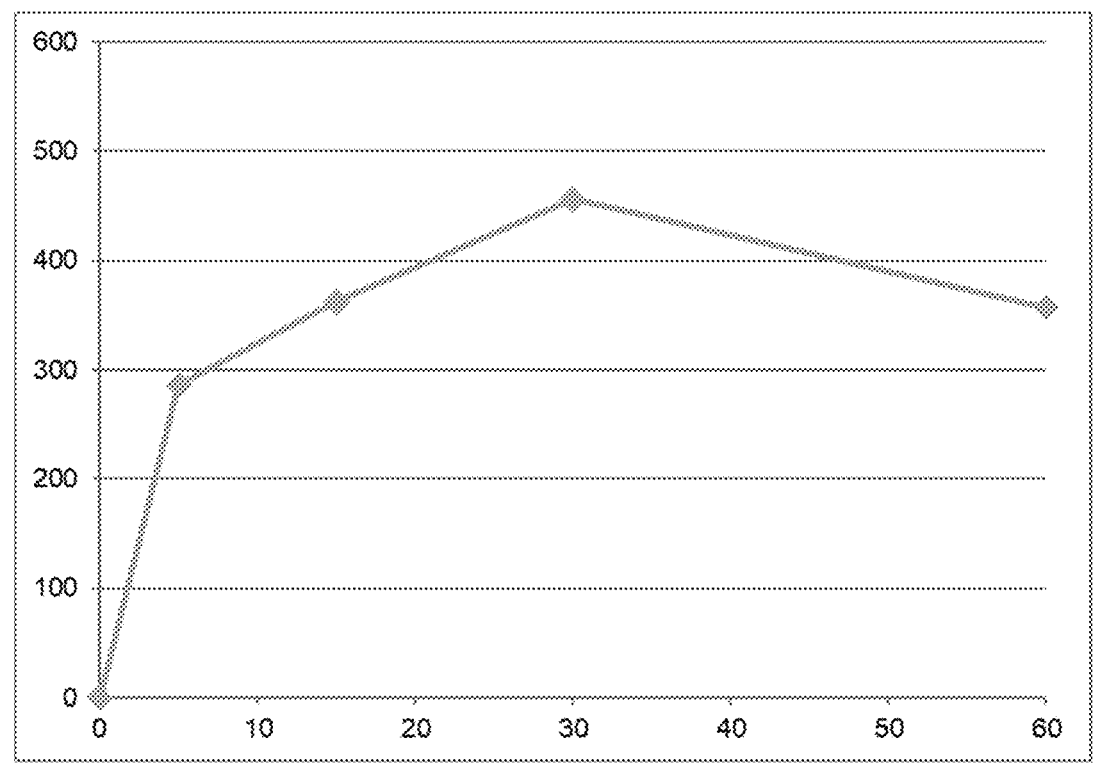

FIG. 7: conversion of compound (Id) in rat (7a) and human (7b) whole blood.

X-axis time (min); Y-axis: concentration of compound (I) (pg/mL).

DETAILED DESCRIPTION OF THE INVENTION

The present invention relates to a process for manufacturing the compound (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid with the formula (Id) below and salts thereof

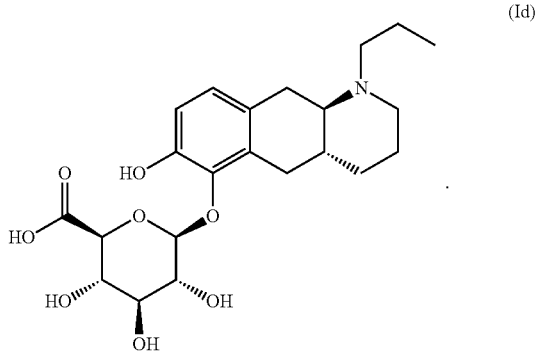 [SMILES: CCCN1CCC[C@@H]2Cc3c(ccc(O)c3O[C@@H]3O[C@H](C(=O)O)[C@@H](O)[C@H](O)[C@H]3O)C[C@H]21]

(Id)

The compound of formula (Id) is a prodrug of (4aR,10aR)-1-Propyl-1,2,3,4,4a,5,10,10a-octahydro-benzo[g]quinoline-6,7-diol [compound (I)] which is a dual D1/D2 agonist within vitro data listed in Table 2.

The inventors have observed that compound (I) is conjugated in rat and human hepatocytes to sulfate and glucuronide derivatives including compound (Id). The conjugates have shown to be converted to compound (I) by conjugation and de-conjugation in the body.

Glucuronide and sulfate derivatives are commonly known to be unstable in the intestine. The derivatives are formed as highly polar and soluble metabolites to facilitate the elimination of compounds from the body and are consequently easily excreted. For example, in bile duct cannulated rats, glucuronide and sulfate conjugates are often found in bile while their de-conjugate (i.e. the parent compound) is found in faeces. The back-conversion of glucuronide and sulfate conjugates in the intestine to the parent compound which is then sometimes subsequently reabsorbed, is known as part of the enterohepatic re-circulation process. As mentioned earlier, oral dosing of phenethyl catecholamines, such as apomorphine, has generally proven unsuccessful due to low bioavailability. Likewise, compound (I) suffers from low oral bioavailability (Liu et al., Bioorganic Med. Chem. (2008), 16: 3438-3444). With this in mind and considering the instability of glucuronide and sulfate conjugates in the gastrointestinal tract, it would not be expected that oral dosing of glucuronide and sulfate conjugates of compound (I) can be used to achieve sufficient plasma exposure of the compound.

The principle of applying glucuronide derivatives as prodrugs for oral delivery has been explored for retinoic acid (Goswami et al., J. Nutritional Biochem. (2003) 14: 703-709) and for morphine (Stain-Texier et al., Drug Metab. and Disposition (1998) 26 (5): 383-387). Both studies showed very low exposure levels of the parent compounds after oral dosing of the derivatives. Another study suggests the use of budenoside-β-D-glucuronide as a prodrug for local delivery of budenoside to the large intestine for treatment of Ulcerative Colitis based on poor absorption of the prodrug itself from the intestinal system (Nolen et al., J. Pharm Sci. (1995), 84 (6): 677-681).

Nevertheless, surprisingly, it has been observed that oral dosing of compound (Id) which has been identified as a metabolite of compound (I) in rats and minipigs provides a systemic exposure of compound (I) in plasma, suggesting the usefulness of said compound as an orally active prodrug of compound (I).

Figure 1:
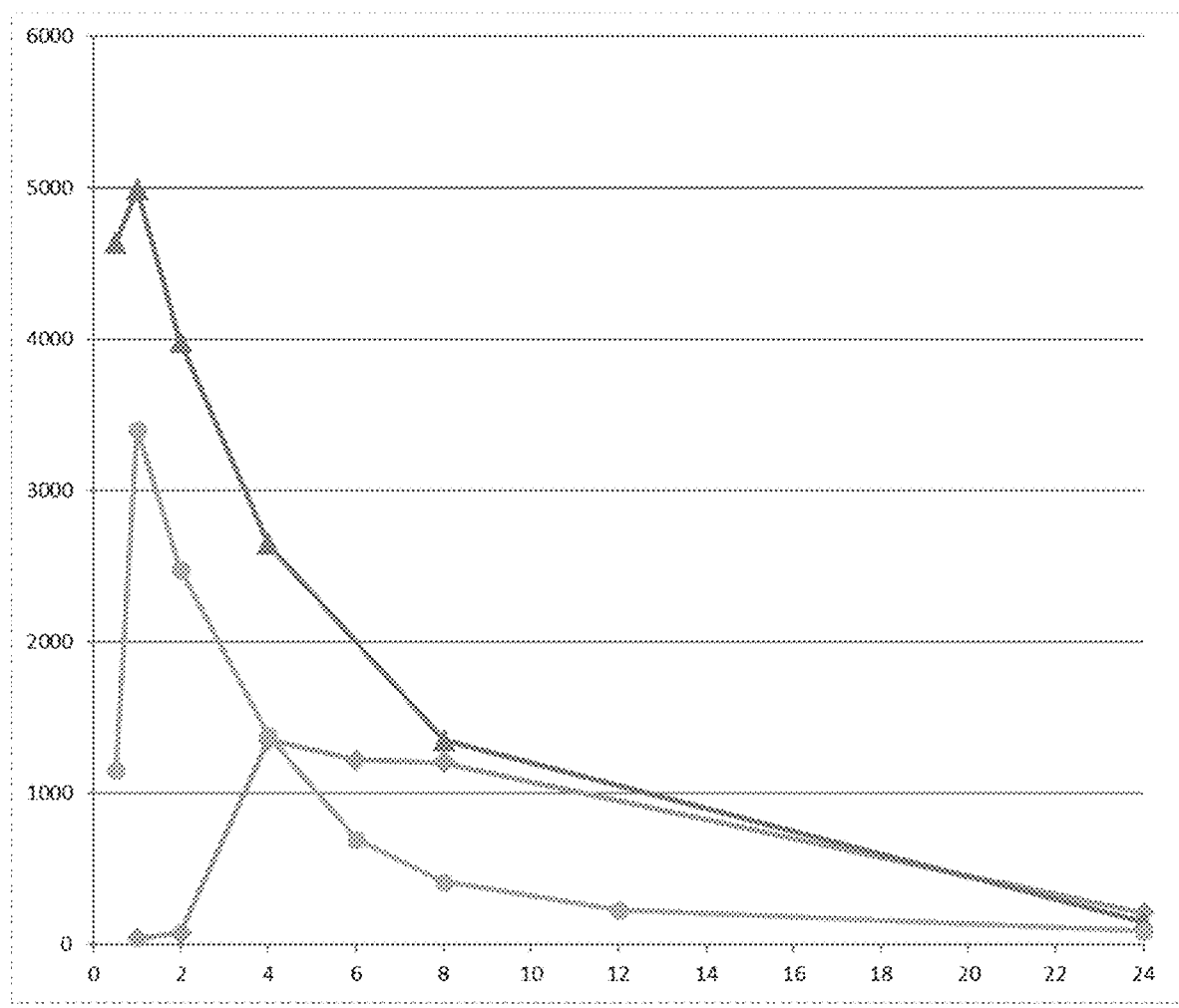
FIG. 1: PK profiles in Wistar rats obtained after oral dosing according to Example 9. Profiles are based on mean plasma concentrations from 3 subjects for each compound. X-axis: time (hours); Y-axis: plasma concentration of Compound (I) (pg/mL) obtained after dosing of the following compounds ●: compound (Ia); ▲: compound (Ib); ◆: compound (Id).

The plasma profile of compound (I) resulting from oral dosing of compounds (Ia) and (Ib) and compound (Id) to Wistar rats according to Example 9 are shown in FIG. 1. For all the compounds, the doses were corrected by molecular weight to equal a dose of 300 µg/kg of compound (Ib) corresponding to 287 µg/kg of compound (I). The inventors have found that oral dosing of compounds (Ia) and (Ib) to Wistar rats results in early and high peak concentrations of compound (I). Such high peak concentrations are in humans likely to be associated with dopaminergic side effects such as for example nausea, vomiting and light headedness. In contrast, dosing of the compound (Id), results in a slower absorption rate avoiding rapid peak concentrations accompanied by a sustained exposure of compound (I) in plasma. Additionally, the plasma exposure of compound (I) in Wistar rats is maintained throughout 24 hours although the obtained AUC of compound (I) is generally lower than the AUC obtained after dosing of compound (Ib). However, since the peak concentrations of compound (I) which are expected to drive the side effects are lower, higher doses might be administered of the compound (Id) to potentially achieve higher overall plasma concentrations of compound (I) compared to what is achievable from dosing compounds (Ia) and (Ib). When investigating PK properties of compound (Ic), the inventors found that the plasma concentrations of compound (I) were extremely low, leaving compound (Ic) unsuitable as a prodrug of compound (I) for oral administration and confirming that the oral bioavailability demonstrated for the compound of formula (Id) was highly unpredictable. PK parameters for the PK studies in Wistar rats are listed in Table 3.

In vivo conversion of compound (Id) to compound (I) has also been observed by after oral dosing of compound (Id) in minipigs.

Bioconversion of compound (Id) in human is supported by the Experiments of Example 6 indicating conversion to the compound of formula (I) in rat and human hepatocytes and in rat and human blood (FIGS. 6 and 7).

Thus, in conclusion, the compound of formula (Id) is useful as an orally active prodrug of compound (I) and has been observed in rats to provide a PK profile avoiding the peak $C_{max}$ observed for the known prodrugs (Ia) and (Ib) and providing a significantly higher AUC of compound (I) than compound (Ic).

Figure 2:
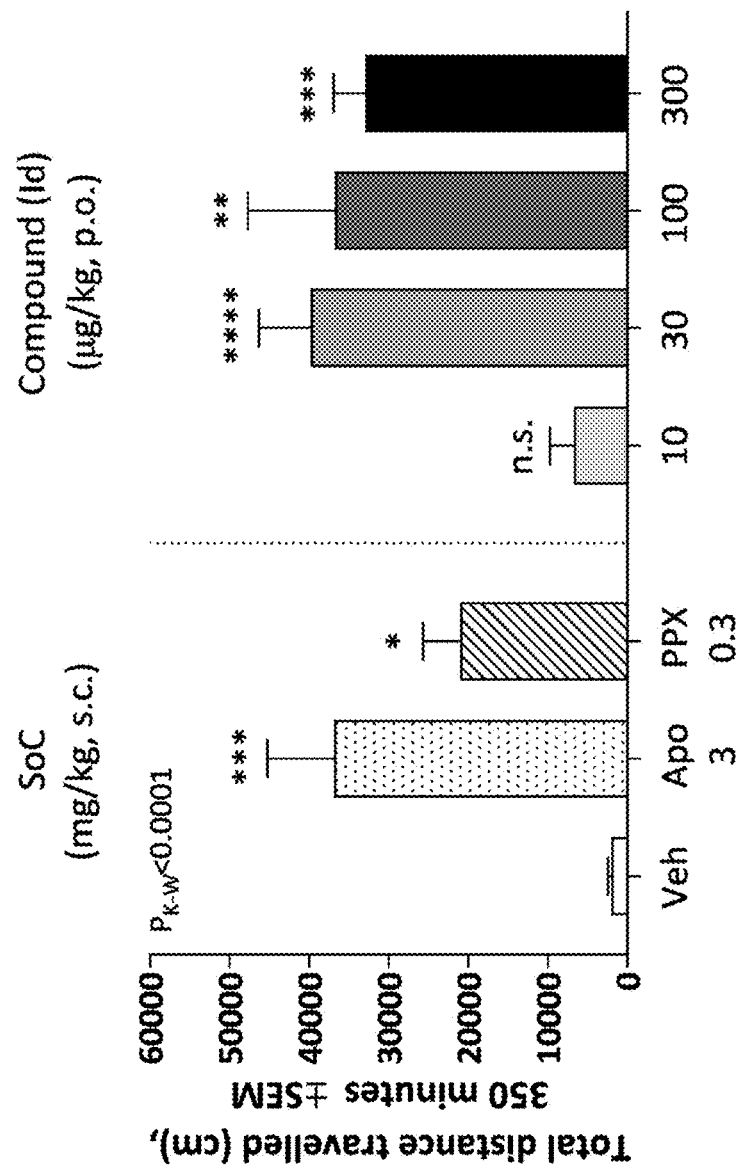
FIGS. 2 and 3: Locomotor activity time-course (FIG. 2) and total distance travelled (FIG. 3) following treatment with vehicle ($H_2O$, p.o.), or compound (Id) (10, 30, 100 or 300 µg/kg, p.o.) and compared to standard-of-care (SoC) treatments: apomorphine (APO, 3 mg/kg, s.c.), pramipexole (PPX, 0.3 mg/kg, s.c.). Animals were dosed at t=60 minutes after a 60-min. habituation period in test chambers, and activity was monitored for 350 minutes thereafter. Data was evaluated by use of a Kruskal-Wallis test with Dunn's Multiple Comparisons test, resulting in an overall P-value of <0.0001.
Figure 3:
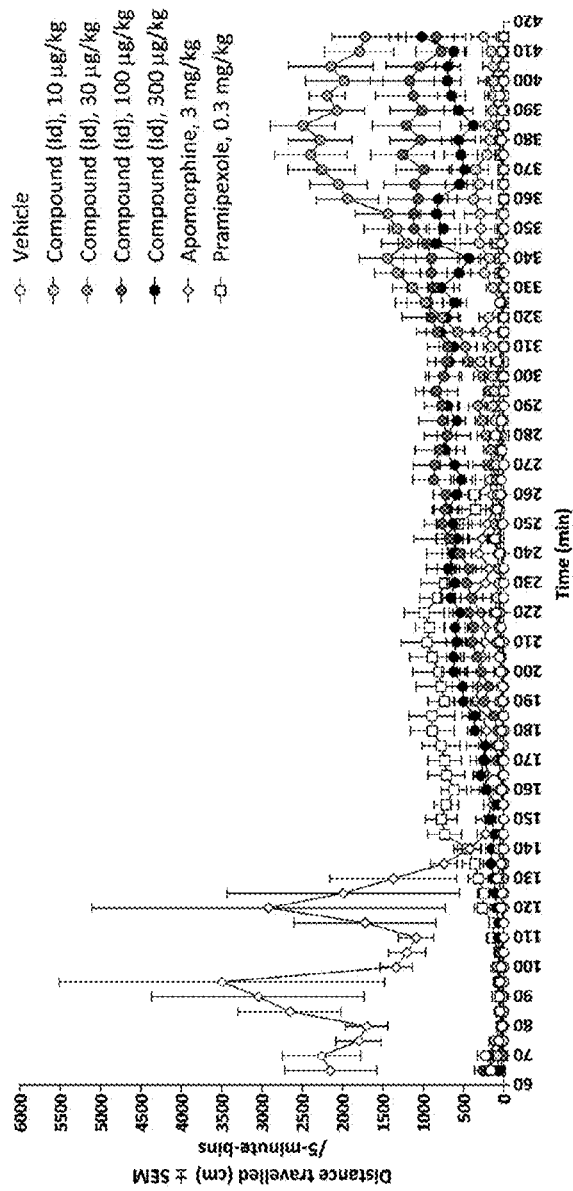
Figure 4:
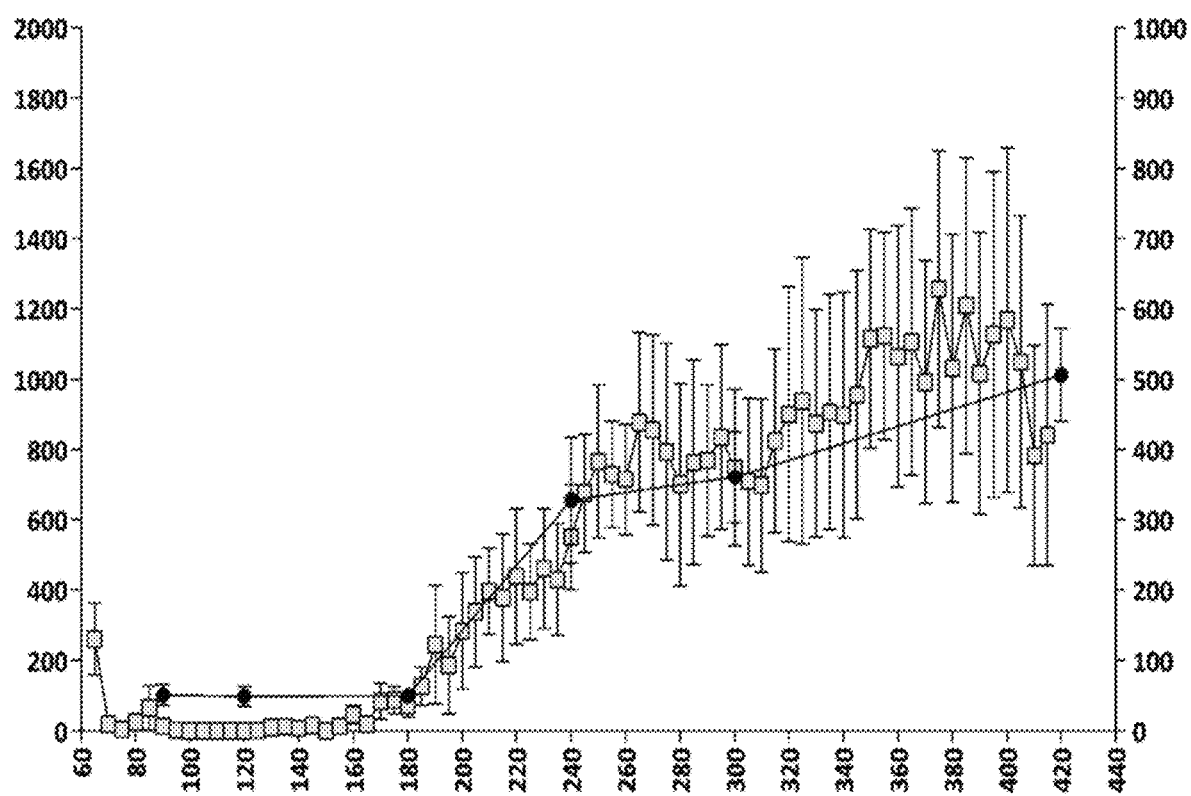
FIGS. 4 and 5: Relationships between plasma concentrations of compound (Id) and compound (I) and hyperactivity induced by compound (Id) (100 µg/kg, p.o.) (FIG. 4) and the corresponding relationship between plasma apomorphine concentrations and hyperactivity induced by apomorphine (3 mg/kg, s.c.) (FIG. 5).
Figure 5:
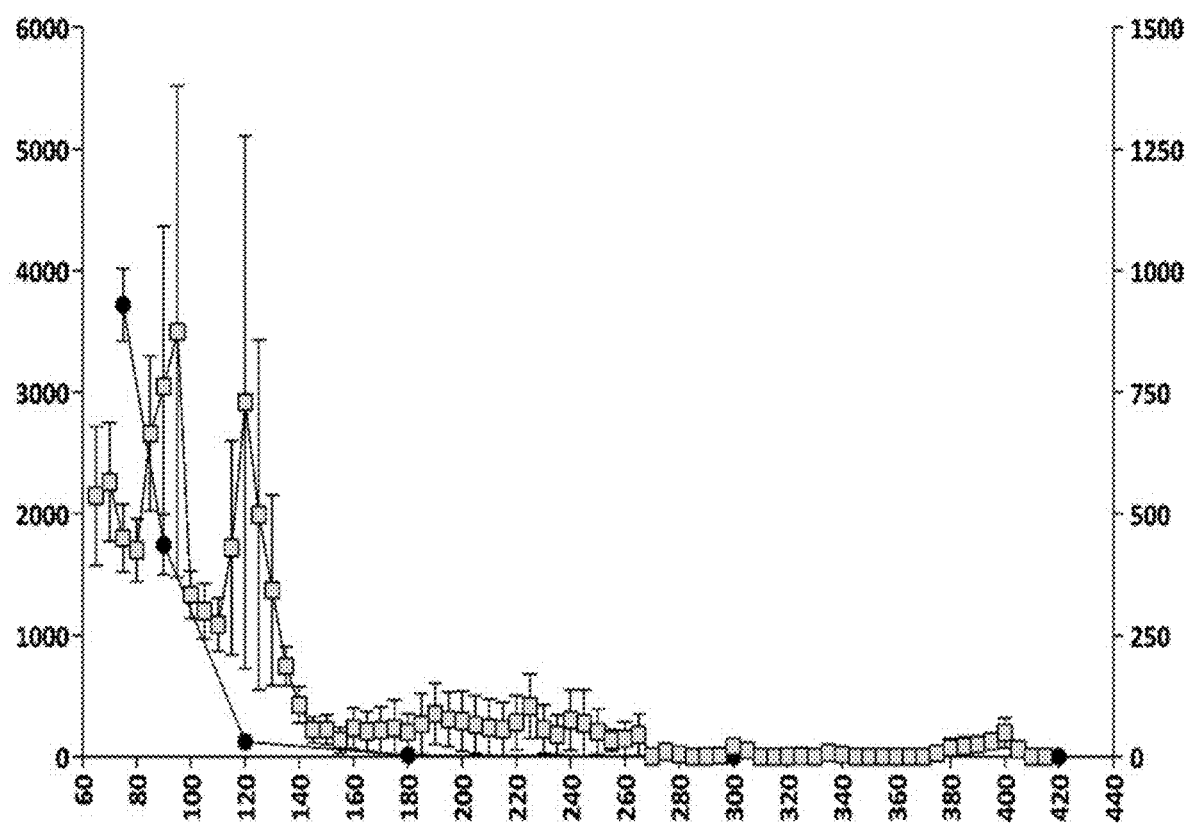

Compound (Id) has further been explored in the rat locomotor activity assay according to Example 10. The assay demonstrated a dopaminergic effect obtained after oral administration of compound (Id) c.f. FIGS. 2, 3 and 4. The fact that the compound of formula (Id) possesses no in vitro dopaminergic activity c.f. example 9 and Table 3, further indicates that the effect of compound (Id) in the rat locomotor activity assay is obtained by conversion of compound (Id) to compound (I).

Finally, an important issue associated with the prior art compound (Ib) is that this compound is an agonist of the 5-HT2B receptor. Since 5-HT2B receptor agonists have been linked to pathogenesis of valvular heart disease (VHD) after long term exposure, such compounds are not suitable for use in the treatment of chronical diseases (Rothman et al., Circulation (2000), 102: 2836-2841; and Cavero and Guillon, J. Pharmacol. Toxicol. Methods (2014), 69: 150-161). Thus, a further advantage of the compounds of the invention is that these are not 5-HT2B agonists c.f. example 8 and Table 2.

The compound of formula (Id) is useful in the treatment of neurodegenerative diseases and disorders such as Parkinson's disease and/or other conditions for which treatment with a dopamine agonist is therapeutically beneficial. The compound, being suitable for oral administration has the potential of providing a new treatment paradigm in Parkinson's Disease.

The invention provides a scalable synthesis of compound (Id), which may avoid column chromatographic purification, while providing compound (Id) in high purity. The overall process starting from compound (I) is illustrated in brief in Scheme 2 below.

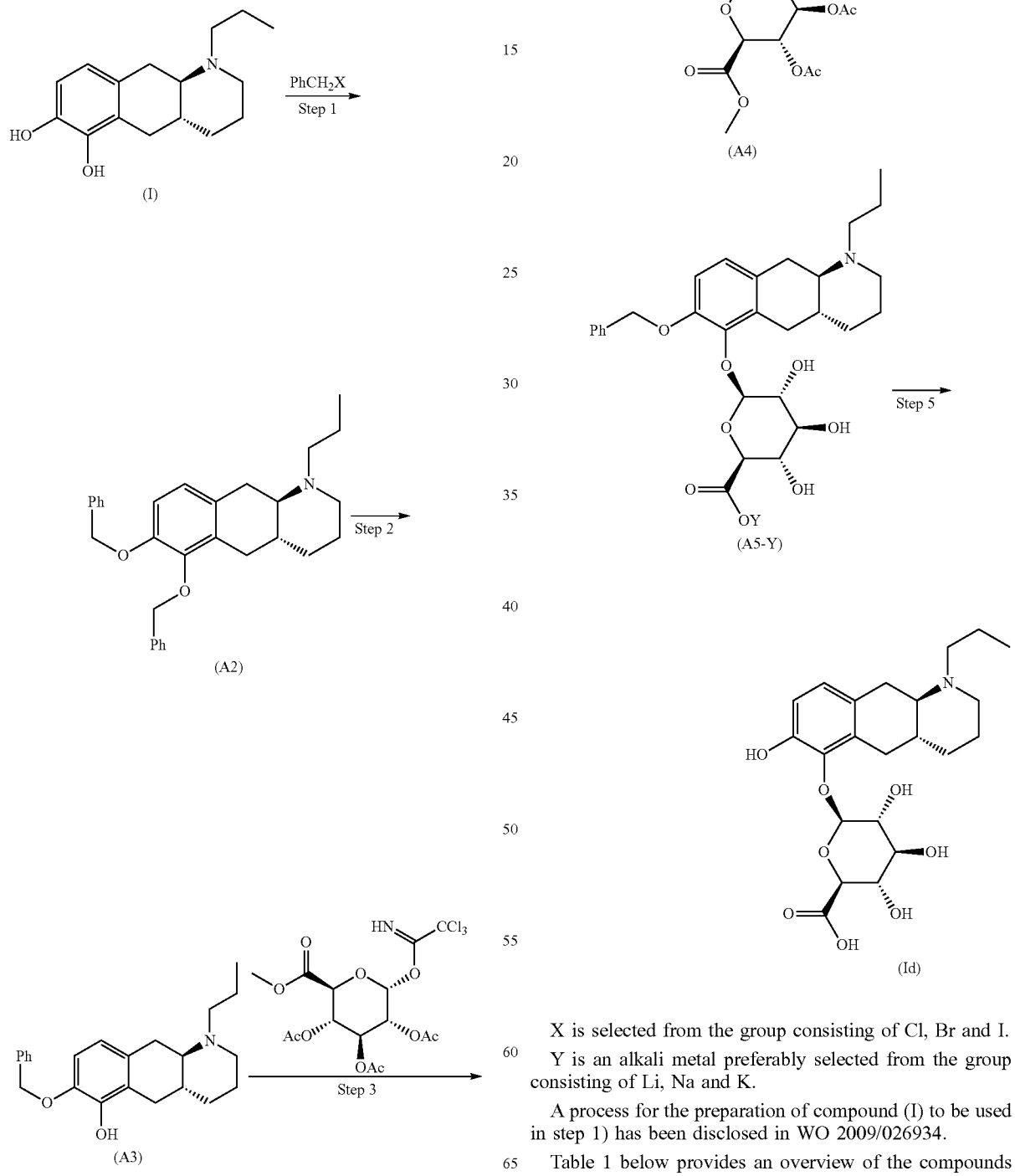

X is selected from the group consisting of Cl, Br and I.

Y is an alkali metal preferably selected from the group consisting of Li, Na and K.

A process for the preparation of compound (I) to be used in step 1) has been disclosed in WO 2009/026934.

Table 1 below provides an overview of the compounds (A2), (A3), (A4) and (A5) which are intermediates with the following respective compound names.

TABLE 1

Overview of intermediates

| Abbreviated name | Chemical name | Structure drawing |
| --- | --- | --- |
| (A2) | (4aR,10aR)-6,7-bis(benzyloxy)-1-propyl-1,2,3,4,4a,5,10,10a-octahydrobenzo[g]quinoline; | (A2) |
| (A3) | (4aR,10aR)-7-(benzyloxy)-1-propyl-1,2,3,4,4a,5,10,10a-octahydrobenzo[g]quinolin-6-ol | (A3) |
| (A3-HI) | hydroiodide salt of compound (A3) | (A3-HI) |
| (A4) | (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate | (A4) |

TABLE 1-continued

Overview of intermediates

| Abbreviated name | Chemical name | Structure drawing |
|---|---|---|
| (A5) | (2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-trihydroxytetrahydro-2H-pyran-2-carboxylic acid | (A5) |
| (A5-Y) | alkali salt of compound (A5) | (A5-Y) |

The reactant (2S,3S,4S,5R,6R)-2-(methoxycarbonyl)-6-(2,2,2-trichloro-1-iminoethoxy)tetrahydro-2H-pyran-3,4,5-triyl triacetate, used in step 3, can be purchased at Sigma-Aldrich (CAS Number: 92420-89-8).

Step 1

In step 1) the inventors found that compound (I), surprisingly could be subjected to a dibenzylation reaction with benzyl halogenide such as for example benzyl chloride or benzyl bromide affording compound (A2), without significant loss to quaternization of the tertiary amine moiety. There are examples of dibenzylations of 3-alkyl substituted catechols reported, in which there are no electron-withdrawing groups attached directly to the aromatic ring of the catechol, while no examples have been reported with the additional structural presence of an unprotected amine. Loev, B et al (*JACS*, 1956, 78, p. 6095-6097), Imai, K. et al (*RSC Adv.*, 2017, 7, 17968-17979), Mandell, L. et al (*J. Org. Chem.*, 1982, 47, 731-734), Loozen, B. et al. (*Recueil des Travaux Chimiques des Pays Bas*, 1982, 101, 298-310), Montanari, S. et al. (U.S. Pat. No. 5,747,513, 1998, A), and Shimada, X. et al. (*Chemical and Pharmaceutical Bulletin*, 1986, 34, 179-187) reported dibenzylation using benzyl bromide in DMF, acetone, or EtOH with potassium carbonate as base, purifying the product using silica gel column chromatography.

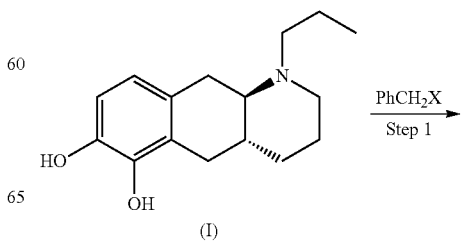

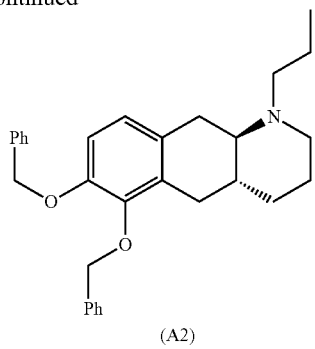

(A2)

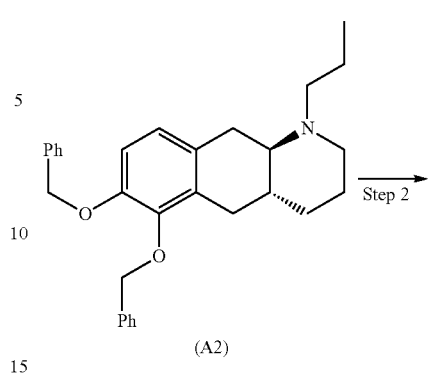

(A2)

X is selected from Cl, Br and I

The reaction occurs in an organic solvent preferably selected from acetonitrile (MeCN), dimethylformamide (DMF) or methyl isobutyl ketone (MIBK) in the presence of a base, preferably an inorganic base such as for example sodium or potassium hydroxide (NaOH or KOH) or potassium carbonate ($K_2CO_3$).

Step 2

Step 2) is a selective deprotection and there are only a few examples of selective mono debenzylations of a 3-substituted dibenzylated catechol reported. Hitoshi, T et al. (*Chem Pharm Bull*, 1986, 628) reported a selective debenzylation using trifluoroacetic acid (TFA, 86:7 ratio of regio-isomers, 86% yield) or aluminum trichloride ($AlCl_3$, 85:7 ratio of regio-isomers, 85% yield) in benzene and aluminum tribromide ($AlBr_3$) in nitrobenzene (80% yield, one regio-isomer) or carbon disulfide (78% yield, one regio-isomer). The large scale use of solvents such as benzene, nitrobenzene, and carbon disulfide are not recommended, due to carcinogenic and toxicological characteristics. The use of trifluoroacetic acid is optimal due to environmental concerns and aluminum trichloride and aluminum tribromide, both would require aqueous workup at neutral or basic pH, which is unfavourable in regards to stability and isolation of (A3). Montanari, S. et al. (U.S. Pat. No. 5,747,513) reported using trimethylsilyl iodide (TMSI) in dichloromethane and purifying the crude product using silica gel column chromatography. The use of silica gel column chromatography in isolation and purification limits the scalability of the process. The current invention describes a scalable process in which mono-debenzylation may be achieved with high selectivity (>99:1) in the presence of an unprotected amine.

In a preferred embodiment, the HI salt of (A3) is directly isolated as a stable solid. The isolation of the HI salt of compound (A3) as a solid allows for a high yield, thus avoiding tedious purification using silica gel column chromatography.

In summary, step 2 provides a scalable and selective mono-debenzylation of compound (A2), mediated by a debenzylation agent such as trimethylsilyl iodide resulting selectively in a high yield of compound (A3), which may be isolated as a hydroiodide salt (A3-HI).

(A3-HI)

The reaction is preferably performed under nitrogen atmosphere in an organic solvent such as for example acetonitrile (MeCN), dichloromethane, or chloroform ($CHCl_3$). The compound is directly obtained as the hydroiodide salt in high purity without the use of column chromatography.

Step 3

In step 3) compound (A3) is coupled with (2S,3S,4S,5R,6R)-2-(methoxycarbonyl)-6-(2,2,2-trichloro-1-iminoethoxy)tetrahydro-2H-pyran-3,4,5-triyl triacetate in an organic solvent, such as for example dichloromethane or (trifluoromethyl)benzene, promoted by a protic acid such as trifluoromethanesulfonic acid or a Lewis acid and protic acid combination such as boron trifluoride diethyl etherate and hydroiodide to obtain compound (A4).

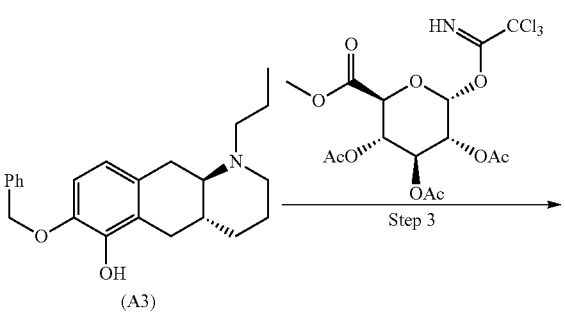

(A3)

-continued

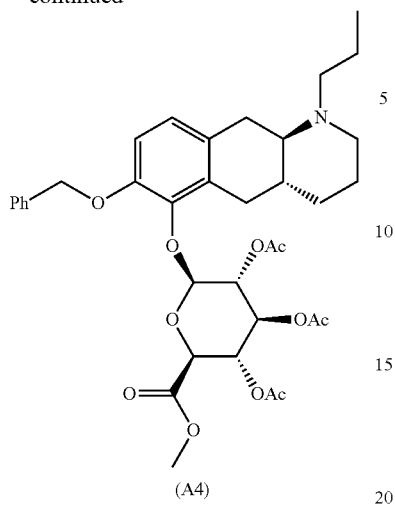

(A4)

A further challenge is the removal of the excess sugar residues without the use of column chromatography. Column chromatography can be avoided by extracting the product into a solution with a pH between 1-5, such as between 2-4, such as between 2.5-3.5, such as between 2.7-3.2 such as about 3. Optimal pH conditions can be obtained by for example extracting the product into a solution of an acid with pKa between 2-4, such as between 2.5-3.5, such as between 2.7-3.2, such as about 3; such as for example a citric acid solution.

Thereby the sugar residues can be removed and followed by pH neutralization of the solution compound (A4) can be isolated.

Step 4

In step 4) compound (A4) is taken directly further for the deprotection of the sugar moiety followed by precipitation of a salt of compound (A5) such as an alkali salt, preferably a potassium salt.

-continued

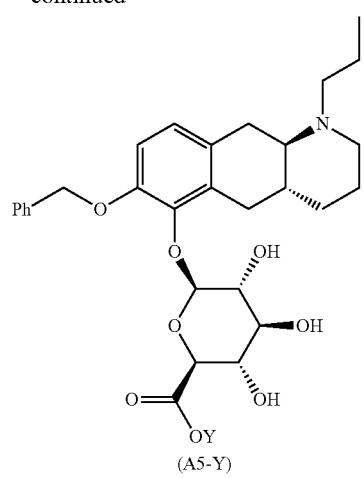

(A5-Y)

Y is an alkali metal preferably selected from Li, Na and K

The inventors found that by precipitation of the compound as the potassium salt from an aqueous solution the compound could be isolated via filtration and obtained in high purity. Glucuronic acid conjugates are typically very water soluble (Stachulski, A. V. et al. *Nat. Prod. Rep.*, 2013, 30, 806-848), it is therefore surprising that A5 precipitates as potassium salt directly from water, thereby isolating A5 without the use of reverse phase column chromatography in high purity.

Step 5

In step 5) compound (A5-Y) is debenzylated to afford compound (Id).

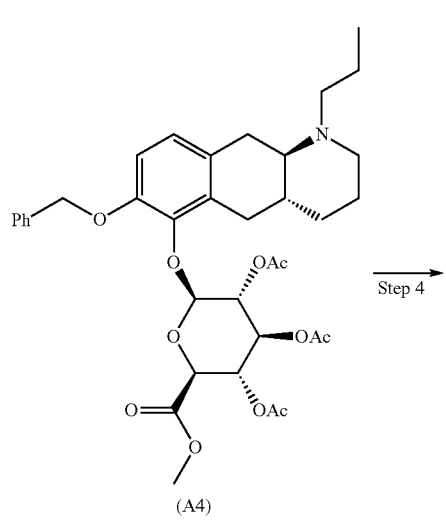

(A4)

Step 4 →

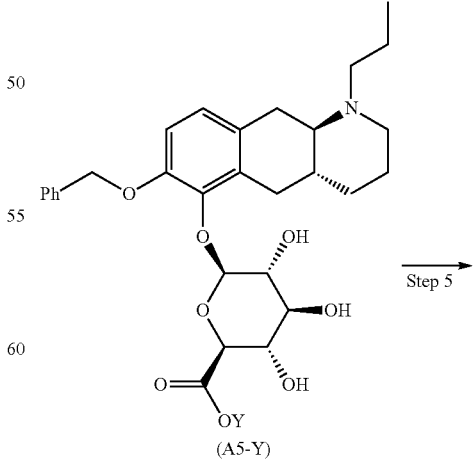

(A5-Y)

Step 5 →

-continued

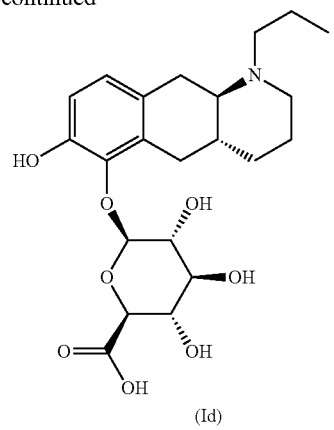
(Id)

Debenzylation can be performed by hydrogenation in water e.g. in the presence of Pd/C and hydrogen. The end product can be isolated via filtration and neutralized with an acid such as for example HCl, thereby affording compound (Id) as a heptahydrate.

Embodiments of the Invention

In the following, embodiments of the invention are disclosed. The first embodiment is denoted E1, the second embodiment is denoted E2 and so forth.

E1. A process for the preparation of compound (Id), or a pharmaceutically acceptable salt thereof with the formula below

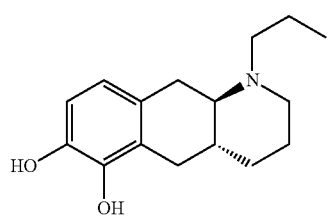
(Id)

from compound (I), or a salt thereof with the formula below

(I)

comprising the following step
1) reacting compound (I), or a salt thereof with benzyl halogenide to obtain compound (A2) according to the reaction scheme below

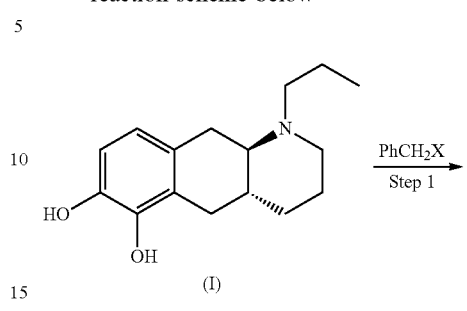

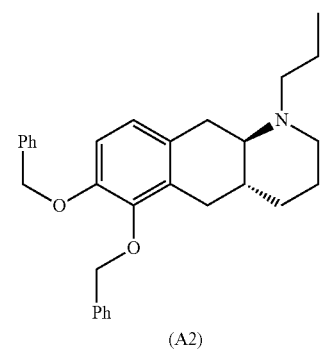
(A2)

wherein is selected from Cl, Br and I.

E2. A process for the manufacturing the compound of formula (A2) below comprising the following step
1) reacting compound (I), or salt thereof with benzyl halogenide to obtain compound (A2) according to the reaction scheme below

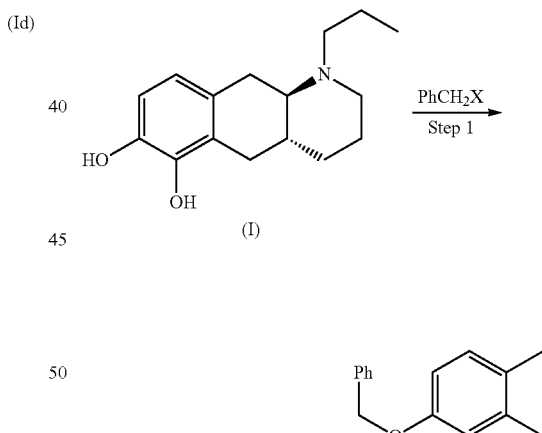

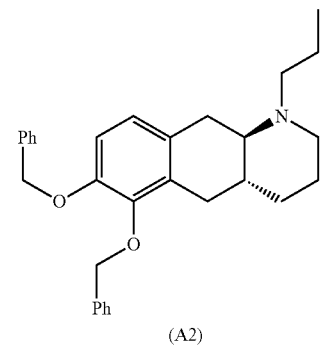
(A2)

wherein X is selected from Cl, Br and I.

E3. The process according to any of embodiments 1-2, wherein:
 a) said benzyl halogenide is benzyl chloride and X is Cl; or
 b) said benzyl halogenide is benzyl bromide and X is Br.

E4. The process according to any of embodiments 1-3, wherein said reaction takes place in an organic solvent such as for example acetonitrile (MeCN), dimethylformamide (DMF) or methyl isobutyl ketone (MIBK); and in the presence of a base such as for example sodium or potassium hydroxide (NaOH or KOH) or potassium carbonate (K$_2$CO$_3$).

E5. The process according to any of embodiments 1-4, wherein compound (I) is in the form of the HCl salt as shown below

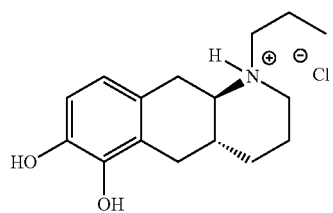

(I)

E6. The compound of formula (A2) below:

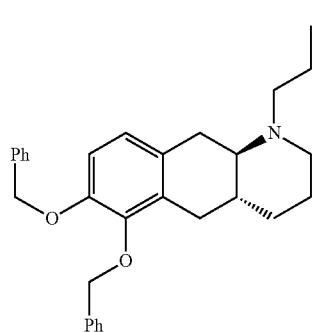

(A2)

or a salt thereof.

E7. Use of a compound according to embodiment E6, in a process for the manufacture of the compound of formula (Id).

E8. A process for the preparation of compound (Id) with the formula below

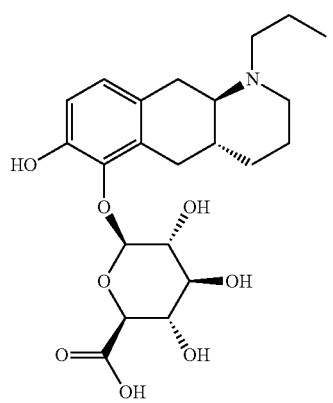

(Id)

from compound (I) with the formula below

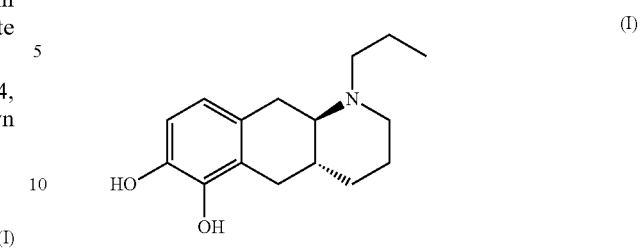

(I)

comprising the following step
2) subjecting compound (A2) to a dibenzylation reaction to obtain compound (A3), or a salt thereof according to the reaction scheme below

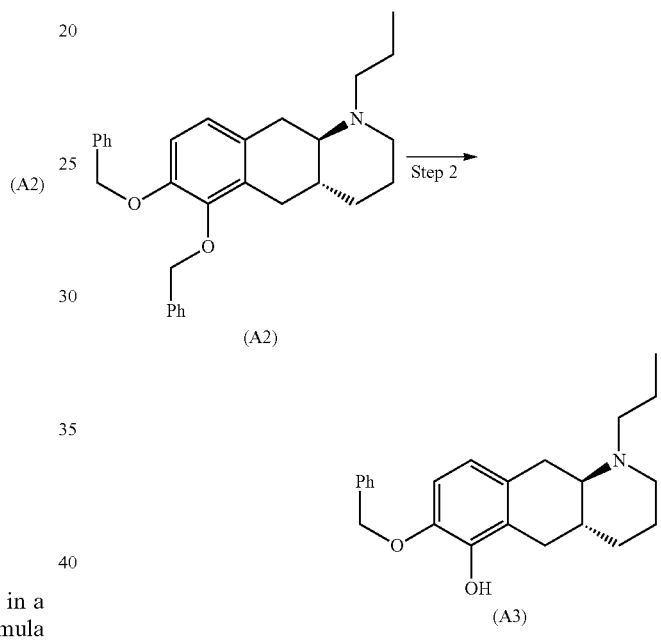

(A2)

E9. The compound of formula A3 below:

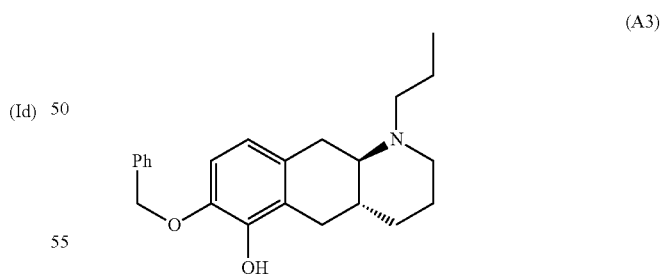

(A3)

or a salt thereof.

E10. The process according to embodiment 8, wherein the dibenzylation reaction comprises the steps of:
I) reacting trimethylsilyl iodide with compound (A2) to form a mixture;
II) adding an alcohol to said mixture obtained from step 1) to obtain compound (A3) or a salt thereof;
III) optionally isolating compound (A3) or a salt thereof.

E11. The process according to embodiment 10, wherein the alcohol added to said mixture in step II) is MeOH or n-heptyl alcohol.

E12. The process according to embodiments 10 to 11, wherein compound (A3) is obtained in the form of a hydroiodide salt (A3-HI).

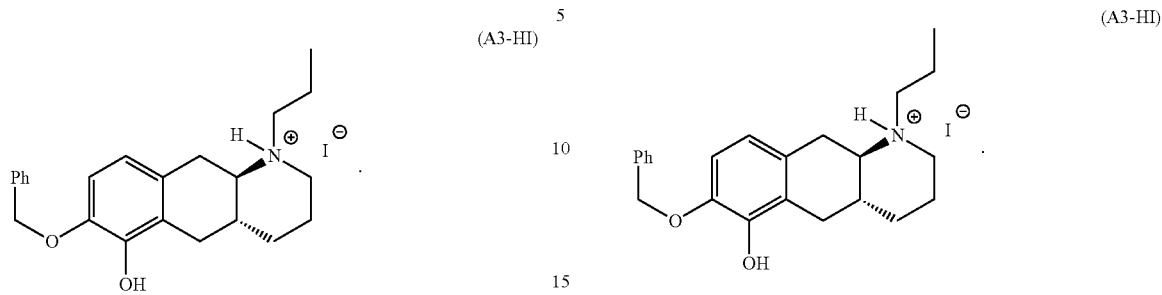

(A3-HI)

E13. A process for the manufacture of the compound of formula (A3-HI) below, comprising the following step
2) reacting compound (A2) with trimethylsilyl iodide to obtain compound (A3-HI)

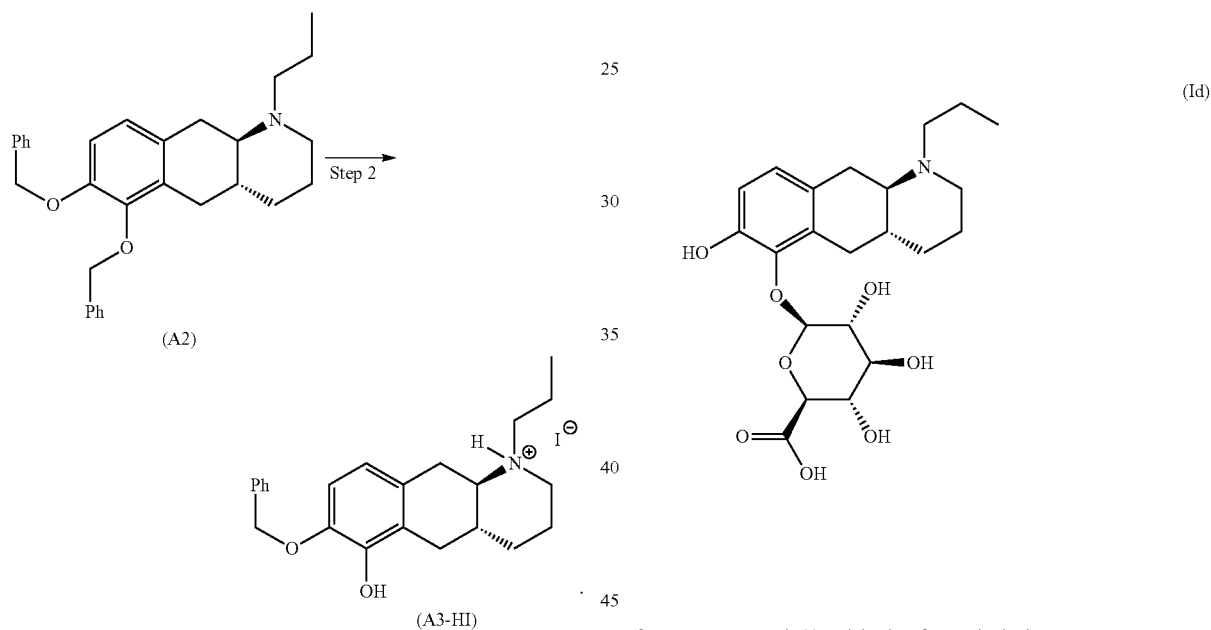

E14. The process according to any of embodiments 8-13, wherein said reaction takes place under nitrogen atmosphere in an organic solvent such as for example acetonitrile (MeCN), dichloromethane (CH$_2$Cl$_2$), or chloroform (CHCl$_3$).

E15. The compound of formula A3 below:

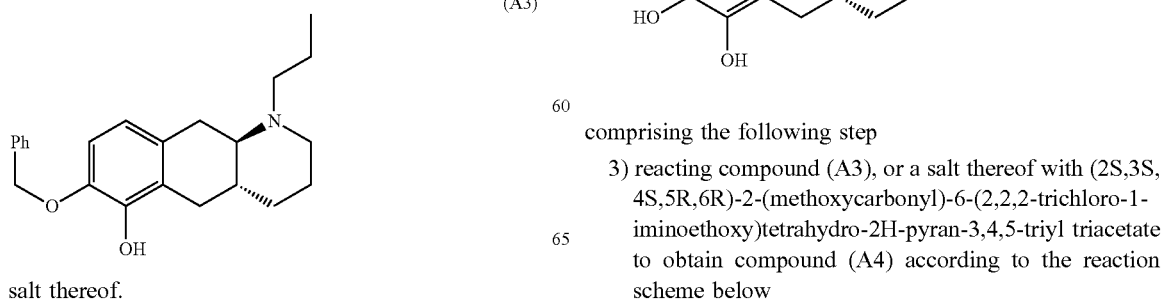

(A3)

or a salt thereof.

E16. The compound according to embodiment 15 which is in the form of a hydroiodide salt depicted below (A3-HI)

E17. Use of a compound according to any of embodiments 15-16 in a process for the manufacture of compound (Id).

E18. A process for the preparation of compound (Id) with the formula below (Id)

from compound (I) with the formula below (I)

comprising the following step
3) reacting compound (A3), or a salt thereof with (2S,3S, 4S,5R,6R)-2-(methoxycarbonyl)-6-(2,2,2-trichloro-1-iminoethoxy)tetrahydro-2H-pyran-3,4,5-triyl triacetate to obtain compound (A4) according to the reaction scheme below

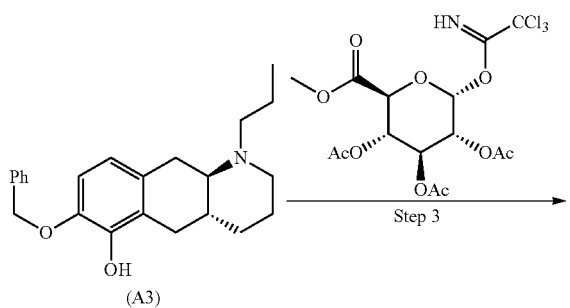

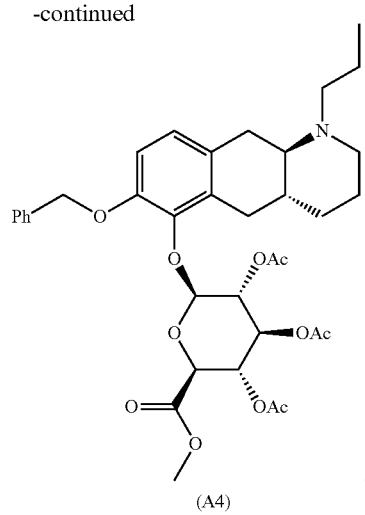

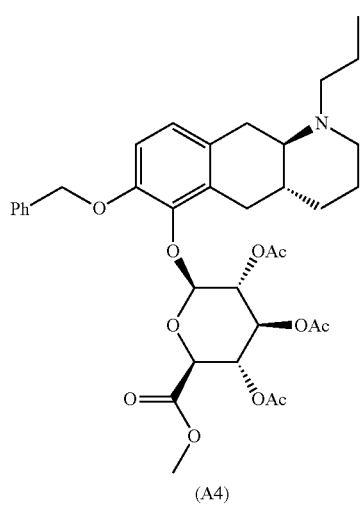

E19. A process for the manufacture of the compound of formula (A4) below, comprising the following step 3) reacting compound (A3), or a salt thereof with (2S,3S,4S,5R,6R)-2-(methoxycarbonyl)-6-(2,2,2-trichloro-1-iminoethoxy)tetrahydro-2H-pyran-3,4,5-triyl triacetate according to the reaction scheme below to obtain compound (A4) according to the reaction scheme below

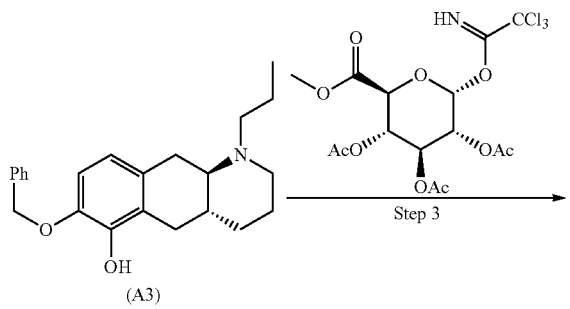

E20. The process according to any of embodiments 18-19, wherein said reaction takes place in an organic solvent such as for example dichloromethane or (trifluoromethyl)benzene in the presence of a protic acid such as trifluoromethanesulfonic acid or a combination of a Lewis acid and protic acid such as for example boron trifluoride diethyl etherate and hydroiodide.

E21. The process according to any of embodiments 18-20 further comprising extracting the crude compound (A4) into a solution with pH between 1-5, such as between 2-4, such as between 2.5-3.5, such as between 2.7-3.2, such as about 3; and subsequently isolating compound (A4).

E22. The process according to any of embodiments 18-20 further comprising extracting the crude compound (A4) into a solution of an acid with pKa between 2-4, such as between 2.5-3.5, such as between 2.7-3.2, such as about 3; such as for example a citric acid solution; and subsequently isolating compound (A4).

E23. The compound of formula (A4) below:

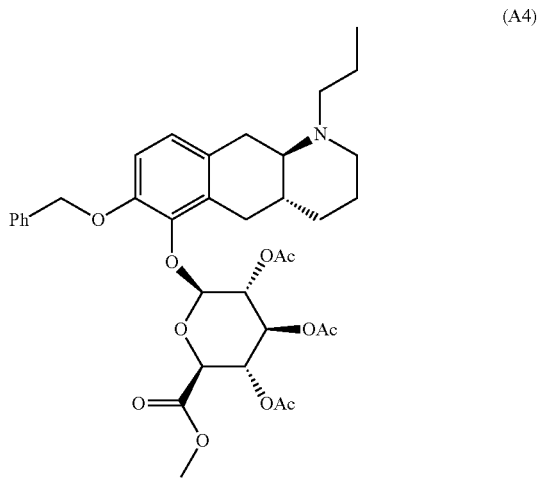

or a salt thereof.

E24. Use of a compound according to embodiment 23 in a process for the manufacture of compound (Id).

E25. A process for the preparation of compound (Id) with the formula below from compound (I) with the formula below comprising the following step 4) reacting compound (A4), or a salt thereof with alkali-hydroxide to obtain (A5-Y) according to the reaction scheme below wherein Y is selected from Li, Na and K.

E26. A process for the manufacture of the compound according to formula (A5-Y) below, comprising the following step 4) reacting compound (A4), or a salt thereof with alkali-hydroxide to obtain (A5-Y) according to the reaction scheme below wherein Y is selected from Li, Na and K.

E27. The process according to any of embodiments 25-26 wherein:
   a) said alkali hydroxide is lithium hydroxide and Y is Li; or
   b) said alkali hydroxide is sodium hydroxide and Y is Na; or
   c) said alkali hydroxide is potassium hydroxide and Y is K.

E28. The process according to any of embodiments 25-27, wherein compound (A5-Y) is isolated by precipitation from an aqueous solution.

E29. The compound of formula A5 below:

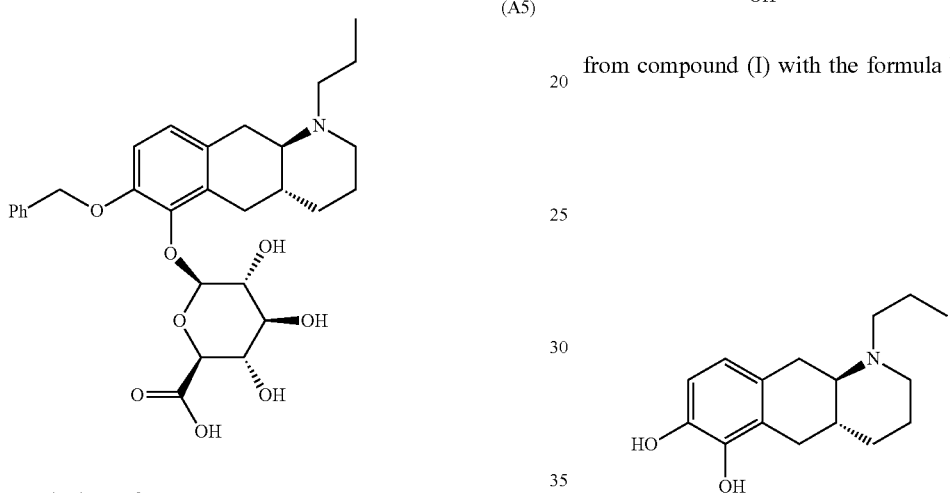

(A5)

or a salt thereof.

E30. The compound according to embodiment 29 which is in the form of an alkali salt depicted below (A5-Y)

wherein Y is selected from Li, Na and K.

E31. The compound according to embodiment 30 wherein Y is K.

E32. Use of a compound according to any of embodiments 29-31 in a process for the manufacture of compound (Id)

E33. A process for the preparation of compound (Id) with the formula below

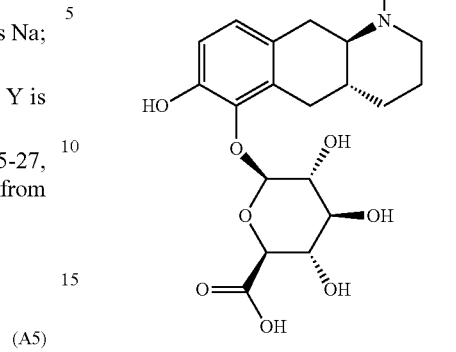

(Id)

from compound (I) with the formula below (I)

comprising the following step
   5) debenzylating compound (A5-Y) to obtain compound (Id) according to the reaction scheme below

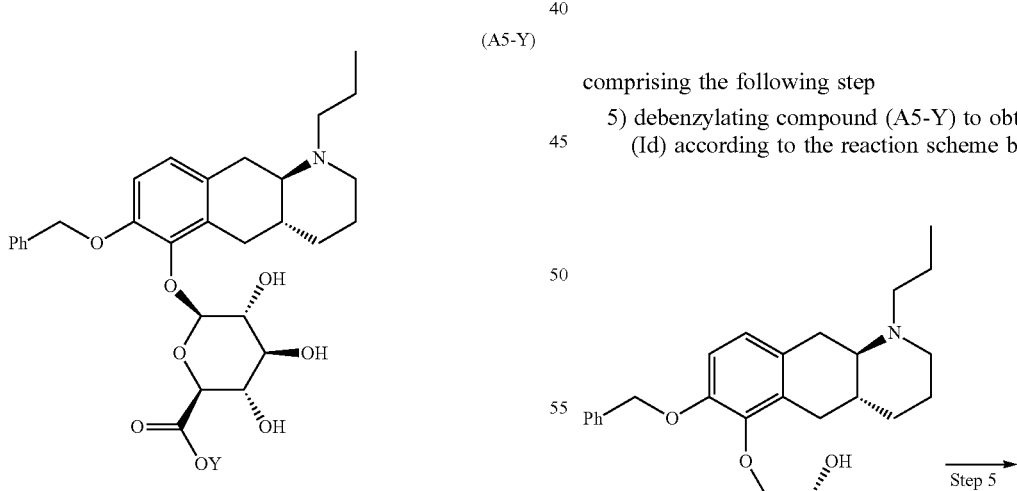

(A5-Y) Step 5

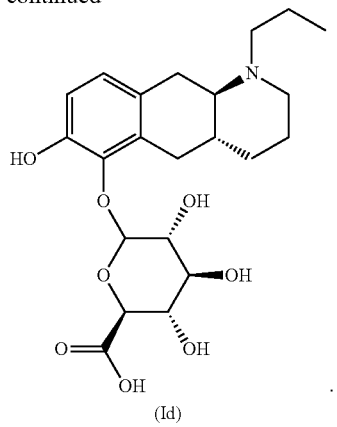

(Id)

E34. The process according to embodiment 33, wherein said debenzylation is performed by hydrogenation in water e.g. in the presence of Pd/C and hydrogen at about 2 bar.

E35. The process according to an of embodiments 33-34, wherein compound (Id) is isolated via filtration and neutralized with an acid such as for example HCl, thereby affording compound (Id) as a heptahydrate.

E36. A process for the preparation of compound (Id) from compound (I) comprising
- step 1) according to any of embodiments 1 and 3-5; followed by
- step 2) according to any of embodiments 8 to 12 and 14.

E37. A process for the preparation of compound (Id) from compound (I) comprising
- step 2) according to any of embodiments 8 to 12 and 14; followed by
- step 3) according to any of embodiments 18 and 20-22.

E38. A process for the preparation of compound (Id) from compound (I) comprising
- step 3) according to any of embodiments 18 and 20-22; followed by
- step 4) according to any of embodiments 25 and 27-28.

E39. A process for the preparation of compound (Id) from compound (I) comprising
- step 4) according to any of embodiments 25 and 27-28; followed by
- step 5) according to any of embodiments 33-35.

E40. A process for the preparation of compound (Id) from compound (I) comprising
- step 1) according to any of embodiments 1 and 3-5; followed by
- step 2) according to any of embodiments 8 to 12 and 14; followed by
- step 3) according to any of embodiments 18 and 20-22.

E41. A process for the preparation of compound (Id) from compound (I) comprising
- step 2) according to any of embodiments 8 to 12 and 14; followed by
- step 3) according to any of embodiments 18 and 20-22; followed by
- step 4) according to any of embodiments 25 and 27-28.

E42. A process for the preparation of compound (Id) from compound (I) comprising
- step 3) according to any of embodiments 18 and 20-22; followed by
- step 4) according to any of embodiments 25 and 27-28; followed by
- step 5) according to any of embodiments 33-35.

E43. A process for the preparation of compound (Id) from compound (I) comprising
- step 1) according to any of embodiments 1 and 3-5; followed by
- step 2) according to any of embodiments 8 to 12 and 14; followed by
- step 3) according to any of embodiments 18 and 20-22; followed by
- step 4) according to any of embodiments 25 and 27-28.

E44. A process for the preparation of compound (Id) from compound (I) comprising
- step 2) according to any of embodiments 8 to 12 and 14; followed by
- step 3) according to any of embodiments 18 and 20-22; followed by
- step 4) according to any of embodiments 25 and 27-28; followed by
- step 5) according to any of embodiments 33-35.

E45. A process for the preparation of compound (Id) from compound (I) comprising
- step 1) according to any of embodiments 1 and 3-5; followed by
- step 2) according to any of embodiments 8 to 12 and 14; followed by
- step 3) according to any of embodiments 18 and 20-22; followed by
- step 4) according to any of embodiments 25 and 27-28; followed by
- step 5) according to any of embodiments 33-35.

E46. (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid heptahydrate.

Items

The following items further serve to describe the invention and embodiments thereof.

Item 1. A process for preparation of compound (Id) with the formula below, or a pharmaceutically acceptable salt thereof

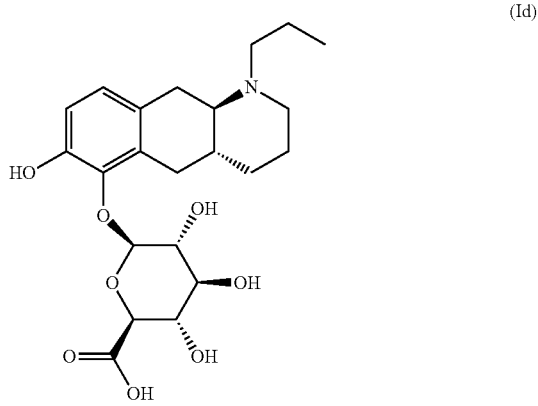

(Id)

from compound (I) with the formula below, or a salt thereof

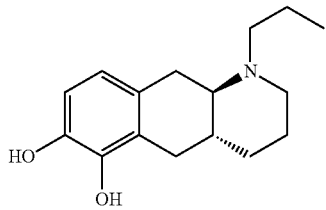

(I)

comprising the following step 1) reacting compound (I), or a salt thereof with benzyl halogenide to obtain compound (A2) according to the reaction scheme below

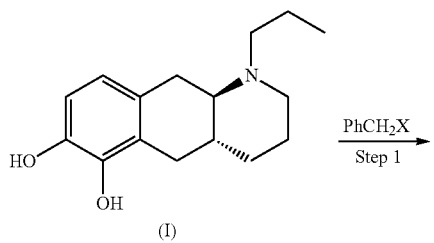

wherein X is selected from the group consisting of Cl, Br and I.

Item 2. A process for preparation of the compound of formula (A2) below comprising the following step 1) reacting compound (I), or salt thereof, with benzyl halogenide to obtain compound (A2) according to the reaction scheme below

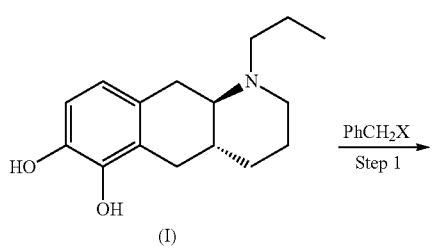

wherein X is selected from the group consisting of Cl, Br and I.

Item 3. The process according to any one of items 1-2, wherein:

a) said benzyl halogenide is benzyl chloride and X is Cl; or b) said benzyl halogenide is benzyl bromide and X is Br.

Item 4. The process according to any one of items 1-3, wherein said benzyl halogenide is benzyl chloride and X is Cl.

Item 5. The process according to any one of items 1-4, wherein said reaction takes place in an organic solvent and in the presence of a base.

Item 6. The process according to any one of items 1-5, wherein said reaction takes place in an organic solvent selected from the group consisting of acetonitrile (MeCN) or dimethylformamide (DMF) and methyl isobutyl ketone (MIBK).

Item 7. The process according to any one of items 1-6, wherein said reaction takes place in the presence of a base selected from the group consisting of sodium hydroxide (NaOH), potassium hydroxide (KOH) and potassium carbonate ($K_2CO_3$).

Item 8. The process according to any one of items 1-7, wherein said reaction takes place in an organic solvent, such as for example acetonitrile (MeCN), dimethylformamide (DMF) or methyl isobutyl ketone (MIBK); and in the presence of a base, such as for example sodium or potassium hydroxide (NaOH or KOH) or potassium carbonate ($K_2CO_3$).

Item 9. The process according to any one of items 1-8, wherein said organic solvent is methyl isobutyl ketone (MIBK), and said base is potassium carbonate ($K_2CO_3$).

Item 10. The process according to any one of items 1-9, wherein compound (I) is in the form of the HCl salt as shown below

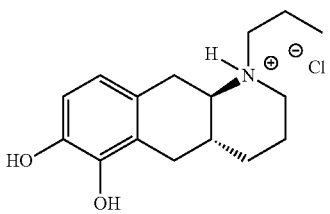

(I)

Item 11. A compound of formula (A2) below:

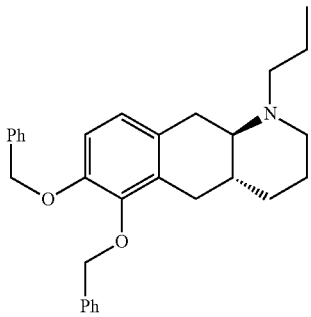

(A2)

or a salt thereof.

Item 12. Compound (A2) as obtained by the process according to any one of items 2-10.

Item 13. Use of a compound according to item 11, in a process for the manufacturing of the compound of formula (Id).

Item 14. A process for preparation of compound (Id) with the formula below

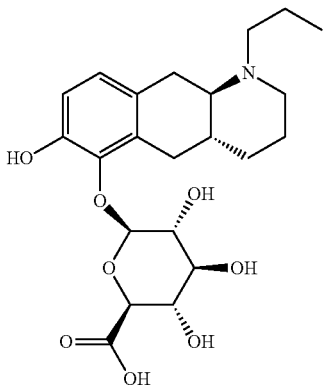

(Id)

from compound (I) with the formula below

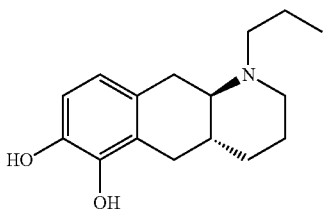

(I)

the process comprising the following step:

2) subjecting compound (A2) to a debenzylation reaction to obtain compound (A3), or a salt thereof, according to the reaction scheme below

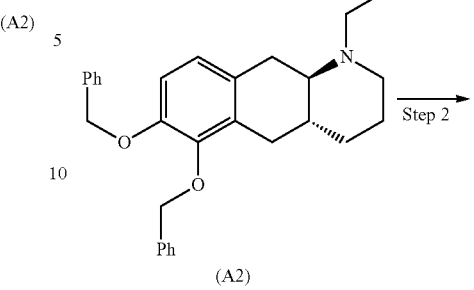

(A2)

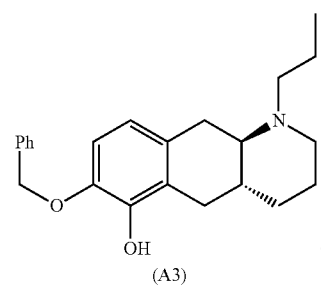

(A3)

Item 15. The process according to item 14, wherein the debenzylation reaction comprises the steps of:
  I) reacting trimethylsilyl iodide with compound (A2) to form a mixture;
  II) adding an alcohol to said mixture obtained from step I) to obtain compound (A3) or a salt thereof;
  III) optionally isolating compound (A3) or a salt thereof.

Item 16. The process according to item 15, wherein step I) takes place in an organic solvent selected from the group consisting of acetonitrile (MeCN), dichloromethane (CH$_2$Cl$_2$), and chloroform (CHCl$_3$).

Item 17. The process according to any of items 15-16, wherein step I) takes place in an organic solvent such as acetonitrile (MeCN).

Item 18. The process according to any one of items 15-17, wherein step I) takes place under nitrogen atmosphere.

Item 19. The process according to any one of items 15-18, wherein said reaction in step I) takes place under nitrogen atmosphere in an organic solvent such as for example acetonitrile (MeCN), dichloromethane (CH$_2$Cl$_2$), or chloroform (CHCl$_3$).

Item 20. The process according to any one of items 15-19, wherein the alcohol added to said mixture in step II) is selected from the group consisting of MeOH, n-heptyl alcohol, and ethanol.

Item 21. The process according to any one of items 15-20, wherein the alcohol added to said mixture in step II) is MeOH or n-heptyl alcohol.

Item 22. The process according to any one of items 15-21, wherein the alcohol added to said mixture in step II) is ethanol.

Item 23. The process according to any one of items 15-22, wherein isopropyl acetate is added to the compound (A3) obtained in step II).

Item 24. The process according to any one of items 15-23, comprising step III), wherein compound (A3) or a salt thereof is isolated.

Item 25. The process according to any one of items 15-24, wherein compound (A3) is obtained in the form of a hydroiodide salt (A3-HI) as shown in the formula below

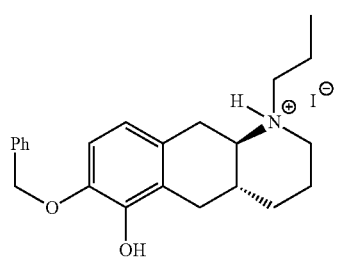
(A3-HI)

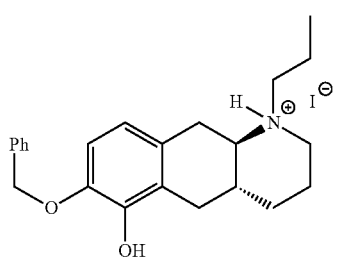
(A3-HI)

Item 26. A process for preparation of the compound of formula (A3), comprising the steps as defined by items 14-24.

Item 27. A process for preparation of the compound of formula (A3-HI) below, comprising the following step
2) reacting compound (A2) with trimethylsilyl iodide to obtain compound (A3-HI)

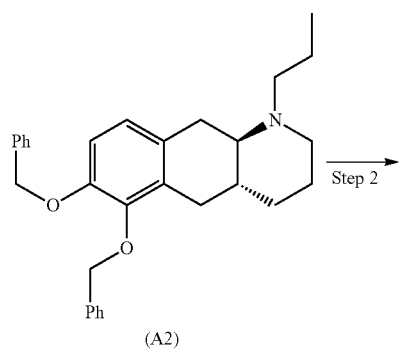
(A2)

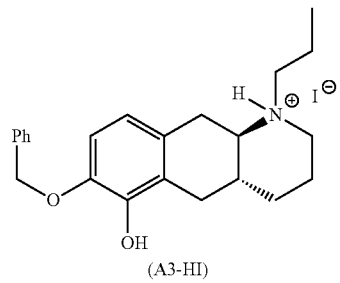
(A3-HI)

Item 28. The process according to item 27, comprising one or more steps as defined by any one of items 14-25.

Item 29. A compound of formula (A3) below:

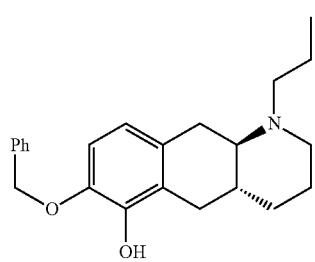
(A3)

or a salt thereof.

Item 30. The compound according to item 28, wherein said compound is the hydroiodide salt of the formula (A3-HI) below Item 31. Compound (A3) as obtained by the process according to any one of items 14-24.

Item 32. Compound (A3-HI) as obtained by the process according to any one of items 14-25.

Item 33. Use of a compound according to any one of items 29-32 in a process for preparation of compound (Id).

Item 34. A process for preparation of compound (Id) with the formula below

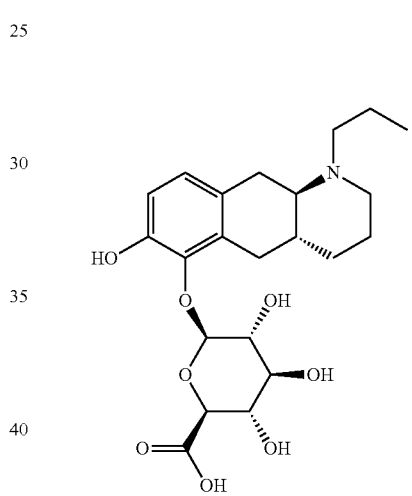
(Id)

from compound (I) with the formula below

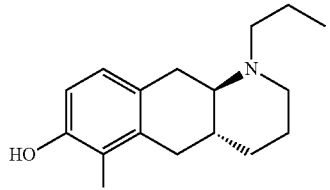
(I)

comprising the following step
3) reacting compound (A3) or a salt thereof with (2S,3S, 4S,5R,6R)-2-(methoxycarbonyl)-6-(2,2,2-trichloro-1-iminoethoxy)tetrahydro-2H-pyran-3,4,5-triyl triacetate to obtain compound (A4) according to the reaction scheme below

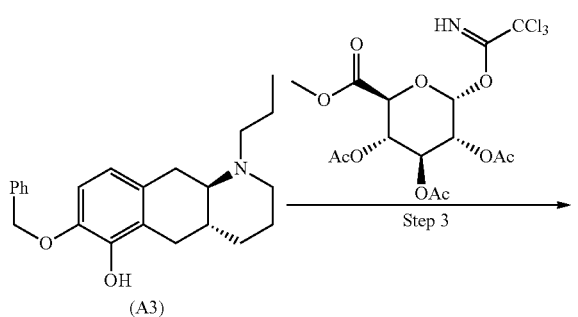

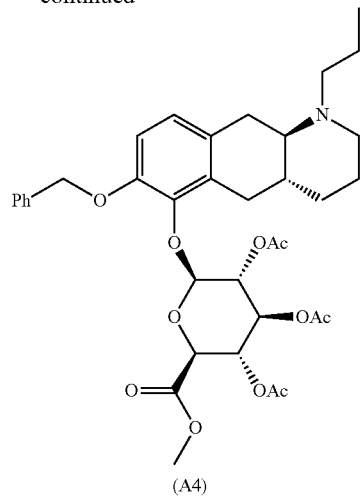

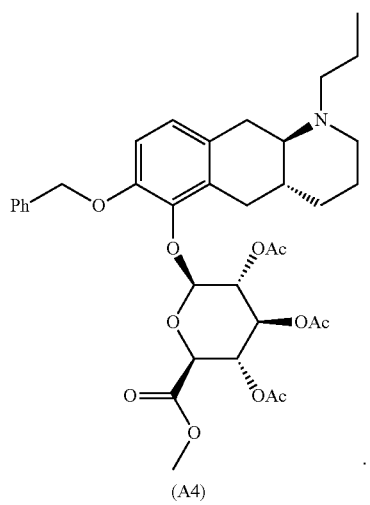

Item 35. A process for preparation of the compound of formula (A4) below, comprising the following step
  3) reacting compound (A3) or a salt thereof, with (2S,3S,4S,5R,6R)-2-(methoxycarbonyl)-6-(2,2,2-trichloro-1-iminoethoxy)tetrahydro-2H-pyran-3,4,5-triyl triacetate according to the reaction scheme below to obtain compound (A4) according to the reaction scheme below

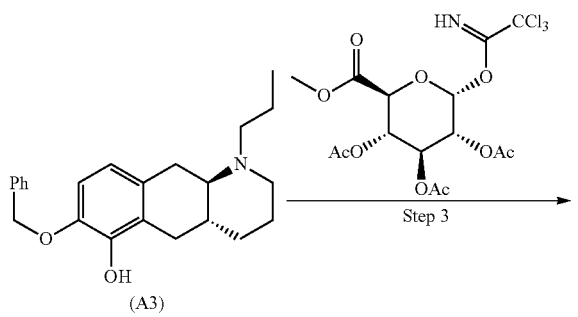

Item 36. The process according to any one of items 34-35, wherein said reaction in step 3 takes place in an organic solvent such as for example dichloromethane or (trifluoromethyl)benzene in the presence of a protic acid such as trifluoromethanesulfonic acid or a combination of a Lewis acid and protic acid such as for example boron trifluoride diethyl etherate and hydroiodide.

Item 37. The process according to any one of items 34-36, wherein said organic solvent is (trifluoromethyl)benzene.

Item 38. The process according to any one of items 34-37, wherein said reaction in step 3 takes place in the presence of boron trifluoride diethyl etherate.

Item 39. The process according to any one of items 34-38, wherein said reaction in step 3 takes place in the presence of trifluoromethanesulfonic acid.

Item 40. The process according to any one of items 34-39, further comprising an additional subsequent step, of extracting the crude compound (A4) into a solution with pH between 1-5, such as between 2-4, such as between 2.5-3.5, such as between 2.7-3.2, such as about 3; and subsequently isolating compound (A4).

Item 41. The process according to any one of items 34-40, further comprising an additional subsequent step, of extracting the crude compound (A4) into a solution of an acid with pKa between 2-4, such as between 2.5-3.5, such as between 2.7-3.2, such as about 3; such as for example a citric acid solution; and subsequently isolating compound (A4).

Item 42. The compound of formula (A4) below:

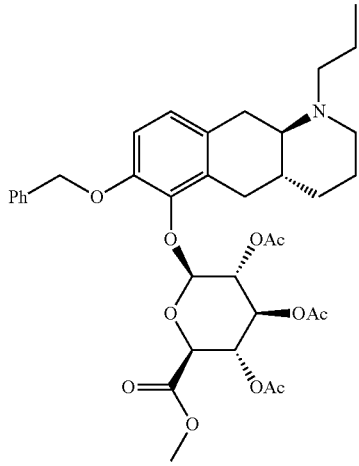

(A4)

or a salt thereof.

Item 43. Compound (A4) or a salt thereof as obtained by the process according to any one of items 35 to 41.

Item 44. Use of a compound according to item 42 in a process for preparation of compound (Id).

Item 45. A process for preparation of compound (Id) with the formula below

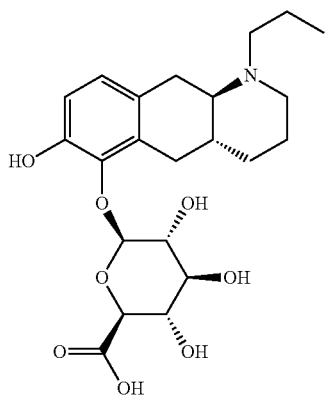

(Id)

from compound (I) with the formula below

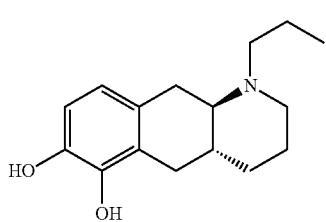

(I)

comprising the following step
4) reacting compound (A4) or a salt thereof, with alkali-hydroxide to obtain (A5-Y) according to the reaction scheme below

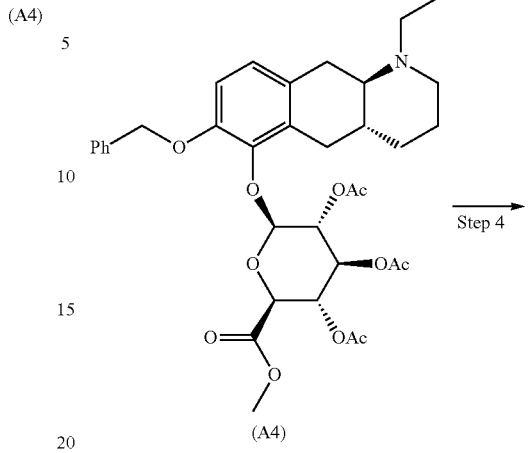

(A4)

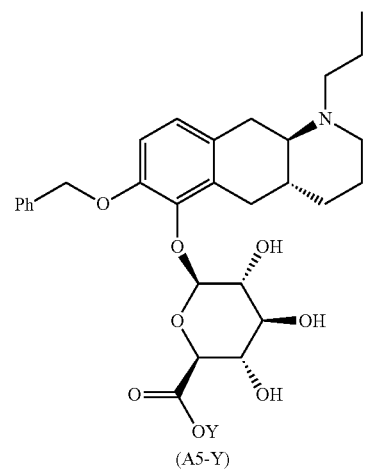

(A5-Y)

wherein Y is selected from Li, Na and K.

Item 46. A process for preparation of the compound according to formula (A5-Y) below, comprising the following step
4) reacting compound (A4), or a salt thereof with alkali-hydroxide to obtain (A5-Y) according to the reaction scheme below

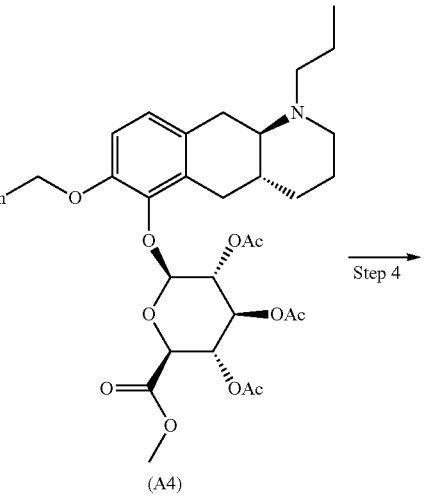

(A4)

-continued

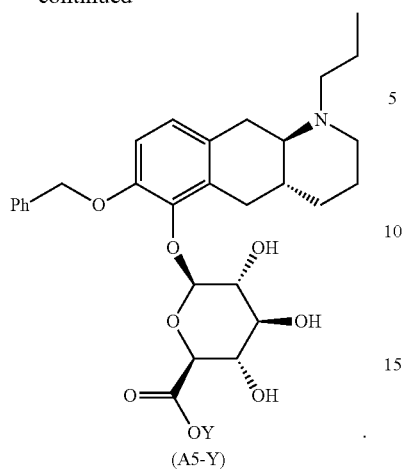

(A5-Y)

wherein Y is selected from Li, Na and K.

Item 47. The process according to any of items 45-46 wherein:
a) said alkali hydroxide is lithium hydroxide and Y is Li; or
b) said alkali hydroxide is sodium hydroxide and Y is Na; or
c) said alkali hydroxide is potassium hydroxide and Y is K.

Item 48. The process according to any one of items 45-47, wherein said alkali-hydroxide is potassium hydroxide and Y is K.

Item 49. The process according to any of items 45-58, wherein compound (A5-Y) is isolated by precipitation from an aqueous solution.

Item 50. The compound of formula A5 below:

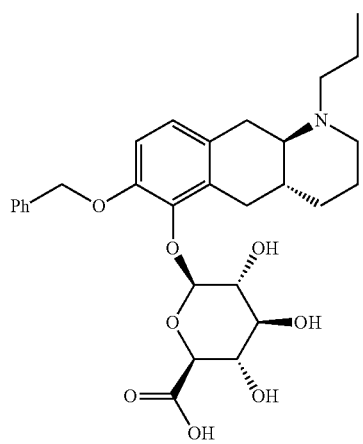

(A5)

or a salt thereof.

Item 51. The compound according to item 50 which is in the form of an alkali salt depicted below

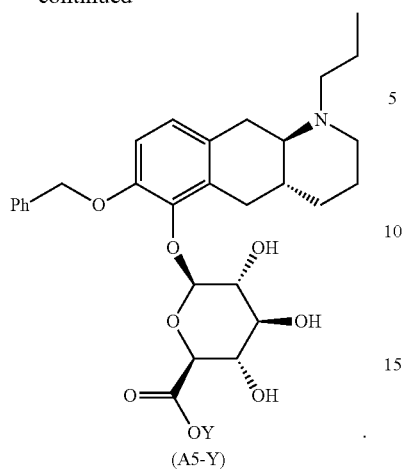

(A5-Y)

wherein Y is selected from the group consisting of Li, Na and K.

Item 52. The compound according to item 51, wherein Y is K.

Item 53. Compound (A5) or a salt thereof as obtained by the process according to any one of items 45-49.

Item 54. Use of a compound according to any of items 50-51 in a process for preparation of compound (Id).

Item 55. A process for preparation of compound (Id) with the formula below

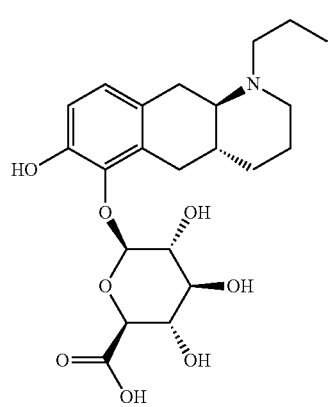

(Id)

from compound (I) with the formula below

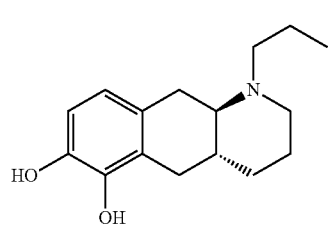

(I)

comprising the following step 5) debenzylating compound (A5-Y) to obtain compound (Id) according to the reaction scheme below

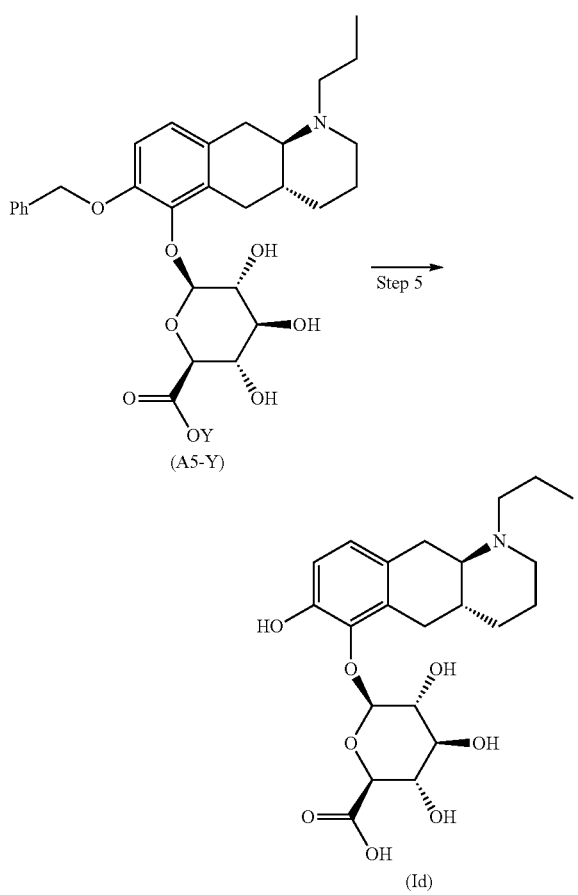

Item 56. The process according to item 55, wherein said debenzylation is performed by hydrogenation in water e.g. in the presence of palladium on carbon (Pd/C) and hydrogen at about 2 bar.

Item 57. The process according to an of items 55-56, wherein compound (Id) is isolated via filtration and neutralized with an acid such as for example HCl, thereby affording compound (Id) as a heptahydrate.

Item 58. A process for preparation of compound (Id) from compound (I) comprising:
step 1) according to any one of items 1 and 3-10; followed by
step 2) according to any one of items 14-25.

Item 59. A process for preparation of compound (Id) from compound (I) comprising:
step 2) according to any one of items 14-25; followed by
step 3) according to any one of items 34 and 36-41.

Item 60. A process for preparation of compound (Id) from compound (I) comprising:
step 3) according to any one of items 34 and 36-41; followed by
step 4) according to any of items 45 and 47-49.

Item 61. A process for preparation of compound (Id) from compound (I) comprising:
step 4) according to any of items 45 and 47-49; followed by
step 5) according to any one of items 55-57.

Item 62. A process for preparation of compound (Id) from compound (I) comprising:
step 1) according to any one of items 1 and 3-10; followed by
step 2) according to any one of items 14-25; followed by
step 3) according to any one of items 34 and 36-41.

Item 63. A process for preparation of compound (Id) from compound (I) comprising:
step 2) according to any one of items 14-25; followed by
step 3) according to any one of items 34 and 36-41; followed by
step 4) according to any of items 45 and 47-49.

Item 64. A process for preparation of compound (Id) from compound (I) comprising
step 3) according to any one of items 34 and 36-41; followed by
step 4) according to any of items 45 and 47-49; followed by
step 5) according to any one of items 55-57.

Item 65. A process for preparation of compound (Id) from compound (I) comprising:
step 1) according to any of items 1 and 3-5; followed by
step 2) according to any one of items 14-25; followed by
step 3) according to any one of items 34 and 36-41; followed by
step 4) according to any of items 45 and 47-49.

Item 66. A process for preparation of compound (Id) from compound (I) comprising:
step 2) according to any one of items 14-25; followed by
step 3) according to any one of items 34 and 36-41; followed by
step 4) according to any of items 45 and 47-49; followed by
step 5) according to any one of items 55-57.

Item 67. A process for preparation of compound (Id) from compound (I) comprising:
step 1) according to any of items 1 and 3-5; followed by
step 2) according to any one of items 14-25; followed by
step 3) according to any one of items 34 and 36-41; followed by
step 4) according to any of items 45 and 47-49; followed by
step 5) according to any one of items 55-57.

Item 68. (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid heptahydrate.

Item 69. The (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid heptahydrate as obtained by the process according to any one of items 55-57.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only and should not be construed as limiting the invention in any way.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (including "for instance", "for example", "e.g.", "such as" and "as such") in the present specification is intended merely to better illuminate the invention and does not pose a limitation on the scope of invention unless otherwise indicated.

It should be understood that the various aspects, embodiments, items, implementations and features of the invention mentioned herein may be claimed separately, or in any combination.

The present invention includes all modifications and equivalents of the subject-matter recited in the claims appended hereto, as permitted by applicable law.

EXPERIMENTAL SECTION

Preparation of the Compound of Formula (Id) and Intermediates

NMR Methods

| QNMR (600 MHz): | |
| --- | --- |
| 1) Relaxation delay | 40 sec |
| 2) Acquisition time | 3.76 sec |
| 3) Time domain | 64k |
| 4) Size | 32k |
| 5) Dummy scans | 4 |
| 6) Scans | 8 |
| 7) Pulse | 30 deg |

LC-MS Methods

Analytical LC-MS data were obtained using the methods identified below.

Method 550: LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC BEH C18 1.7 μm; 2.1×50 mm operating at 60° C. with 1.2 ml/min of a binary gradient consisting of water+0.05% trifluoroacetic acid (A) and acetonitrile/water (95:5)+0.05% trifluoroacetic acid.

| Gradient (linear): | |
| --- | --- |
| 0.00 min | 10% B |
| 1.00 min | 100% B |
| 1.01 min | 10% B |
| 1.15 min | 10% B |
| Total run time: 1.15 minutes | |

Method 551: LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC HSS T3 1.8 μm; 2.1×50 mm operating at 60° C. with 1.2 ml/min of a binary gradient consisting of water+0.05% trifluoroacetic acid (A) and acetonitrile/water (95:5)+0.05% trifluoroacetic acid.

| Gradient (linear): | |
| --- | --- |
| 0.00 min | 2% B |
| 1.00 min | 100% B |
| 1.15 min | 2% B |
| Total run time: 1.15 minutes | |

Method 555: LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC BEH C18 1.7 μm; 2.1×150 mm operating at 60° C. with 0.6 ml/min of a binary gradient consisting of water+0.05% trifluoroacetic acid (A) and acetonitrile/water (95:5)+0.05% trifluoroacetic acid.

| Gradient (linear): | |
| --- | --- |
| 0.00 min | 10% B |
| 3.00 min | 100% B |
| 3.60 min | 10% B |
| Total run time: 3.6 minutes | |

Example 1: Preparation of Compound (A2) (Step 1)

Example 1a

A 50 mL round-bottom flask with a magnetic stir bar was charged with HCl salt of compound (I) (775 mg, 2.60 mmol) and $K_2CO_3$ (1260 mg, 9.12 mmol). Then, a stopper was placed in the neck and the flask was evaporated and back filled with nitrogen followed by the introduction of dry acetonitrile (7.8 mL). Subsequently, benzyl chloride (682 mg, 620 μl, 5.39 mmol) was added and the mixture was warmed to 50° C. for 18 hours before it was cooled to room temperature and $Et_3N$ (263 mg, 363 μl, 2.60 mmol) was added and the mixture stirred for an additional hour at room temperature. Then, the mixture was diluted with heptane (5 mL) and water (5 mL) (three phases were observed-heptane in the top, acetonitrile in the middle and water in the bottom) and the heptane/acetonitrile phase was extracted with water (3×5 mL) (after one extraction with water the acetonitrile phase went into the water phase as expected). The combined aqueous phases were extracted with heptane (3×5 mL) and the combined organic phases were washed with brine (5 mL) and concentrated. From the LC-MS it was observed that only triple benzylated by-product was present in the water phase and from the LC-MS of the isolated solid it was observed that only the product was present. After concentration, a syrup/oil was obtained which solidified overnight upon standing under vacuum. This afforded crude compound (A2) (992 mg) as a solid.

LCMS (method 550): retention time (RT)=0.73 minutes, $[M+H]^+$=442.6 m/z.

Example 1b

A one-necked 1 L round-bottom flask with a magnetic stir bar was charged with HCl salt of compound (I) (10.75 g, 36.1 mmol) and $K_2CO_3$ (17.5 g, 126 mmol). The flask was evaporated and back filled with nitrogen followed by the introduction of dry DMF (107 mL). Subsequently, benzyl chloride (9.41 g, 8.55 mL, 74.3 mmol) was added and the mixture was stirred at room temperature for 18 hours, then warmed to 100° C. for 5 hours and then cooled to room temperature and stirred for additional 19 hours. Subsequently, additional $K_2CO_3$ (7.48 g, 54.1 mmol) and benzyl chloride (6.85 g, 6.29 mL, 54.1 mmol) was added and the mixture was stirred for 5 hours at 100° C. Then, the mixture was cooled to room temperature and water (500 mL) and heptane (250 mL) was added. The aqueous phase was washed with heptane (3×100 mL) and the combined organic phases were washed with brine (100 mL), dried ($Na_2SO_4$), filtered, and concentrated to give an orange-brown syrup which solidified upon standing under vacuum. The crude product (Compound (A2)) (14.6 g) was taken directly to the next step.

LCMS (method 550): RT=0.73 minutes, $[M+H]^+$=442.6 m/z.

Example 1c

A 15 L reactor were charged with HCl salt of compound (I) (600 g, 2015 mmol), $K_2CO_3$ (974 g, 7047 mmol), benzyl chloride (487 ml, 536 g, 4234 mmol) and MIBK (4.8 L). A nitrogen atmosphere was established. The reaction suspension was heated to 105° C. for 17 hours before cooled to room temperature. Additional benzyl chloride (25 ml, 28 g, 221 mmol) was added and the reaction mixture was reheated at 105° C. for another 18 hours before cooled to room temperature. Cold water (4.8 L) was charged to the reaction mixture and the mixture was stirred for 30 minutes. The bottom water phase was discarded. 3M citric acid (3 L) was added and the mixture was stirred well for 45 minutes. The phases were separated. The bottom citric acid water phase was washed with a mixture of Me-THF (1.2 L) and heptane (2.4 L). The slowly separating viscous citric acid water phase was recharged to the empty 15 L reactor and Me-THF (3 L) was added. 25% aqueous ammonia (3 L) was added temperature rate-controlled at 20-38° C. to pH 10-11. Heptane (4.5 L) was added and after stirring for 15 minutes the phases were separated. The organic phase was washed with water (3 L) and then concentrated under reduced pressure/ 50° C. to 1 L, approximately. Acetonitrile (1 L) was added and the mixture was re-concentrated under reduced pressure/ 50° C. to approximately 0.9 L. Acetonitrile (2.5 L) was added and the crude product (Compound A2, approximately 800 g) in solution was taken directly into the next step.

Example 2: Preparation of Compound (A3-HI) (Step 2)

Example 2a

A 1 L one-necked round-bottom flask was charged with a magnetic stir bar and compound (A2) (11.54 g, 26.1 mmol). Then, a rubber stopper was placed in the flask and the flask was evaporated and back-filled with nitrogen three times. Subsequently, dry acetonitrile (115 mL) was added and the mixture was stirred until all starting material was dissolved. Then, TMS-1 (13.23 g, 9.00 mL, 66.1 mmol) was added and the mixture was stirred under nitrogen at room temperature for 17 hours in which a precipitation was observed after the addition. Afterwards, n-heptyl alcohol (15.18 g, 18.55 mL, 131 mmol) was added and the mixture was stirred for 45 minutes in which the TMS capped product was desilylated. During the addition of n-heptyl alcohol the solid dissolved and after 1-2 minutes a new solid was formed. Subsequently, 1:15 (v/v) isopropyl acetate/heptane (160 mL) was added and the mixture was cooled (ice-bath) and stirred for 60 min. The precipitate was filtered off and the filter cake was washed with 1:15 (v/v) isopropyl acetate/heptane (50 mL). The solid was dried in the vacuum oven for 21 hours at 40° C. giving the crude compound (A3-HI) (10.14 g).

Example 2b

A 1 L one-necked round-bottom flask was charged with a magnetic stir bar and compound (A2) (11.9 g, 26.8 mmol). Then, a rubber stopper was placed in the flask and the flask was evaporated and back-filled with nitrogen three times. Subsequently, dry MeCN (180 mL) was added and the mixture was stirred until all starting material was dissolved, then, TMS-1 (14.7 g, 10.0 mL, 73.4 mmol) was added and the mixture was stirred under nitrogen at room temperature for 2 hours in which a precipitate formed. Then, MeOH (5.5 mL) was added and the mixture was stirred for 1 hour. During the addition of MeOH the solid dissolved and a new solid was formed. Subsequently, 1:15 (v/v) isopropyl acetate/heptane (160 mL) was added and the mixture was cooled (ice-bath) and stirred for 60 minutes. The precipitate was filtered off and washed with 1:15 (v/v) isopropyl acetate/heptane (1×50 mL). The solid was dried in a vacuum oven at 40° C. giving compound (A3-HI) (7.6 g).

LCMS (method 550): RT=0.55 minutes, $[M+H]^+$=352.5 m/z.

$^1$H NMR (600 MHz, Chloroform-$d_3$) δ 10.42 (bs, 1H), 7.43-7.33 (m, 5H), 6.78 (d, J=8.3 Hz, 1H), 6.58 (d, J=8.3 Hz, 1H), 5.72 (s, 1H), 5.08 (s, 2H), 3.71 (dd, J=15.1, 11.3 Hz, 1H), 3.58 (ddt, J=10.3, 4.0, 2.0, 1H), 3.25-3.11 (m, 4H), 2.90 (m, 1H), 2.72 (qt, J=13.6, 3.8 Hz, 1H), 2.61 (qdd, J=11.5, 5.5, 3.9 Hz, 1H), 2.26 (dd, J=11.70 Hz, 17.0 Hz 1H), 2.19 (m, 1H), 1.97 (m, 2H), 1.75 (tdd, J=12.5, 7.4, 5.5 Hz, 1H), 1.39 (qd, J=13.5, 11.7, 3.9 Hz, 1H), 1.06 (t, J=7.3 Hz, 3H).

Example 2c

A 15 L reactor was charged with an acetonitrile solution (from example 1c) of crude compound A2 (2821 g solution, approximately 800 g of compound A2, 1810 mmol). The solution was heated to reflux, and solvent was distilled off to a final volume of approximately 0.9 L. Acetonitrile (6 L) was added and the solution was heated to 30° C. A freshly prepared mixture of trimethylsilyl iodide (661 ml, 929 g, 4640 mmol) in isopropylacetate (1100 ml) was added over 5 minutes to the reaction mixture. The reaction mixture was stirred 3.5 hours at 30-32° C. and then cooled to 25° C. and stirred overnight. The reaction mixture was sampled for HPLC analysis. At 25° C., the reaction mixture was quenched by addition of ethanol (650 ml) which shortly resulted in a clear solution but was followed by precipitation of the product. The slurry was stirred 2 hours at 28° C. and then isopropyl acetate (7 L) was added. The slurry was stirred 1 hour at 28° C. and then cooled slowly overnight to room temperature. The slurry was cooled to 15° C. and stirred 2 hours followed by filtration. The filter cake was washed with a mixture of acetonitrile/isopropyl acetate (1:2, 3 L) and then isopropyl acetate (1 L). The solid was dried in the vacuum oven for 3 days at 40° C. which afforded compound (A3-HI) (632 g).

Liberation of Free Base Form of (4aR,10aR)-7-(benzyloxy)-1-propyl-1,2,3,4,4a,5,10,10a-octahydrobenzo[g]quinolin-6-ol from Hydroiodide Salt A 250 mL round-bottom flask was charged with a magnetic stir bar, compound (A3-HI) (6.00 g, 12.52 mmol) and K$_2$CO$_3$ (1.82 g, 13.14 mmol) followed by the introduction of isopropanol (46.8 g, 60.0 ml, 779 mmol) which afforded a slurry. The slurry was stirred for 30 minutes before 5% brine (40 mL) was added. The slurry was stirred at room temperature for additionally 30 minutes before the two-phased slurry was poured into a separation funnel. Then, isopropyl acetate (60 mL) was added and the separation funnel was shaken and the two phases were separated and the organic phase was heated with a heating gun in order to dissolve all the product. Then, the organic phase was washed with 5% brine (10 ml) (the organic phase was reheated with a heating gun after each wash) and concentrated to a solid (crude 4.86 g). The crude product was dried in the vacuum oven for 18 h which afforded compound (A3) as a solid (4.78 g). The crude product was used as such.

$^1$H NMR (600 MHz, Chloroform-d$_3$) δ 7.40 (m, 4H), 7.36 (m, 1H), 6.75 (d, J=8.3 Hz, 1H), 6.60 (d, J=8.3 Hz, 1H), 5.72 (s, 1H), 5.08 (s, 2H), 3.14 (dd, J=15.7, 4.8 Hz, 1H), 3.02 (d, J=11.6 Hz, 1H), 2.98 (dd, J=17.5, 5.1 Hz, 1H), 2.76 (ddd, J=13.2, 10.4, 6.0 Hz, 1H), 2.65 (t, J=13.5 Hz, 1H), 2.53 (td, J=12.9, 12.0, 5.5 Hz, 1H), 2.31 (td, J=11.0, 4.3 Hz, 1H), 2.23 (dd, J=17.3, 11.6 Hz, 2H), 1.95 (m, 1H), 1.72 (m, 3H), 1.54 (qdd, J=13.8, 11.4, 6.2 Hz, 2H), 1.15 (m, 1H), 0.90 (t, J=7.4 Hz, 3H).

Example 3: Preparation of Compound (A4) (Step 3)

Example 3a

Compound (A3-HI) (6.20 g, 12.9 mmol) and (2S,3S,4S,5R,6R)-2-(methoxycarbonyl)-6-(2,2,2-trichloro-1-iminoethoxy)tetrahydro-2H-pyran-3,4,5-triyl triacetate (24.8 g, 51.7 mmol) were suspended in (trifluoromethyl)benzene (112 mL), and cooled to 2° C. Then boron trifluoride diethyl etherate (2.29 g, 2.05 ml, 16.2 mmol) was added under a nitrogen atmosphere and the mixture was stirred at 2° C. for 20 minutes, then warmed to 25° C. and stirred overnight under nitrogen. After a total of 21 hours, the mixture was cooled to 5° C. and quenched by the addition of triethylamine (6.22 g, 8.6 mL, 61.4 mmol) and methanol (15.5 mL), the cooling bath was removed and the mixture was stirred for 1 hour and 10 minutes, then water (90 mL) was added. The organic phase was washed with water (2×65 mL) and the combined aqueous phase was extracted with (trifluoromethyl)benzene (25 mL). The combined organic phases were extracted with concentrated aqueous citric acid (82 mL, 262 mmol, 3.18 molar) and the mixture was stirred for 20 minutes. The organic phase was extracted with additional concentrated aqueous citric acid (61.0 mL, 194 mmol, 3.18 molar). THF/n-heptane (2:1, 50 mL) was added to the citric acid phase, and the mixture was cooled to 5° C. and slowly neutralized with aqueous ammonia (125 ml, 0.166 mol, 25%) with high stirring (>500 rpm) and temperature <16° C. until pH=7.8. The aqueous phase was extracted with additional THF/n-heptane (2:1, 50 mL) and the combined organic phase was dried (Na$_2$SO$_4$), filtered and evaporated to dryness in vacuo affording crude compound (A4) (10.6 g).

LC-MS (method 555): RT=2.18 minutes, [M+H]$^+$=668.4 m/z.

Example 3b

Prepared from Free Base of (4aR,10aR)-7-(benzyloxy)-1-propyl-1,2,3,4,4a,5,10,10a-octahydrobenzo[g]quinolin-6-ol A suspension of dried compound (A3) (2.00 g, 5.69 mmol) and (2S,3S,4S,5R,6R)-2-(methoxycarbonyl)-6-(2,2,2-trichloro-1-iminoethoxy)tetrahydro-2H-pyran-3,4,5-triyl triacetate (6.81 g, 14.23 mmol) in (trifluoromethyl)benzene (36 mL) was cooled to 0° C. under nitrogen. Subsequently, trifluoromethanesulfonic acid (1.281 g, 0.758 mL, 8.54 mmol) was added dropwise in which the slurry dissolved fast followed by the formation of a new precipitate after 10 minutes. The mixture was stirred for 1 h at 0° C. under nitrogen. LC-MS indicated full conversion of the starting material after 1 h. Subsequently, Et$_3$N (2.61 g, 3.60 mL, 25.8 mmol) and MeOH (3.96 g, 5.00 ml, 124 mmol) were added and the ice-bath was removed. The mixture was stirred for 30 minutes at room temperature. Then, water (28 mL) was added and the two phases were separated. The organic phase was washed with water (28 mL) and the combined aqueous phases were extracted with (trifluoromethyl)benzene (12 mL). To the combined organic phases was added 3.18 M citric acid (26.0 mL, 83 mmol, 3.18 M) and the mixture was stirred for 25 minutes. The two phases were separated and the organic phase was extracted additionally with 3.18 M citric acid (12 mL, 38.2 mmol, 3.18 molar). Then, isopropyl acetate (26 mL) was added to the aqueous phase and the solution was cooled on ice. Subsequently, 25% ammonia (0.388 g, 0.493 ml, 5.69 mmol, 25%) was added over the course of 1.5 hours until pH 7.5 was reached. The two phases were separated and the aqueous phase was extracted with isopropyl acetate (26 mL). The combined organic phases were dried over Na$_2$SO$_4$, filtered and concentrated to a brown foam which was left under vacuum overnight (crude: 5.00 g). This afforded the crude compound (A4) (5.00 g). The crude product was used directly in example 4b.

LC-MS (method 555): RT=2.18 minutes, [M+H]$^+$=668.3 m/z.

Example 4: Preparation of Compound (A5-K) (Step 4)

Example 4a

Compound (A4) (10.6 g, 8.68 mmol, 54.5% (w/w)) was dissolved in THF (45.5 mL)/n-heptane (4.5 mL) and H$_2$O (50 mL) was added. The mixture was cooled to 6° C. and aqueous potassium hydroxide (9.52 g, 6.52 ml, 78 mmol, 46%) was added and the mixture was slowly warmed to room temperature over a period of 2.5 hours. n-Heptane (10 mL) was added resulting in phase separation. The organic phase was discarded. The aqueous phase was washed with THF:n-heptane (25 mL, 4:1) and then concentrated (THF removed) in vacuo at 42° C., resulting in precipitation. The mixture was stirred at 0° C. for 20 minutes, then filtered affording a solid, which was dried in the vacuum oven for 3 hours affording compound (A5-K) (4.8 g).

LC-MS (method 550): RT=0.41 minutes, [M+H]$^+$=528.4 m/z.

$^1$H NMR (600 MHz, Deuterium Oxide) δ 7.42-7.26 (m, 5H), 6.89 (d, J=8.5 Hz, 1H), 6.82 (d, J=8.5 Hz, 1H), 5.04 (d, J=2.8 Hz, 2H), 4.91-4.88 (m, 1H), 3.53-3.45 (m, 4H), 3.42-3.32 (m, 1H), 3.31-3.17 (m, 3H), 3.11 (td, J=11.3, 5.3 Hz, 1H), 3.05-2.93 (m, 2H), 2.69 (dd, J=15.7, 11.0 Hz, 1H), 2.26 (dd, J=17.6, 11.7 Hz, 1H), 1.93 (t, J=14.2 Hz, 2H), 1.85-1.66 (m, 3H), 1.61 (tt, J=12.5, 6.3 Hz, 1H), 1.30 (dd, J=17.6, 8.1 Hz, 1H), 0.90 (td, J=7.4, 1.5 Hz, 3H).

Example 4b

Crude compound (A4) obtained from example 3b (5.0 g, 3.62 mmol, QNMR purity 48.4%) was suspended in THF (12 mL), water (12 mL). n-Heptane (0,813 g, 1,189 ml, 8.12 mmol) was added and the solution was cooled to 0° C. Subsequently, KOH (2.21 g, 1.52 mL, 18.12 mmol, 46% solution) was added over the course of 2 minutes and the mixture was stirred for 4 hours at 1° C. LC-MS didn't indicated full conversion and therefore more KOH (2.91 g, 2.0 mL, 23.87 mmol, 46% solution) was added and the mixture was stirred for additionally 2 hours in which all the starting material was consumed. The mixture was transferred to a separation funnel and n-heptane (12 mL) was added resulting in a phase separation. The two phases were separated. The aqueous phase was washed with 4:1 THF (5 mL)/n-heptane (1.2 mL) and then the brown aqueous phase was concentrated (to remove any THF) in vacuo. The mixture was stirred at room temperature for 3 days and a precipitate was observed before the mixture was cooled to 0° C. and left for 45 minutes. Then, the precipitate was filtered off affording a white solid, which was dried in the vacuum oven overnight at 40° C. to give compound (A5-K) as a white solid (1.98 g).

LC-MS (method 555): RT=1.54 minutes, $[M+H]^+$=528.3 m/z.

$^1$H NMR (600 MHz, Deuterium Oxide) δ 7.47-7.36 (m, 5H), 6.88 (d, J=8.6 Hz, 1H), 6.83 (d, J=8.5 Hz, 1H), 5.13 (m, 2H), 5.01 (d, J=7.9 Hz, 1H), 3.59 (m, 1H), 3.54 (m, 1H), 3.47 (td, J=9.2, 0.7 Hz, 1H), 3.42 (dd, J=9.8, 0.7 Hz, 1H), 3.23 (dd, J=17.6, 4.8 Hz, 1H), 3.13 (dd, J=16.2, 5.1 Hz, 1H), 2.98 (d, J=11.5 Hz, 1H), 2.69 (ddd, J=13.1, 11.4, 5.1 Hz, 1H), 2.49 (dd, J=16.0, 11.1 Hz, 1H), 2.42 (ddd, J=13.1, 11.3, 5.0 Hz, 1H), 2.28 (td, J=12.2, 2.8 Hz, 1H), 2.17 (m, 2H), 1.91 (m, 1H), 1.71 (m, 1H), 1.60 (m, 1H), 1.50 (m, 2H), 1.43 (m, 1H), 1.08 (qd, J=13.0, 4.0 Hz, 1H), 0.85 (t, J=7.3 Hz, 3H).

Example 4c

Compound (A3-HI) (360 g, 751 mmol) and (2S,3S,4S,5R,6R)-2-(methoxycarbonyl)-6-(2,2,2-trichloro-1-iminoethoxy)tetrahydro-2H-pyran-3,4,5-triyl triacetate (1440 g, 3008 mmol) were suspended in (trifluoromethyl)benzene (5760 mL), and cooled to 2° C. Then a mixture of boron trifluoride diethyl etherate (133 g, 116 ml, 940 mmol) in (trifluoromethyl)benzene (720 mL), was added under a nitrogen atmosphere over 25 minutes. The mixture was stirred at 2° C. for 60 minutes, then warmed to 22° C. and stirred 2 hours. The reaction mixture was warmed to 27° C. stirred overnight under nitrogen. After a total of 23 hours at 22-27° C., the reaction mixture was cooled to 2° C. and quenched by the addition of first triethylamine (453 g, 624 mL, 4477 mmol) and then after 15 minutes methanol (494 g, 624 mL, 15410 mmol). The resulting clear solution was warmed to 21° C. and stirred 3.5 hours. Water (4300 mL) was added and the mixture was stirred 30 minutes. The mixture was left separating overnight at 25° C. The organic phase was washed with water (2.5 L). To the organic phase was added 3M of aqueous citric acid (3.6 L) and the mixture was stirred 25 minutes. To the mixture were added THF (1440 mL) and heptane (1440 mL) and the mixture was stirred 10 minutes. The citric acid water phase was kept. To the organic phase was added 3M of aqueous citric acid (2.4 L) and the mixture was stirred 10 minutes. The organic phase was discarded. To the combined citric acid water phases were added THF (1080 mL) and heptane (1080 mL) and the mixture was stirred 10 minutes. The organic phase was discarded. To the citric acid water phase was added THF (2900 mL) and heptane (720 mL) and the mixture was cooled to 5° C. In 3 hours, 25% aqueous ammonia (4.7 L) was added slowly to a pH of 9-9.5 keeping the temperature below 18° C. The phases were separated and the water phase re-extracted with a mixture of THF (1140 mL) and heptane (360 mL). The combined organic phases were washed with a mixture of water (2.2 L) and 25% aqueous ammonia (360 mL) and then two times with 5% NaCl (2×1.8 L). The phases were separated. To the organic phase was added THF (5.4 L) and water (1.8 L) and the mixture was cooled to 3° C. In 2 minutes, a mixture of 12M KOH (424 mL) and water (1.8 L) was added to the cold reaction mixture. The reaction mixture was stirred at 3-5° C. for 1 hour and then warmed to 23° C. over 1.2 hours and stirred overnight at 23° C. Heptane (1.8 L) was added to the reaction mixture and stirring was continued for 10 minutes. The organic phase was discarded. The water phase was washed with a mixture of THF (1440 mL) and heptane (360 mL). The organic phase was discarded. The water phase was heated to 50° C. and a vacuum distillation was performed to remove residual THF. The water phase (4 L) was cooled to 20° C. and stirred overnight. The resulting product suspension was cooled to 2° C. and filtered. The filter cake was washed two times with cold water (2×720 mL). The product was dried overnight at 50° C. in vacuo, and compound (A5-K) was isolated (273 g).

Example 5: Preparation of Compound (Id) (Step 5)

Example 5a (without Seeding)

Compound (A5) (0.59 g, 1.1 mmol) was dissolved in MeOH:water (2:1, 12 mL) and active carbon (0.8 g) was added and the mixture stirred for 20 minutes, then filtered through a plug of filter-aid and the solids washed with MeOH:water (2:1, 4.5 mL). The combined filtrates were placed in the Asynth autoclave and Pd/C (0.30 g, 0.054 mmol, 1.9%) was added and the mixture stirred for at 40° C., filled with nitrogen (three times), then hydrogen (three times, 6 bar). After 1 hour and 30 minutes the mixture was filled with nitrogen three times, then filtered through a plug of filter aid and the solids were washed with MeOH/water (2:1, 15 mL). The filtrate was evaporated to dryness. The solid was dissolved in water (2 mL) and stirred overnight, then filtered affording compound (Id) (0.29 g).

LC-MS (method 551) RT=0.39 minutes, $[M+H]^+$=438.3 m/z.

$^1$H NMR (600 MHz, Deuterium Oxide) δ 6.85 (d, J=8.4 Hz, 1H), 6.77 (d, J=8.4 Hz, 1H), 4.76 (d, J=7.5 Hz, 2H), 3.59-3.55 (m, 2H), 3.54-3.46 (m, 3H), 3.38-3.28 (m, 2H), 3.28-3.19 (m, 2H), 3.20-3.01 (m, 2H), 2.74 (dd, J=15.0, 11.5 Hz, 1H), 2.30 (dd, J=17.5, 11.5 Hz, 1H), 2.00-1.92 (m, 2H), 1.88-1.69 (m, 2H), 1.69-1.58 (m, 1H), 1.33 (dq, J=13.5, 4.0 Hz, 1H), 0.92 (t, J=7.3 Hz, 3H).

Example 5b (with Seeding)

Compound (A5-K) (4.8 g, 8.5 mmol) and Pd/C Johnson-Matthey 5R39 (0.349 g, 0.064 mmol, 1.94% Pd (w/w)) were suspended in $H_2O$ (48 mL) and placed in an autoclave, filled with nitrogen three times, then hydrogen gas (2 bar) three times and the mixture stirred at 40° C. for 1.5 hours. The mixture was backfilled with nitrogen and filtered through a plug into a 100 mL round-bottom flask. The solids were rinsed with water (2×1.5 mL) and the combined aqueous phase was pH adjusted (from pH=10) to pH=6.2 using aqueous HCl (2.1 ml, 8.5 mmol, 4 M) at room temperature and a seeding crystal of compound (Id) was added at 40° C. and precipitation occurred. The mixture was stirred for 2 hours, then cooled to 2° C. The mixture was filtered and dried on the filter overnight with suction affording compound (Id) as a heptahydrate (3.90 g, 6.92 mmol, 82%, >99% purity based on QNMR).

LC-MS (method 551) RT=0.38 minutes, [M+H]$^+$=438.3 m/z.

$^1$H NMR (600 MHz, Deuterium Oxide, maleic acid used as internal standard) δ 6.85 (d, J=8.4 Hz, 1H), 6.75 (d, J=8.4 Hz, 1H), 4.82 (d, J=2.8 Hz, 2H), 3.83 (d, J=9.7 Hz, 1H), 3.61-3.54 (m, 2H), 3.54-3.48 (m, 2H), 3.34 (dd, J=15.5, 5.0 Hz, 1H), 3.28 (dd, J=17.5, 5.0 Hz, 1H), 3.25-3.18 (m, 2H), 3.01-3.08 (m, 2H), 2.73 (dd, J=15.5, 11.5 Hz, 1H), 2.29 (dd, J=17.5, 11.5 Hz, 1H), 1.99-1.90 (m, 2H), 1.89-1.69 (m, 3H), 1.70-1.58 (m, 1H), 1.33 (dq, J=13.5, 4.0 Hz, 1H), 0.91 (t, J=7.3 Hz, 3H).

Example 6: In Vitro and In Vivo Characterization of Compound (Id)

Example 6a: Conversion of the Compound of Formula (Id) in Rat and Human Hepatocytes Compound (Id) was incubated at 1 µg/mL with hepatocytes from human or rat suspended in DMEM (Dulbecco's Modified Eagle Medium) with HEPES (4-(2-hydroxyethyl)-1-piperazineethanesulfonic acid) at pH 7.4. The cell concentration at incubation was 1×10$^6$ viable cells/mL. The incubations were performed in glass tubes at 37° C. with a total incubation volume of 3.5 mL and with duplicate incubations for each test item. The 3.5 mL of hepatocyte suspension was equilibrated for 10 minutes in a water bath set to 37° C. where after the incubations were initiated by adding 3.5 µL of a stock solution of the test item in DMSO (Dimethyl sulfoxide) and gently inverting the tubes. The final solvent concentration in the incubations was 0.1% DMSO. Samples of 600 µL were withdrawn from the incubations at the pre-determined time points of 0.25, 5, 15, 30 and 60 minutes after ensuring homogeneity of hepatocyte suspensions. The withdrawn volume was added to 1 mL Nunc cryotubes on wet ice containing 60 µL of ice-cold ascorbic acid (100 mg/mL) and 30 µL of ice cold 100 mM saccharic acid 1.4-lactone in 0.5 M citric acid. The tubes were mixed and 35 µL of a solution of ice cold 20% formic acid was added. The tubes were mixed thoroughly and stored at −80° C. awaiting analysis. Analysis method and Instrumentation used for analysis of (I) from dosing compound (Id) was the one described in Examples 9 and 10 below in the section "Instrumentation used for analysis of compound (I) from dosing of compound (Ic) and (Id)."

FIG. 7 indicates a time dependent conversion to compound (I) from (Id) in both rat and human hepatocytes.

Example 6b: Conversion of the Compound of Formula (Id) in Fresh Rat and Human Blood Conversion of (Id) in human blood (average of 3 donors) and rat blood (average of 45 donors) to (I) was shown in fresh blood at 37° C. spiked with 1 µg/mL of (Id). (I) was measured at 0, 5, 15, 30 and 60 minutes in isolated plasma. Analysis method and Instrumentation as described in Examples 9 and 10 below in the section "Instrumentation used for analysis of compound (I) from dosing of compounds (Ic) and (Id)."

FIG. 8 indicates a time dependent conversion to compound (I) from (Id), in both rat and human blood.

Example 7: Dopamine Agonist Activity

Dopamine D1 Receptor Agonism

Dopamine D1 receptor agonism was measured using a HTRF cAMP from CisBio using the protocol developed by HD Biosciences (China). Briefly, the assay is a homogeneous time resolved-fluorescence resonance energy transfer (HTRF) assay that measures production of cAMP by cells in a competitive immunoassay between native cAMP produced by cells and cAMP-labeled with XL-665. A cryptate-labeled anti-cAMP antibody visualizes the tracer. The assay was performed in accordance with instructions from manufacturer.

Test compounds were added to wells of microplates (384 format). HEK-293 cells expressing the human D1 receptor were plated at 1000 cells/well and incubated 30 minutes at room temperature. cAMP-d2 tracer was added to wells and followed by addition of Anti-cAMP antibody-cryptate preparation and incubated for 1 hour at room temperature in dark. HTRF cAMP was measured by excitation of the donor with 337 nm laser (the "TRF light unit") and subsequent (delay time 100 microseconds) measurement of cryptate and d2 emission at 615 nm and 665 nm over a time window of 200 microseconds with a 2000 microseconds time window between repeats/100 flashes). HTRF measurements were performed on an Envision microplate reader (PerkinElmer). The HTRF signal was calculated as the emission-ratio at 665 nm over 615 nm. The HTRF ratio readout for test compounds was normalized to 0% and 100% stimulation using control wells with DMSO-solvent or 30 µM dopamine. Test compound potency (EC$_{50}$) was estimated by nonlinear regression using the sigmoidal dose-response (variable slope) using Xlfit 4 (IDBS, Guildford, Surrey, UK, model 205).

$$y=(A+((B-A)/(1+((C/x)^D))))$$

where y is the normalized HTRF ratio measurement for a given concentration of test compound, x is the concentration of test compound, A is the estimated efficacy at infinite compound dilution, and B is the maximal efficacy. C is the EC$_{50}$ value and D is the Hill slope coefficient. EC$_{50}$ estimates were obtained from an independent experiment and the logarithmic average was calculated.

Dopamine D2 Receptor Agonism

Dopamine D2 receptor agonism was measured using a calcium mobilization assay protocol developed by HD Biosciences (China). Briefly, HEK293/G15 cells expressing human D2 receptor were plated at a density of 15000 cells/well in clear-bottomed, Matrigel-coated 384-well plates and grown for 24 hours at 37° C. in the presence of 5% CO$_2$. The cells were incubated with calcium-sensitive fluorescent dye, Fluo8, for 60-90 minutes at 37° C. in the dark. Test compounds were prepared at 3-fold concentrated solution in 1×HBSS buffer with Ca$^{2+}$ and Mg$^{2+}$. Calcium Flux signal was immediately recorded after compounds were added from compound plate to cell plate at FLIPR (Molecular Devices). The fluorescence data were normalized to yield responses for no stimulation (buffer) and full stimulation (1 µM of dopamine) of 0% and 100% stimulation, respectively. Test compound potency (EC$_{50}$) was estimated by nonlinear regression using the sigmoidal dose-response (variable slope) using Xlfit 4 (IDBS, Guildford, Surrey, UK, model 205).

$$y=(A+((B-A)/(1+((C/x)^D))))$$

where y is the normalized ratio measurement for a given concentration of test compound, x is the concentration of test compound, A is the estimated efficacy at infinite compound dilution, and B is the maximal efficacy. C is the $EC_{50}$ value and D is the Hill slope coefficient. $EC_{50}$ estimates were obtained from independent experiment and the logarithmic average was calculated.

Example 8: 5-HT2B Agonist Activity and Binding Assay

5-HT2B Agonist Activity Assay

Evaluation of the agonist activity of compounds (I), (Ia), (Ib), (Ic), and (Id) at the human 5-HT2B receptor was performed by Eurofins/Cerep (France) measuring the compound effects on inositol monophosphate (IP1) production using the HTRF detection method. Briefly, the human 5-HT2B receptor was expressed in transfected CHO cells. The cells were suspended in a buffer containing 10 mM Hepes/NaOH (pH 7.4), 4.2 mM KCl, 146 mM NaCl, 1 mM $CaCl_2$, 0.5 mM $MgCl_2$, 5.5 mM glucose and 50 mM LiCl, then distributed in microplates at a density of 4100 cells/well and incubated for 30 minutes at 37° C. in the presence of buffer (basal control), test compound or reference agonist. For stimulated control measurement, separate assay wells contained 1 μM 5-HT. Following incubation, the cells were lysed and the fluorescence acceptor (fluorophen D2-labeled IP1) and fluorescence donor (anti-IP1 antibody labeled with europium cryptate) were added. After 60 minutes at room temperature, the fluorescence transfer was measured at lambda(Ex) 337 nm and lambda(Em) 620 and 665 nm using a microplate reader (Rubystar, BMG). The IP1 concentration was determined by dividing the signal measured at 665 nm by that measured at 620 nm (ratio). The results were expressed as a percent of the control response to 1 μM 5-HT. The standard reference agonist was 5-HT, which was tested in each experiment at several concentrations to generate a concentration-response curve from which its $EC_{50}$ value is calculated as described above for dopamine functional assays.

5-HT2B Binding Assay

Evaluation of the affinity of compounds for the human 5-HT2B receptor was determined in a radioligand binding assay at Eurofins/Cerep (France). Membrane homogenates prepared from CHO cells expressing the human 5HT2B receptor were incubated for 60 minutes at room temperature with 0.2 nM [$^{125}$I](±)DOI (1-(4-iodo-2, 5-dimethoxyphenyl) propan-2-amine) in the absence or presence of the test compound in a buffer containing 50 mM Tris-HCl (pH 7.4), 5 mM $MgCl_2$, 10 μM pargyline and 0.1% ascorbic acid. Nonspecific binding is determined in the presence of 1 μM (±)DOI. Following incubation, the samples were filtered rapidly under vacuum through glass fiber filters (GF/B, Packard) presoaked with 0.3% polyethyleneimine (PEI) and rinsed several times with ice-cold 50 mM Tris-HCl using a 96-sample cell harvester (Unifilter, Packard). The filters were dried and counted for radioactivity in a scintillation counter (Topcount, Packard) using a scintillation cocktail (Microscint 0, Packard). The results are expressed as a percent inhibition of the control radioligand specific binding. The standard reference compound was (±)DOI, which was tested in each experiment at several concentrations to obtain a competition curve from which its $IC_{50}$ is calculated.

TABLE 2

In vitro activities for the compounds of formula (I), (Ia), (Ib), (Ic) and (Id) obtained according to Examples 7 and 8

|  | Compound | D1 $EC_{50}$ (nM)/Emax | D2 $EC_{50}$ (nM)/Emax | 5-HT2B $EC_{50}$ (nM)/Emax |
|---|---|---|---|---|
| Parent compound | (I) | 3.3/99% | 1.3/91% | 2900 nM/50% |
| Prodrugs in the state of the art | (Ia) | >1000 | >1000 | >6000 nM, 58% @ 30 μM |
|  | (Ib) | >1000 | 46nM/100% | 3.8 nM/79% |
|  | (Ic) | nd | nd | −5% @ 10 μM |
| Compound obtained by the invention | (Id) | 2700/98% | 1100/92% | −25% @ 10 μM* |

*indicate binding affinity (% inhibition of control, specific binding at concentration indicated)
nd: not determined

Example 9: PK Experiments in Rats

For all the experiments, blood samples of approximately 0.68 mL were drawn from the tail or sublingual vein and put into $K_3$EDTA tubes that had been pre-cooled and prepared with stabilizing solution consisting of 80 μL ascorbic acid and 40 μL 100 mM D-saccharic acid 1,4 lactone in water. The tubes were inverted gently 6-8 times to ensure thorough mixing and then placed in wet ice. The collecting tube was placed in wet ice for up to 30 minutes until centrifugation. Once removed from the wet ice the centrifugation was initiated immediately. Immediately after end of centrifugation the samples were returned to wet ice. Three sub-samples of 130 μL plasma were transferred to each of three appropriately labelled cryo tubes containing 6.5 μL pre-cooled formic acid (20%) (the tubes were pre-spiked and stored refrigerated prior to use). The tube lid was immediately replaced and the plasma solution was thoroughly mixed by inverting gently 6-8 times. The samples were stored frozen at nominally −70° C. within 60 minutes after sampling. Centrifugation conditions at 3000 G for 10 minutes at 4° C. Plasma was placed on water-ice following collection. Final storage at approximately −70° C.

Plasma samples were analyzed by solid phase extraction or direct protein precipitation followed by UPLC-MS/MS. MS detection using electrospray in the positive ion mode with monitoring of specific mass-to-charge transitions for compound (I) using internal standards for correcting the response. The concentration-time data was analyzed, using standard software using appropriate noncompartmental techniques to obtain estimates of the derived PK parameters. Instrumentation Used for Analysis of Compound (I) from Dosing Compound (Ia):

Mass spectrometer (LC-MS/MS) Waters Acquity-Sciex API 5000. Analytical column Waters BEH UPLC Phenyl 100×2.1 mm column, 1.7 μm particle size. Mobile phase A: 20 mM ammonium formate (aq)+0.5% formic acid. Mobile phase B: Acetonitrile. Gradient run from 95/5% to 2/98 in 6.1 minutes. Flow rate 0.5 mL/min. MRM monitoring (multiple reaction monitoring) of test item and the added analytical standards.

Dosing and blood sampling: Han Wistar rats were supplied by Charles River Laboratories, Sulzfeld, Germany. An artificial, automatically controlled, light and dark cycle of 12 hours was maintained. The rats received a standard laboratory diet from Brogaarden (Altromin 1324 pellets). The rats had unrestricted access to the diet. During the study (a 4-week toxicity study) the rats received once daily doses of (Ia) orally by gavage. From rats given 300 µg/kg (Ia), blood samples) from 3 male satellite animals were collected on the following time points at Day 29: 0.5, 1, 2, 4, 6, 8, 12 and 24 hours after dosing.

Instrumentation Used for Analysis of Compound (I) from Dosing of Compound (Ib):

Mass spectrometer (LC-MS/MS) Waters Acquity-Sciex API 5000. Analytical column Waters BEH UPLC Phenyl 100×2.1 mm column, 1.7 µm particle size. Mobile phase A: 20 mM ammonium formate (aq)+0.5% formic acid. Mobile phase B: Acetonitrile. Gradient run from 95/5% to 2/98 in 6.1 minutes. Flow rate 0.5 mL/min. MRM monitoring of test item and the added analytical standards.

Dosing and blood sampling: Han Wistar rats were supplied by Charles River Laboratories, UK. An artificial, automatically controlled, light and dark cycle of 12 hours was maintained. The rats received a standard laboratory diet (Teklad 2014C Diet.). The rats had unrestricted access to the diet. During the study (a 26-week toxicity study) the rats received once daily doses of (Ib) orally by gavage. From rats given 300 µg/kg (Ib), blood samples from 3 male satellite animals were collected on the following time points at day 182: 0.5, 1, 2, 4, 8 and 24 hours after dosing.

Instrumentation Used for Analysis of Compound (I) from Dosing of Compounds (Ic) and (Id)

Mass spectrometer (LC-MS/MS) Waters Acquity—Waters Xevo TQ-S. Analytical column Acquity BEH C18 100×2.1 mm, 1.7 µm. Mobile phase A: 20 mM NH$_4$-Formate+0.2% formic acid. Mobile phase B: Acetonitrile+ 0.2% formic acid. Gradient run from 95/5% to 5/95% in 11.0 minutes. Flow rate 0.3 mL/min. MRM monitoring of test item and the added analytical standards.

Dosing and blood sampling for compound (Id): Han Wistar rats were supplied by Charles River Laboratories, Wiga GmbH, Germany. An artificial, automatically controlled, light and dark cycle of 12 hours was maintained. The rats received a standard laboratory diet from Brogaarden (Altromin 1324 pellets). The rats had unrestricted access to the diet. Male Han Wistar rats were dosed a single oral gavage administration of compound (Id) orally by gavage. Rats were given 633 µg/kg of compound (Id), blood samples from 3 male animals were collected on the following time points at Day 1: 1, 2, 4, 6, 8, and 24 hours after dosing.

Dosing and blood sampling for compound (Ic): Han Wistar rats were supplied by Envigo, UK. An artificial, automatically controlled, light and dark cycle of 12 hours was maintained. The rats received a standard laboratory diet Teklad 2014C. The rats had unrestricted access to the diet. Male Han Wistar rats were dosed a single oral gavage administration of (Ic). Rats were given 494 µg/kg (Ic). Blood samples from 3 male animals were collected on the following time points at Day 1: 1, 2, 4, 6, 8, and 24 hours after dosing.

Instrumentation Used for Analysis of Apomorphine:

Mass spectrometer (UPCLC-MS/MS) Waters Acquity I-Class-Waters Xevo TQ-S. Analytical column Acquity HSS T3 C18 50×2.1 mm, 1.8 µm. Mobile phase A: 10 mM NH$_4$—Formate 0.2% formic acid:acetonitril (95:5). Mobile phase B: 10 mM NH$_4$—Formate 0.2% formic acid:acetonitril (5:95). Gradient run from 95/5% to 5/95% in 2.40 minutes. Flow rate 0.3 mL/min. MRM detection of test items and the added analytical standards.

Dosing and Blood Sampling for Apomorphine:

Animals for the study were as described in Example 9. Additionally, rats were administered a single dose of apomorphine subcutaneously. From rats administered 3000 µg/kg (apomorphine), blood samples from 3 male animals were collected on the following time points at Day 1: 0.25, 0.5, 1, 1.5, 2, 3, 5 and 7 hours SC administration after dosing.

TABLE 3

PK parameters for (4aR,10aR)-1-Propyl-1,2,3,4,4a,5,10,10a-octahydro-benzo[g]quinoline-6,7-diol (compound (I)) after oral dosing of 0.300 mg/kg compound (Ia), 0.300 mg/kg compound (Ib), 0.633 mg/kg of TFA salt of compound (Id) and 494 µg/kg compound (Ic) to Wistar rats according to Example 9

|  | compound | $T_{max}$ (h) | $C_{max}$ (pg/mL) | $AUC_{0-24}$ (pg*h/mL) | $t_{1/2}$ (h) | 24 h exposure (pg/mL) |
|---|---|---|---|---|---|---|
| Prodrugs in the state of the art | (Ia) | 1.0 | 3160 | 13600 | 4.09 | 48 ± 26 |
|  | (Ib) | 0.5 | 4990 | 31000 | N/A | 147 ± 28 |
|  | (Ic) | 1.0 | 14 | 104 | N/A | N/A |
| Compound obtained by the invention | (Id) | 4.0 | 1350 | 15500 | 6.8 | 208 ± 89 |

Example 10: PK/PD of Compound (Id)/Compound (I) in Rat Hyperactivity Assay

Animals

In total, 206 male CD rats (Charles River, Germany) weighing 200-250 grams (165-190 grams upon arrival) were used in the study. Animals were housed at a standard temperature (22±1° C.) and in a light-controlled environment (lights on from 7 am to 8 µm) with ad libitum access to food and water. The experiment described below was performed in accordance with the standard operating procedures of Charles River Discovery Research Services Finland Ltd. and in accordance with the national Animal Experiment Board of Finland (Eläinkoelautakunta, ELLA) authority on animal testing.

Locomotor Activity Testing, Open Field

The test device is a square Plexiglass-arena (measuring 40×40×40 cm), in which the movement paths of the rats are recorded by an activity monitor (Med. Associates Inc.). Before the test period is initiated, rats are habituated to their test cage for 60 minutes. Upon completion of habituation, animals were treated with either compound or vehicle and placed back into the open field apparatus. The main test parameter measured is ambulatory distance (recorded in 5 minute segments). Overall time of measurement after receiving initial treatment was 360 minutes. Total follow up period in the study was 420 minutes, including 60 minutes of habituation.

Results

Oral administration of compound (Id) was assessed in the rat locomotor activity assay, and this functional readout was then correlated to plasma concentrations of compound (I). Apomorphine and pramipexole were also concomitantly tested in this assay as comparators (i.e. known standard-of-care (SoC) in the Parkinson's Disease field), and plasma concentration was analyzed for apomorphine.

As shown in FIG. 3, compound (Id) (10 to 300 µg/kg, p.o.) increases locomotor activity with an effect starting approximatively 2 hours' post-administration (around the 180-minute time point) and lasting until the end of recording (at the 415-minute time point). In contrast, the hyperactivity induced by apomorphine (3 mg/kg, s.c.) is immediate but short-lasting as the effect is gone 1.5 hours. post administration (at the 150-minute time point). Pramipexole (0.3 mg/kg, s.c.) also induces an increase in activity, but its effect appears about 1 hour post administration and is gone 2.5 hours later (at the 270-minute time point). The total distance travelled as seen in FIG. 2 demonstrates a significantly increased activity for both compound (Id) and the two comparators tested, and this effect is the one that is to be expected from dopamine agonists.

In parallel with the locomotor activity assessment, plasma samples were taken from satellite animals at 6 different time points (1.5, 2, 3, 4, 5 & 7 hour's post-dose for animals treated with compound (Id)). Pharmacokinetic analysis demonstrates that the behavioral effects of compound (Id) (100 µg/kg, p.o.) correlate with the plasma concentrations of compound (I) (see FIG. 4), demonstrating that the behavioral effect of compound (Id) is driven by Compound (I) rather than by Compound (Id) itself. The corresponding exposure analysis of apomorphine (at 1.25 1.5, 2, 3, 5 and 7 hours post-dose) resulted in a correlation between plasma concentrations of apomorphine and hyperactive behavior (see FIG. 5).

REFERENCE LIST

U.S. Pat. No. 4,543,256
WO2001/078713
WO 02/100377
WO2009/026934
WO2009/026935
WO2010/097092
WO2019101917
Alexander et Crutcher, (1990) Trends in Neuroscience 13: 266-71
Bibbiani et al., Chase Experimental Neurology (2005), 192: 73-78
Campbell et al., Neuropharmacology (1982); 21(10): 953-961
Cannon et al., J. Heterocyclic Chem. (1980); 17: 1633-1636
Cavero and Guillon, J. Pharmacol. Toxicol. Methods (2014), 69: 150-161
Delong, (1990) Trends in Neuroscience 13: 281-5
Gerfen et al, Science (1990) 250: 1429-32
Giardina and Williams; CNS Drug Reviews (2001), Vol. 7 (3): 305-316
Goswami et al., J. Nutritional Biochem. (2003) 14: 703-709
Grosset et al., Acta Neurol Scand. (2013), 128:166-171
Hauser et al., Movement Disorders (2016), Vol. 32 (9): 1367-1372
Hitoshi, T et al. (*Chem Pharm Bull*, 1986, 628)
Imai, K. et al (*RSC Adv.*, 2017, 7, 17968-17979)
Liu et al., J. Med. Chem. (2006), 49: 1494-1498
Liu et al., Bioorganic Med. Chem. (2008), 16: 3438-3444
Loev, B et al. (*JACS*, 1956, 78, p. 6095-6097)
Loozen, B. et al. (*Recueil des Travaux Chimiques des Pays Bas*, 1982, 101, 298-310), and
Mandell, L. et al (*J. Org. Chem.*, 1982, 47, 731-734)
Montanari, S. et al. (U.S. Pat. No. 5,747,513, 1998, A),
Nolen et al., J. Pharm Sci. (1995), 84 (6): 677-681
Poewe et al., Nature Review, (2017) vol 3 article 17013: 1-21
Remington, "The Science and Practice of Pharmacy", 22th edition (2013), Edited by Allen, Loyd V., Jr
Rothman et al., Circulation (2000), 102: 2836-2841
Shimada, X. et al. (Chemical and Pharmaceutical Bulletin), 1986, 34, 179-187
Sprenger and Poewe, CNS Drugs (2013), 27: 259-272
Sozio et al., Exp. Opin. Drug Disc. (2012); 7(5): 385-406
Stachulski, A. V. et al. *Nat. Prod. Rep.*, 2013, 30, 806-848
Stain-Texier et al., Drug Metab. and Disposition (1998) 26 (5): 383-387
Stahl and Wermuth (Eds) "Handbook of Pharmaceutical salts. Properties, selection, and use", Wiley-VCH, 2008
Wiley-Interscience (publisher): Compendium of Organic Synthetic Methods, Vol. I-XII

The invention claimed is:

1. A process for the preparation of compound (Id) with the formula below

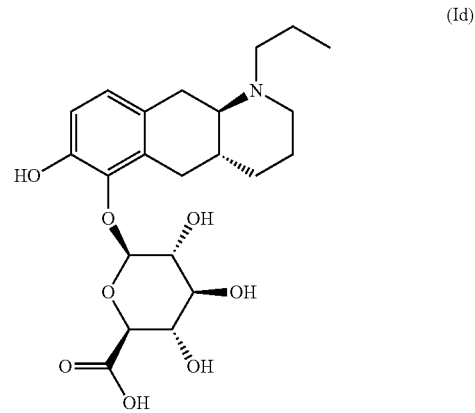 [SMILES: CCCN1CCC[C@@H]2Cc3c(ccc(O)c3O[C@@H]3O[C@H](C(=O)O)[C@@H](O)[C@H](O)[C@H]3O)C[C@H]21]

(Id)

from compound (I) with the formula below (I)

comprising the following step reacting compound (I), or a salt thereof, with benzyl halogenide to obtain compound (A2) according to the reaction scheme below

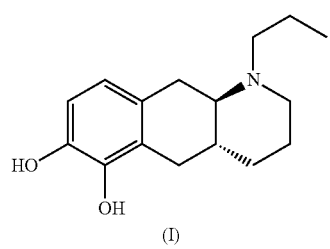 PhCH₂X ⟶

(I)

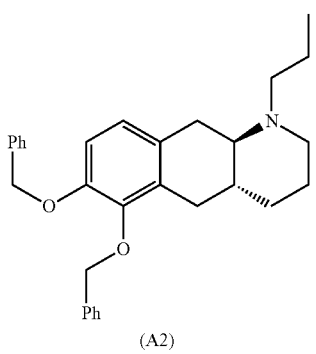

(A2)

wherein Ph is phenyl and X is selected from the group consisting of Cl, Br and I.

2. The process according to claim 1, wherein:
a) said benzyl halogenide is benzyl chloride and X is Cl; or
b) said benzyl halogenide is benzyl bromide and X is Br.

3. A compound of formula (A2) below:

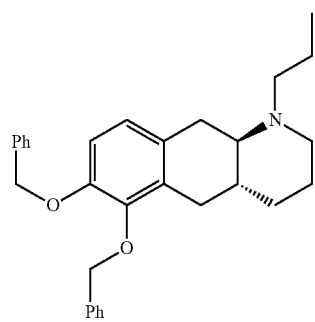

(A2)

or a salt thereof.

4. The process according to claim 1 for the preparation of compound (Id) with the formula below

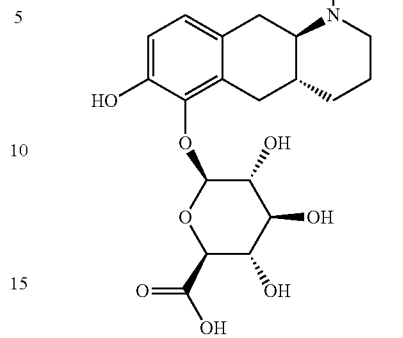

(Id)

from compound (I) with the formula below (I)

comprising the following step
subjecting compound (A2) to a debenzylation reaction to obtain compound (A3), or a salt thereof according to the reaction scheme below

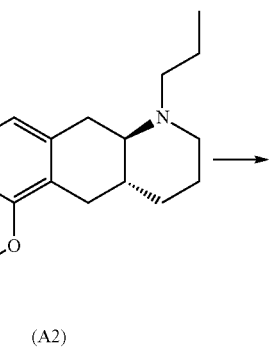

(A2)

⟶

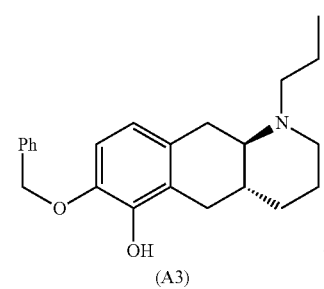

(A3)

5. A compound of formula (A3) below:

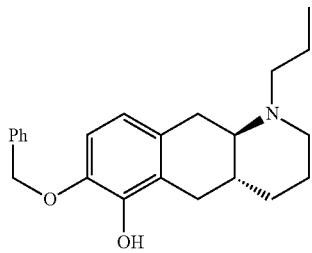

(A3)

or a salt thereof.

6. The process according to claim 4, wherein the debenzylation reaction comprises the steps of:
   I) reacting trimethylsilyl iodide with compound (A2) to form a mixture; and
   II) adding an alcohol to said mixture from step I) to obtain compound (A3) or a salt thereof; and
   III) optionally isolating compound (A3), or a salt thereof as obtained in step (II).

7. The process according to claim 6, wherein the alcohol added to said mixture in step II) is selected from the group consisting of MeOH, n-heptyl alcohol, and ethanol.

8. The process according to claim 4, wherein compound (A3) is obtained in the form of a hydroiodide salt with the formula (A3-HI) below

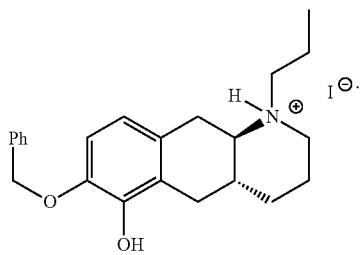

(A3-HI)

9. The compound according to claim 5, which is in the form of a hydroiodide salt with the formula (A3-HI) below

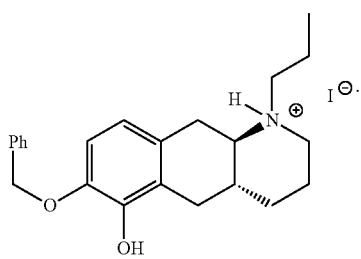

(A3-HI)

10. The process according to claim 1 for the preparation of compound (Id) with the formula below

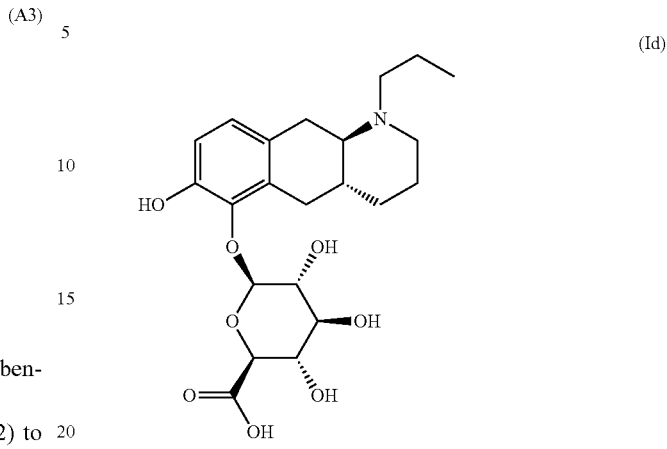

(Id)

from compound (I) with the formula below

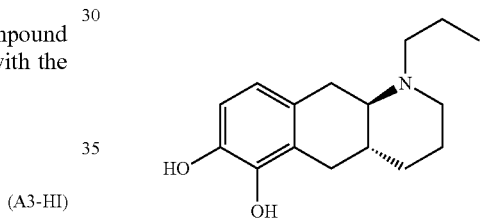

(I)

comprising the following step
   reacting compound (A3), or salt thereof, with (2S,3S, 4S,5R,6R)-2-(methoxycarbonyl)-6-(2,2,2-trichloro-1-iminoethoxy)tetrahydro-2H-pyran-3,4,5-triyl triacetate to obtain compound (A4) according to the reaction scheme below

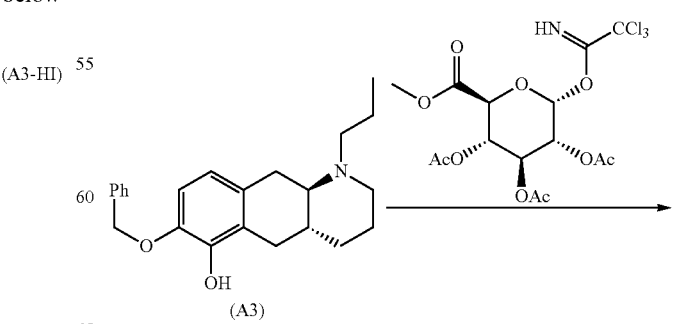

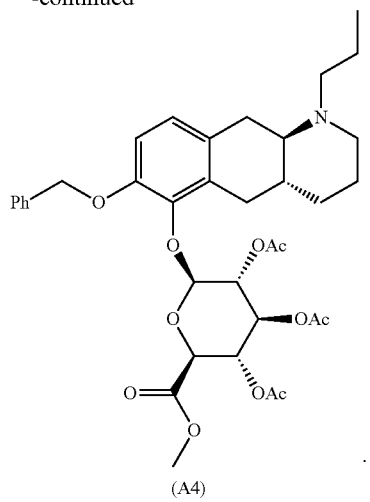

(A4)

11. The process according to claim 10, wherein compound (A3) is in the form of the hydroiodide salt (A3-HI) with the formula below:

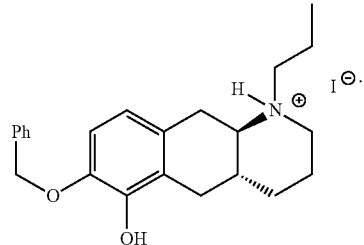

(A3-HI)

12. A compound of formula (A4) below:

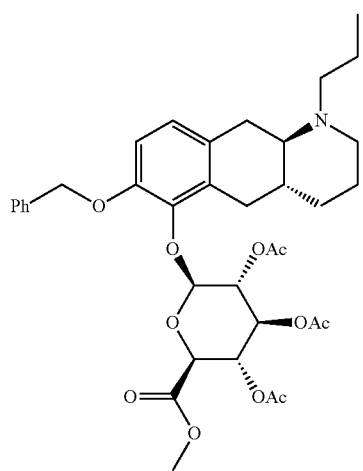

(A4)

or a salt thereof.

13. A process for the preparation of compound (Id) with the formula below

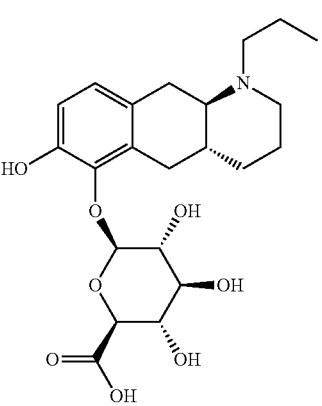

(Id)

from compound (I) with the formula below

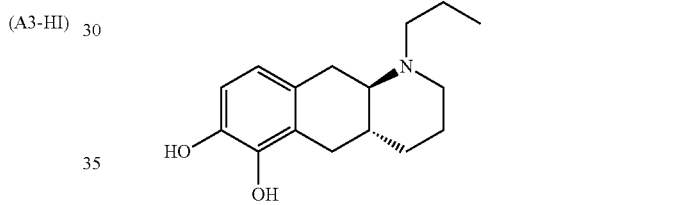

(I)

comprising the following step reacting compound (A4) with alkali-hydroxide to obtain (A5-Y) according to the reaction scheme below

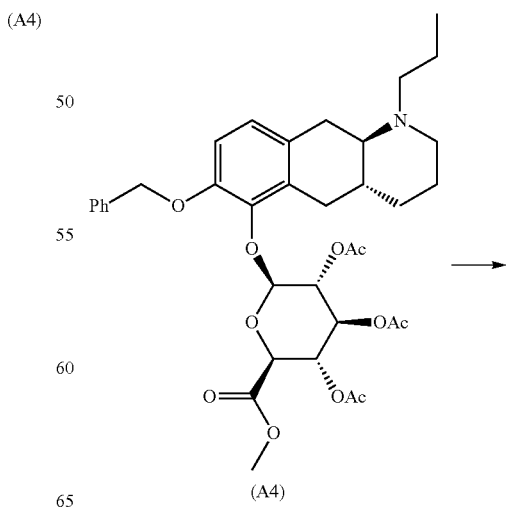

(A4)

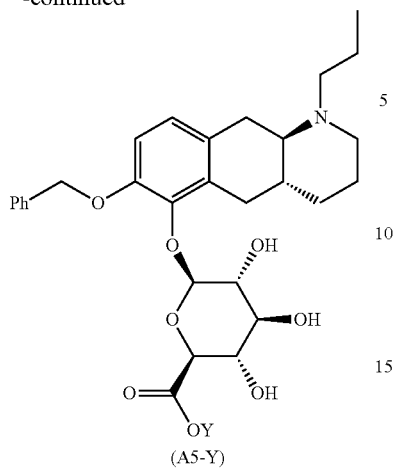

wherein Y is selected from Li, Na and K.

14. The process according to claim 13, wherein:

a) said alkali hydroxide is lithium hydroxide and Y is Li; or
b) said alkali hydroxide is sodium hydroxide and Y is Na; or
c) said alkali hydroxide is potassium hydroxide and Y is K.

15. A compound of formula (A5) below:

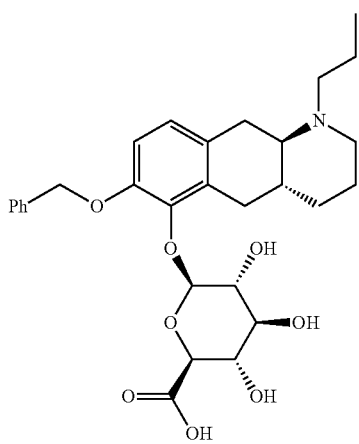

or a salt thereof.

16. The compound according to claim 15 which is in the form of an alkali salt depicted below

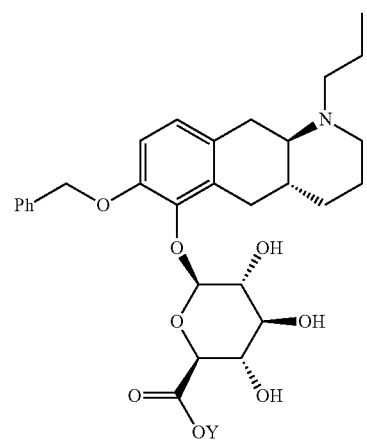

wherein Y is selected from the group consisting of Li, Na and K.

17. The process according to claim 1 for the preparation of compound (Id) with the formula below

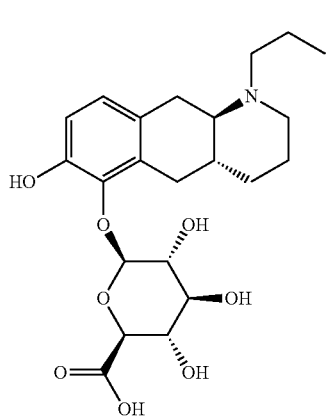

from compound (I) with the formula below

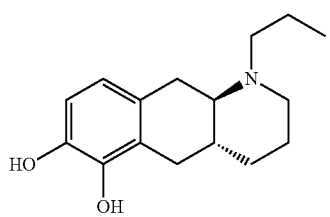

comprising the following step debenzylating compound (A5-Y) to obtain compound (Id) according to the reaction scheme below

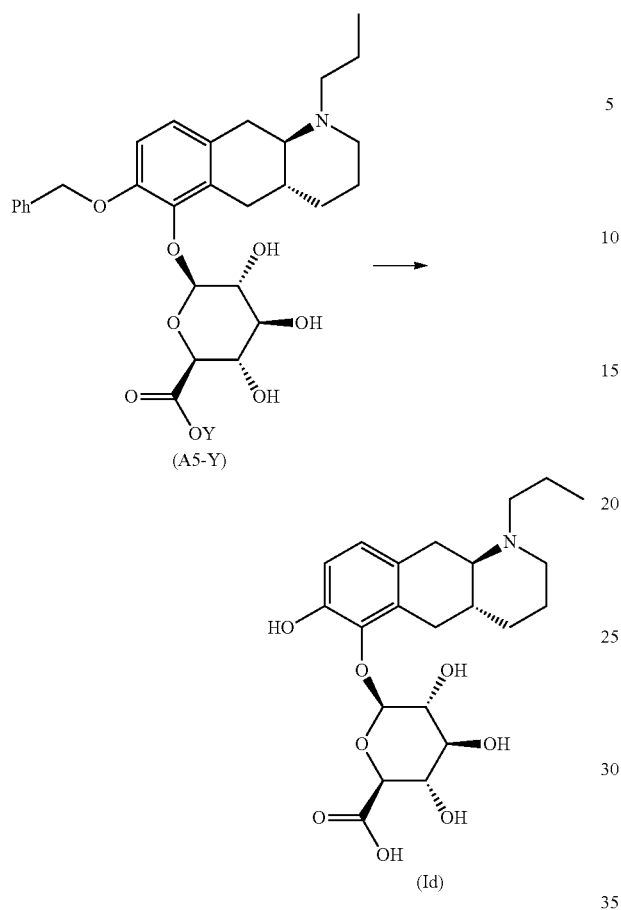

(A5-Y)

(Id)

wherein Y is selected from the group consisting of Li, Na, and K.

18. The process according to claim 1 for the preparation of compound (Id) from compound (I) comprising a step reacting compound (I), or a salt thereof, with benzyl halogenide to obtain compound (A2) according to the reaction scheme below

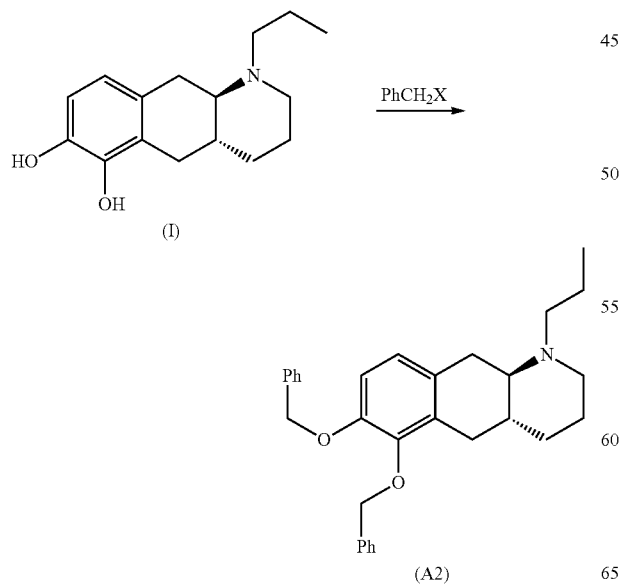

wherein Ph is phenyl and X is selected from the group consisting of Cl, Br and I; followed by a step subjecting compound (A2) to a debenzylation reaction to obtain compound (A3), or a salt thereof according to the reaction scheme below

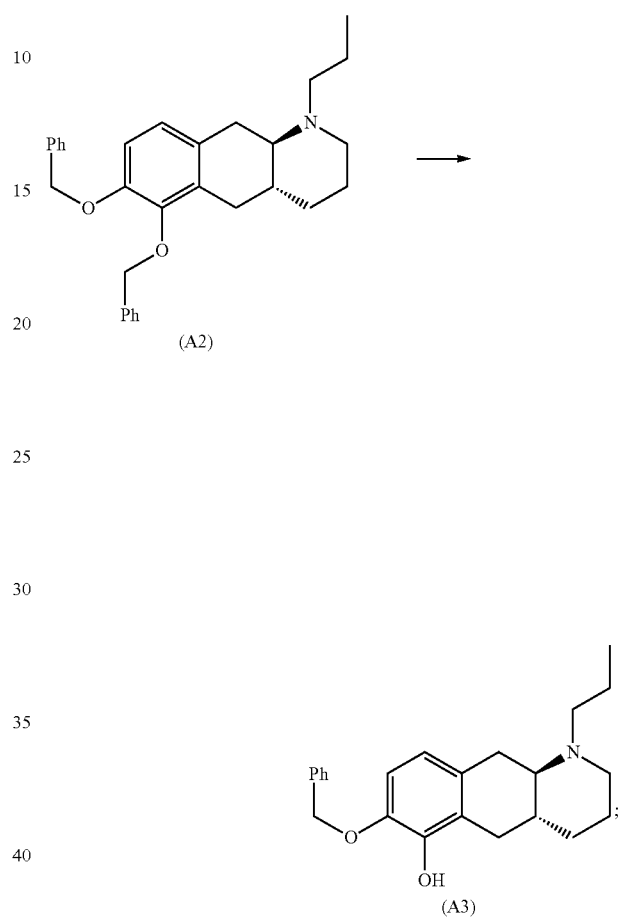

followed by a step reacting compound (A3), or salt thereof, with (2S,3S,4S,5R,6R)-2-(methoxycarbonyl)-6-(2,2,2-trichloro-1-iminoethoxy)tetrahydro-2H-pyran-3,4,5-triyl triacetate to obtain compound (A4) according to the reaction scheme below

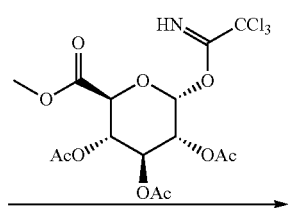

-continued
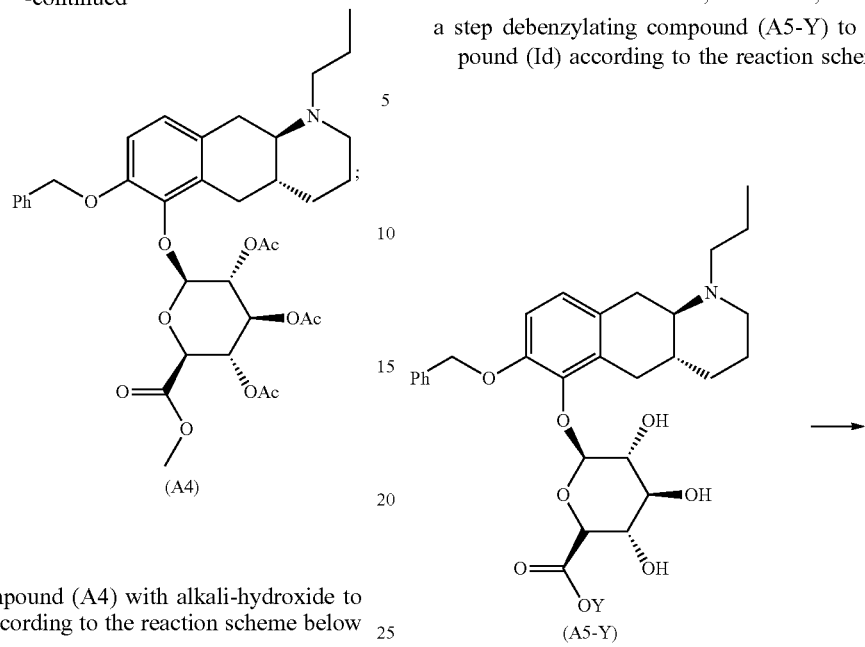
followed by
a step reacting compound (A4) with alkali-hydroxide to obtain (A5-Y) according to the reaction scheme below
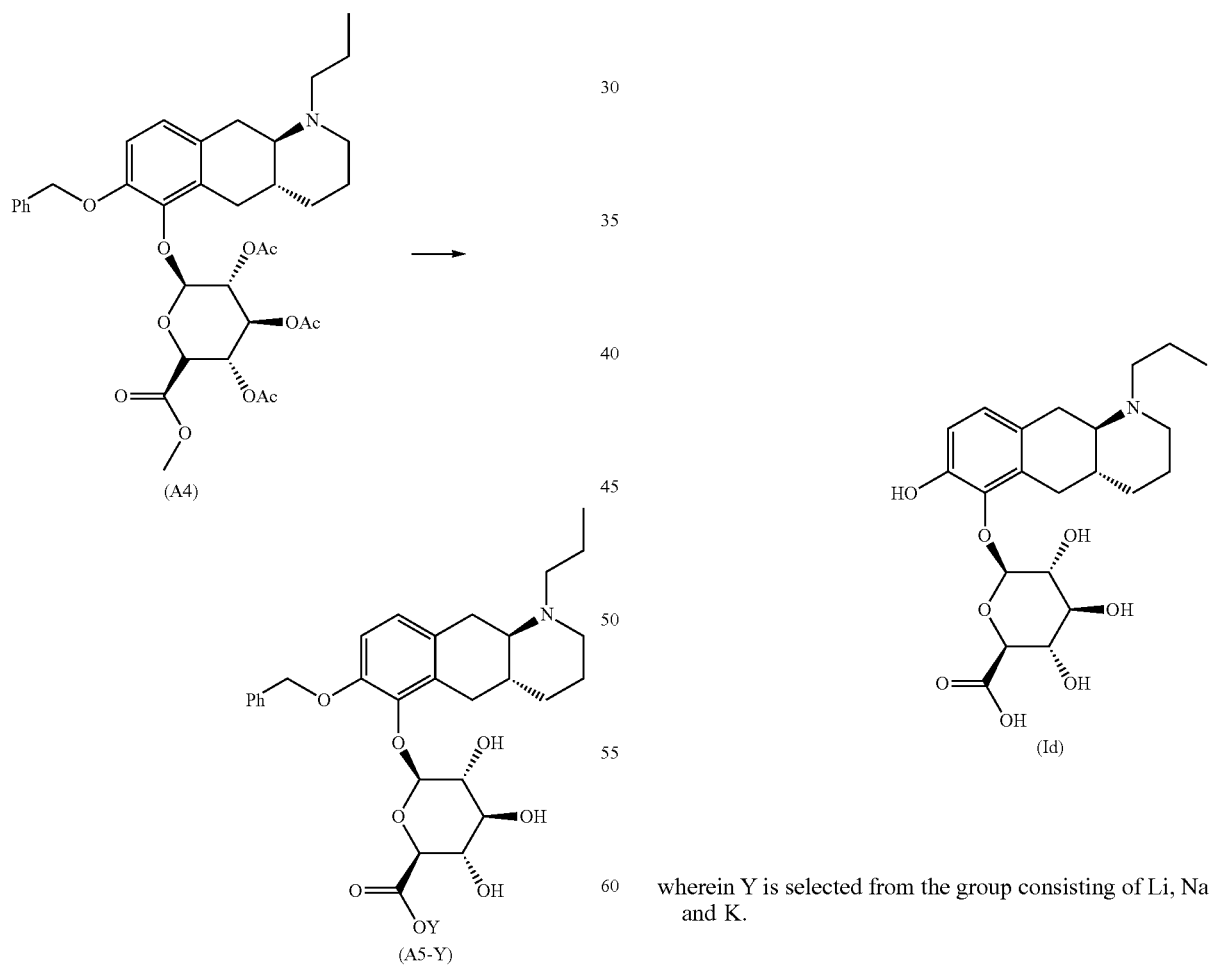
wherein Y is selected from Li, Na and K; followed by a step debenzylating compound (A5-Y) to obtain compound (Id) according to the reaction scheme below
wherein Y is selected from the group consisting of Li, Na and K.
* * * * *